United States Patent
Devraj et al.

(10) Patent No.: US 11,026,937 B2
(45) Date of Patent: Jun. 8, 2021

(54) HETEROARYL INHIBITORS OF PAD4

(71) Applicant: PADLOCK THERAPEUTICS, INC., Princeton, NJ (US)

(72) Inventors: Rajesh Devraj, Chesterfield, MO (US); Gnanasambandam Kumaravel, Lexington, MA (US); Cristina Lecci, Abingdon (GB); Pui Leng Loke, Abingdon (GB); Mirco Meniconi, Abingdon (GB); Nathaniel Julius Thomas Monck, Abingdon (GB); Carl Leslie North, Abingdon (GB); Mark Peter Ridgill, Abingdon (GB); Heather Tye, Abingdon (GB)

(73) Assignee: Padlock Therapeutics, Inc., Princeton, NJ (US)

( * ) Notice: Subject to any disclaimer, the term of this patent is extended or adjusted under 35 U.S.C. 154(b) by 0 days.

(21) Appl. No.: 16/331,622

(22) PCT Filed: Sep. 11, 2017

(86) PCT No.: PCT/US2017/050886
§ 371 (c)(1),
(2) Date: Mar. 8, 2019

(87) PCT Pub. No.: WO2018/049296
PCT Pub. Date: Mar. 15, 2018

(65) Prior Publication Data
US 2019/0358216 A1 Nov. 28, 2019

Related U.S. Application Data

(60) Provisional application No. 62/393,209, filed on Sep. 12, 2016.

(51) Int. Cl.
*C07D 471/04* (2006.01)
*A61K 31/4375* (2006.01)
*A61K 31/47* (2006.01)
*A61K 31/4412* (2006.01)
*A61K 31/4709* (2006.01)
*A61K 31/5377* (2006.01)
*C07D 213/647* (2006.01)
*C07D 215/227* (2006.01)
*C07D 401/14* (2006.01)
*C07D 413/06* (2006.01)

(52) U.S. Cl.
CPC .......... *A61K 31/47* (2013.01); *A61K 31/4412* (2013.01); *A61K 31/4709* (2013.01); *A61K 31/5377* (2013.01); *C07D 213/647* (2013.01); *C07D 215/227* (2013.01); *C07D 401/14* (2013.01); *C07D 413/06* (2013.01)

(58) Field of Classification Search
CPC .......... C07D 471/04; A61K 31/4375
USPC .......... 546/123; 514/300
See application file for complete search history.

(56) References Cited

U.S. PATENT DOCUMENTS

| 2005/0165053 A1* | 7/2005 | Cai et al. ........... | A61K 31/47 514/312 |
| 2009/0143368 A1 | 6/2009 | Shiraki et al. | |
| 2012/0190707 A1 | 7/2012 | Ronai et al. | |

FOREIGN PATENT DOCUMENTS

| CN | 105315333 A | 2/2016 |
| CN | 105820058 A | 8/2016 |
| EP | 1671948 A1 | 6/2006 |
| EP | 1987717 A1 | 11/2008 |
| JP | 2002371078 A | 12/2002 |
| WO | WO200047205 A1 | 8/2002 |
| WO | WO2014015905 A1 | 1/2014 |
| WO | WO2016140973 A1 | 9/2016 |
| WO | WO2016185279 A1 | 11/2016 |
| WO | WO2017/100601 A1 | 6/2017 |
| WO | WO2017/100594 A1 | 7/2017 |
| WO | WO2017147102 A1 | 8/2017 |
| WO | WO2018022897 A1 | 2/2018 |

OTHER PUBLICATIONS

Barile, et al., "Synthesis and SAR Studies of Dual AKT/NF-[kappa]B Inhibitors Against Melanoma", Chemical Biology & Drug Design, vol. 82(5), pp. 520-533 (2013).
Berge et al., "Pharmaceutical Salts", Journal of Pharmaceutical Sciences, vol. 66(1), pp. 1-19 (1977).
Brinkmann et al., "Neutrophil extracellular traps kill bacteria", Science vol. 303(5663) pp. 1532-1535 ( 2004).
Chang, et al., "Increased PADI4 expression in blood and tissues of patients with malignant tumors", BMC Cancer, vol. 9(40), pp. 1-11 (2009).
Chumanevich, et al., "Suppression of colitis in mice by CI-amidine: a novel peptidylarginine deiminase inhibitor", American J of Physiology, Gastrointestinal and Liver Physiology, vol. 300(6), pp. G929-G938 (2011).
Clark, et al., "Platelet TLR4 activates neutrophil extracellular traps to ensnare bacteria in septic blood", Nature Medicine, vol. 13(4), pp. 463-469 (2007).
Dworski et al., "Eosinophil and neutrophil extracellular DNA traps in human allergic asthmatic airways", The Journal of Allergy and Clinical Immunology, vol. 127(5), pp. 1260-1266 (2011).
Fuchs, et al., "Extracellular DNA traps promote thrombosis", PNAS, vol. 107(36), pp. 15880-15885 (2010).
Ghouse, et al., "Green chemical approach: microwave assisted, titanium dioxide nanoparticles catalyzed, convenient and efficient C-C bond formation in the synthesis of highly functionalized quinolines and quinolinones", RSC Advances, vol. 4(84), pp. 44408-44417 (2014).
Hakkim et al., "Impairment of neutrophil extracellular trap degradation is associated with lupus nephritis", PNAS, vol. 107(21), pp. 9813-9818 (2010).

(Continued)

*Primary Examiner* — Charanjit Aulakh
(74) *Attorney, Agent, or Firm* — Hong Liu

(57) ABSTRACT

The present invention provides compounds useful as inhibitors of PAD4, compositions thereof, and methods of treating PAD4-related disorders.

7 Claims, No Drawings

(56) References Cited

OTHER PUBLICATIONS

ISR issued by USPTO for Application No. PCT/US2016/065857 dated Apr. 17, 2017 (10 pages).
Jones et al., "Protein arginine deiminase 4 (PAD4): current understanding and future therapeutic potential", Current Opinion in Drug Discovery & Development, vol. 12(5), pp. 616-627 (2009).
Kalashnikov et al., "Features of reaction of aromatic nitro-substituted aldehydes with ketones on the matrix of 2(1H)-pyridone", Russian Journal of General Chemistry, vol. 79(6), pp. 1201-1203 (2009).
Kessenbrock et al., "Netting neutrophils in autoimmune small-vessel vasculitis", Nature Medicine, vol. 15(6), pp. 623-625 (2009).
Kochi et al., "PADI4 polymorphism predisposes male smokers to rheumatoid arthritis", Annals of the Rheumatic Diseases, vol. 70(3), pp. 512-515 (2011).
Lange et al., "Protein deiminases: New players in the developmentally regulated loss of neutral regenerative ability", Developmental Biology, vol. 355(2), 205-214 (2011).
Lewis et al., "Inhibition of PAD4 activity is sufficient to disrupt mouse and human NET formation", Nature Chemical Biology, vol. 11(3) pp. 189-191 (2015).
Li et al., "PAD4 is essential for antibacterial innate immunity mediated by neutrophil extracellular traps", JEM, vol. 207 (9), pp. 1853-1862 (2010).
Li et al., "Regulation of p53 Target Gene Expression by Peptidylarginine Deiminase 4", Molecular and Cellular Biology, vol. 28(15), pp. 4745-4758 (2008).
Lin et al., "Mast Cells and Neutrophils Release IL-17 through Extracellular Trip Formation in Psoriasis", The Journal of Immunology, vol. 187(1), pp. 490-500 (2011).

Moffett, Robert Bruce, "Claisen Rearrangement of Allyloxypyridines" The Journal of Organic Chemistry, vol. 28(10), pp. 2885-2886 (1963).
Neeli et al., "Histone Deimination As a Response to Inflammatory Stimuli in Neutrophils", The Journal of Immunology, vol. 108(3), pp. 1895-1902 (2008).
Pubchem, "Substance Record for SID 1730220505," retrieved from http://pubchem.ncbi.nim.nih.gov/substance/173022050#Top accessed on Mar. 24, 2018 (5 pages).
Sail, V. et al., "Identification of Small Molecule Hes1 Modulators as Potential Anticancer Chemotherapeutics", Chemical Biology & Drug Design, vol. 81(3), pp. 334-342 (2013).
Sarmiento, et al., "Structure-based discovery of small molecule inhibitors targeted to protein tyrosine phosphatase 1B", J. of Medicinal Chemistry, vol. 43(2), pp. 146-155 (2000).
Slack et al., "Protein Arginine Deiminase 4: a target for an epigenetic cancer therapy", Cellular and Molecular Life Sciences, vol. 68(4), pp. 709-720 (2011).
Villanueva et al., "Netting Neutrophils Induce Endothelial Damage, Infiltrate Tissues, and Expose Immunostimulatory Molecules in Systemic Lupus Erythematosus", The Journal of Immunology, vol. 187(1), pp. 538-552 (2011).
Vitkov et al., "Neutrophil Fate in Gingival Crevicular Fluid", Ultrastructrual Pathology, vol. 34(1), pp. 1-6 (2010).
Wegner et al., "Autoimmunity to specific citrullinated proteins gives the first clues to the etiology of rheumatoid arthritis", Immunological Reviews, vol. 233(1), pp. 34-54 (2010).
Willis et al., "N-a-Benzoyl-N5-(2-Chloro-1-Iminoethyl)-L-Ornithine Amide, a Protein Arginine Deiminase Inhibitor, Reduces the Severity Murine Collagen-Induced Arthritis", The J. of Immunology, vol. 186(7), pp. 4396-4404 (2011).
Savchenko, et al. "Long pentraxin 3 (PTX3) expression and release by neutrophils in vitro and in ulcerative colitis", Pathology International 2011; 61: 290-297.

* cited by examiner

HETEROARYL INHIBITORS OF PAD4

CROSS REFERENCE TO RELATED APPLICATIONS

This application is a 371 application of PCT/US2017/050886 filed Sep. 11, 2017 which is entitled to priority pursuant to 35 U.S.C. § 119(e) to U.S. provisional patent application No. 62/393,209, filed Sep. 12, 2016, which is incorporated herein in its entirety.

BACKGROUND OF THE INVENTION

PAD4 is a member of the peptidylarginine deiminase (PAD) family of enzymes capable of catalysing the citrullination of arginine into citrulline within peptide sequences. PAD4 is responsible for the deimination or citrullination of a variety of proteins in vitro and in vivo, with consequences of diverse functional responses in a variety of diseases (Jones J. E. et al, Curr. Opin. Drug Discov. Devel., 12(5), (2009), 616-627). Examples of exemplar diseases include rheumatoid arthritis, diseases with neutrophilic contributions to pathogenesis (for example vasculitis, systemic lupus erythematosus, ulcerative colitis) in addition to oncology indications. PAD4 inhibitors also have wider applicability as tools and therapeutics for human disease through epigenetic mechanisms.

Inhibitors of PAD4 have utility against Rheumatoid Arthritis (RA). RA is an autoimmune disease affecting approximately 1% of the population (Wegner N. et al, Immunol. Rev., 233(1) (2010), 34-54). It is characterised by inflammation of articular joints leading to debilitating destruction of bone and cartilage. A weak genetic association between PAD4 polymorphisms and susceptibility to RA has been suggested, albeit inconsistently, in a number of population studies (Kochi Y. et al, Ann. Rheum. Dis., 70, (2011), 512-515). PAD4 (along with family member PAD2) has been detected in synovial tissue where it is responsible for the deimination of a variety of joint proteins. This process is presumed to lead to a break of tolerance to, and initiation of immune responses to, citrullinated substrates such as fibrinogen, vimentin and collagen in RA joints. These anti-citrullinated protein antibodies (ACPA) contribute to disease pathogenesis and may also be used as a diagnostic test for RA (e.g. the commercially available CCP2 or cyclic citrullinated protein 2 test). In addition, increased citrullination may also offer additional direct contributions to disease pathogenesis through its ability to affect directly the function of several joint and inflammatory mediators (e.g. fibrinogen, anti-thrombin, multiple chemokines). In a smaller subset of RA patients, anti-PAD4 antibodies can be measured and may correlate with a more erosive form of the disease.

PAD4 inhibitors are also useful for the reduction of pathological neutrophil activity in a variety of diseases. Studies suggest that the process of Neutrophil Extracellular Trap (NET) formation, an innate defence mechanism by which neutrophils are able to immobilise and kill pathogens, is associated with histone citrulllination and is deficient in PAD4 knockout mice (Neeli I. et al, J. Immunol., 180, (2008), 1895-1902 and Li P. et al, J. Exp. Med., 207(9), (2010), 1853-1862). PAD4 inhibitors may therefore have applicability for diseases where NET formation in tissues contributes to local injury and disease pathology. Such diseases include, but are not limited to, small vessel vasculitis (Kessenbrock K. et al, Nat. Med., 15(6), (2009), 623-625), systemic lupus erythematosus (Hakkim A. et al, Proc. Natl. Acad. Sci. USA, 107(21), (2010), 9813-9818 and Villanueva E. et al, J. Immunol., 187(1), (2011), 538-52), ulcerative colitis (Savchenko A. et al, Pathol. Int., 61(5), (2011), 290-7), cystic fibrosis, asthma (Dworski R. et al, J. Allergy Clin. Immunol., 127(5), (2011), 1260-6), deep vein thrombosis (Fuchs T. et al, Proc. Natl. Acad. Sci. USA, 107(36), (2010), 15880-5), periodontitis (Vitkov L. et al, Ultrastructural Pathol., 34(1), (2010), 25-30), sepsis (Clark S. R. et al, Nat. Med., 13(4), (2007), 463-9), appendicitis (Brinkmann V. et al, Science, 303, (2004), 1532-5), and stroke. In addition, there is evidence that NETs may contribute to pathology in diseases affecting the skin, eg in cutaneous lupus erythematosis (Villanueva E. et al, J. Immunol., 187(1), (2011), 538-52) and psoriasis (Lin A. M. et al., J. Immunol., 187(1), (2011), 490-500), so a PAD4 inhibitor may show benefit to tackle NET skin diseases, when administered by a systemic or cutaneous route. PAD4 inhibitors may affect additional functions within neutrophils and have wider applicability to neutrophilic diseases.

Studies have demonstrated efficacy of tool PAD inhibitors (for example chloro-amidine) in a number of animal models of disease, including collagen-induced arthritis (Willis V. C. et al, J. Immunol., 186(7), (2011), 4396-4404), dextran sulfate sodium (DSS)-induced experimental colitis (Chumanevich A. A. et al, Am. J. Physiol. Gastrointest. Liver Physiol., 300(6), (2011), G929-G938), spinal cord repair (Lange S. et al, Dev. Biol., 355(2), (2011), 205-14), and experimental autoimmune encephalomyelitis (EAE). The DSS colitis report also demonstrates that chloro-amidine drives apoptosis of inflammatory cells both in vitro and in vivo, suggesting that PAD4 inhibitors may be effective more generally in widespread inflammatory diseases.

PAD4 inhibitors are also useful in the treatment of cancers (Slack. J. L. et al, Cell. Mol. Life Sci., 68(4), (2011), 709-720). Over-expression of PAD4 has been demonstrated in numerous cancers (Chang X. et al, BMC Cancer, 9, (2009), 40). An anti-proliferative role has been suggested for PAD4 inhibitors from the observation that PAD4 citrullinates arginine residues in histones at the promoters of p53-target genes such as p21, which are involved in cell cycle arrest and induction of apoptosis (Li P. et al, Mol. Cell Biol., 28(15), (2008), 4745-4758).

The aforementioned role of PAD4 in deiminating arginine residues in histones may be indicative of a role for PAD4 in epigenetic regulation of gene expression. PAD4 is the primary PAD family member observed to be resident in the nucleus as well as the cytoplasm. Early evidence that PAD4 may act as a histone demethyliminase as well as a deiminase is inconsistent and unproven. However, it may reduce histone arginine methylation (and hence epigenetic regulation associated with this mark) indirectly via depletion of available arginine residues by conversion to citrulline. PAD4 inhibitors are useful as epigenetic tools or therapeutics for affecting expression of varied target genes in additional disease settings. Through such mechanisms, PAD4 inhibitors may also be effective in controlling citrullination levels in stem cells and may therefore therapeutically affect the pluripotency status and differentiation potential of diverse stem cells including, but not limited to, embryonic stem cells, neural stem cells, haematopoietic stem cells and cancer stem cells. Accordingly, there remains an unmet need to identify and develop PAD4 inhibitors for the treatment of PAD4-mediated disorders.

SUMMARY OF THE INVENTION

It has now been found that compounds of formulae I and II are useful as inhibitors of PAD4:

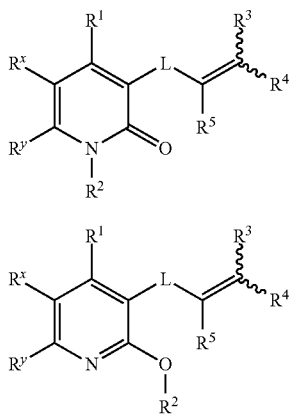

or a pharmaceutically acceptable salt thereof, wherein each of L, $R^1$, $R^2$, $R^3$, $R^4$, $R^5$, $R^x$ and $R^y$ is as defined and described herein.

In some embodiments, a provided compound demonstrates selectivity for PAD4 with respect to PAD2. The present invention also provides pharmaceutically acceptable compositions comprising a provided compound. Provided compounds are useful in treatment of various disorders associated with PAD4. Such disorders are described in detail, herein, and include, for example rheumatoid arthritis, vasculitis, systemic lupus erythematosus, ulcerative colitis, cancer, cystic fibrosis, asthma, cutaneous lupus erythematosis, and psoriasis.

DETAILED DESCRIPTION OF THE INVENTION

1. General Description of Certain Aspects of the Invention

In some embodiments, such compounds include those of the formulae described herein, or a pharmaceutically acceptable salt thereof, wherein each variable is as defined herein and described in embodiments. Such compounds have the structure of formula I or formula II:

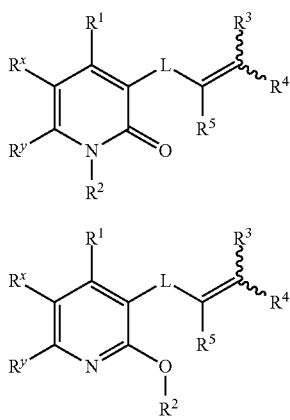

or a pharmaceutically acceptable salt thereof, wherein:

$R^1$ is hydrogen or an optionally substituted group selected from aliphatic, phenyl, a 5-6 membered monocyclic heteroaryl ring having 1-3 heteroatoms independently selected from nitrogen, oxygen, or sulfur, or a 4-7 membered monocyclic saturated or partially unsaturated heterocyclic ring having 1-2 heteroatoms independently selected from nitrogen, oxygen, or sulfur;

$R^2$ is hydrogen or optionally substituted $C_{1-6}$-aliphatic;

L is a covalent bond or a $C_{1-6}$ bivalent hydrocarbon chain wherein one or two methylene units of L are optionally and independently replaced by —C(O)—, —C(O)NH—, —NHC(O)—, or —S(O)$_2$—;

$R^3$ is hydrogen or Ring A;

Ring A is an optionally substituted ring selected from a 3-7 membered monocyclic saturated or partially unsaturated carbocyclic ring, phenyl, a 5-6 membered monocyclic heteroaryl ring having 1-3 heteroatoms independently selected from nitrogen, oxygen, or sulfur, or a 4-7 membered monocyclic saturated or partially unsaturated heterocyclic ring having 1-2 heteroatoms independently selected from nitrogen, oxygen, or sulfur, or an 8-10 membered bicyclic heteroaromatic ring having 1-5 heteroatoms independently selected from nitrogen, oxygen, or sulfur;

$R^4$ is R or —C(O)OR;

each R is independently hydrogen or $C_{1-6}$ aliphatic optionally substituted with 1-3 fluorine atoms;

$R^5$ is hydrogen or CN, or:
  $R^5$ and $R^4$ are taken together with their intervening atoms to form a triazole ring; or
  $R^5$ and $R^3$ are taken together with their intervening atoms to form a triazole ring; and $R^x$ and $R^y$ are each independently selected from hydrogen, halogen, optionally substituted $C_{1-6}$ aliphatic, or:
  $R^x$ and $R^y$ are taken together with their intervening atoms to form a optionally substituted 5-6 membered saturated, partially unsaturated, or aromatic fused ring having 1-2 heteroatoms independently selected from nitrogen, oxygen, or sulfur.

2. Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent.

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —O$(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$ which may be substituted with $R°$; —CH=CHPh, which may be substituted with $R°$; —$(CH_2)_{0-4}O(CH_2)_{0-1}$-pyridyl which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —OC(O)$(CH_2)_{0-4}SR—, SC(S)SRO; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R$; —$N(R°)S(O)_2NR°$; —$N(R°)S(O)_2R$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —($C_{1-4}$ straight or branched alkylene)O—$N(R°)_2$; or —($C_{1-4}$ straight or branched alkylene)C(O)O—$N(R°)_2$, wherein each $R°$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R°$ (or the ring formed by taking two independent occurrences of $R°$ together with their intervening atoms), are independently halogen, —$(CH_2)_{0-2}R^\bullet$, -(halo$R^\bullet$), —$(CH_2)_{0-2}OH$, —$(CH_2)_{0-2}OR^\bullet$, —$(CH_2)_{0-2}CH(OR^\bullet)_2$; —O(halo$R^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —($C_{1-4}$ straight or branched alkylene)C(O)O$R^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R°$ include =O and =S.

Suitable divalent substituents on a saturated carbon atom of an "optionally substituted" group include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O—$, or —$S(C(R^*_2))_{2-3}S—$, wherein each independent occurrence of $R^*$ is selected from hydrogen, $C_1$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^\bullet$, -(halo$R^\bullet$), —OH, —$OR^\bullet$, —O(halo$R^\bullet$), —CN, —C(O)OH, —$C(O)OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^\dagger$, —$NR^\dagger_2$, —$C(O)R^\dagger$, —$C(O)OR^\dagger$, —$C(O)C(O)R^\dagger$, —$C(O)CH_2C(O)R^\dagger$, —$S(O)_2R^\dagger$, —$S(O)_2NR^\dagger_2$, —$C(S)NR^\dagger_2$, —$C(NH)NR^\dagger_2$, or —$N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, —$R^\bullet$, -(halo$R^\bullet$), —OH, —$OR^\bullet$, —O(halo$R^\bullet$), —CN, —C(O)OH, —$C(O)OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

The terms "measurable affinity" and "measurably inhibit," as used herein, means a measurable change in PAD4 activity between a sample comprising a compound of the present invention, or composition thereof, and PAD4, and an equivalent sample comprising PAD4 in the absence of said compound, or composition thereof.

3. Description of Exemplary Compounds

According to one aspect, the present invention provides a compound of formula I-i, I-ii, II-i, or II-ii:

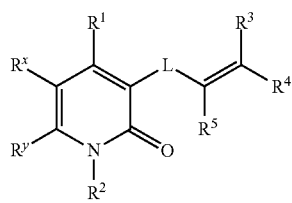

I-i

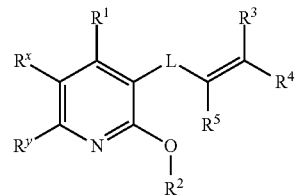

I-ii

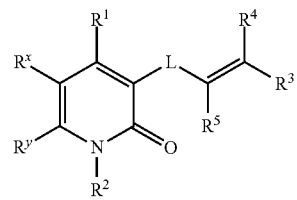

II-i

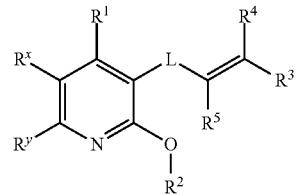

II-ii or a pharmaceutically acceptable salt thereof, wherein each of L, $R^1$, $R^2$, $R^3$, $R^4$, $R^5$, $R^x$ and $R^y$ is as defined and described herein.

In some embodiments, a provided compound is other than I-69, I-76 or I-114.

In some embodiments, a provided compound of formula I is other than those compounds depicted in Table 2, below.

As defined above and described herein, $R^1$ is hydrogen or an optionally substituted group selected from aliphatic, phenyl, a 5-6 membered monocyclic heteroaryl ring having 1-3 heteroatoms independently selected from nitrogen, oxygen, or sulfur, or a 4-7 membered monocyclic saturated or partially unsaturated heterocyclic ring having 1-2 heteroatoms independently selected from nitrogen, oxygen, or sulfur.

In some embodiments, $R^1$ is hydrogen. In some embodiments, $R^1$ is an optionally substituted aliphatic group. In some embodiments, $R^1$ is an optionally substituted phenyl. In some embodiments, $R^1$ is an optionally substituted 5-6 membered monocyclic heteroaryl ring having 1-3 atoms independently selected from nitrogen, oxygen or sulfur. In some embodiments, $R^1$ is a 4-7 membered monocyclic saturated or partially unsaturated heterocyclic ring having 1-2 heteroatoms independently selected from nitrogen, oxygen, or sulfur.

In some embodiments, $R^1$ is —$S(CH_3)$,

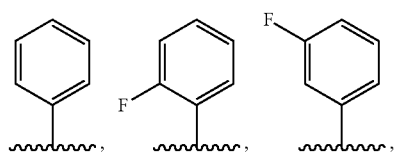

-continued

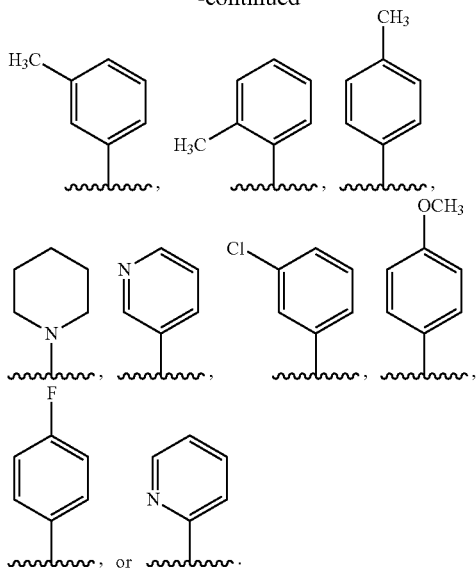

In some embodiments, $R^1$ is selected from those depicted in Table 1, below.

As defined above and described herein, $R^2$ is hydrogen or optionally substituted $C_{1-6}$-aliphatic.

In some embodiments, $R^2$ is hydrogen. In some embodiments, $R^2$ is optionally substituted $C_{1-6}$ aliphatic.

In some embodiments, $R^2$ is methyl, ethyl,

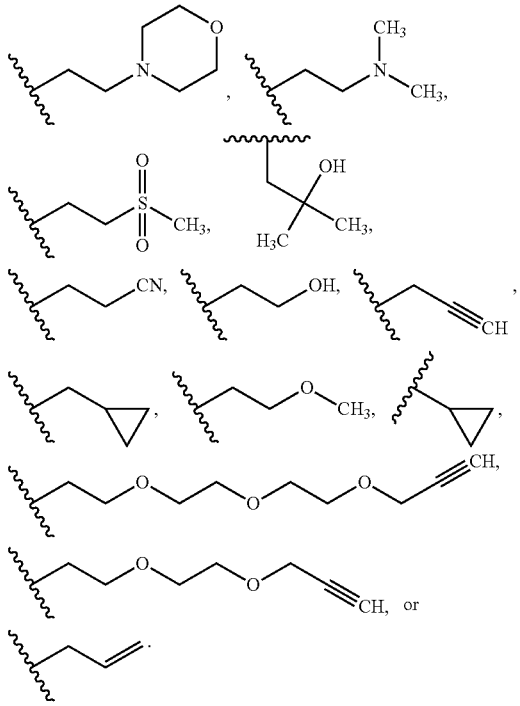

In some embodiments, $R^2$ is selected from those depicted in Table 1, below.

As defined above and described herein, L is a covalent bond or a $C_{1-6}$ bivalent hydrocarbon chain wherein one or two methylene units of L are optionally and independently replaced by —C(O)—, —C(O)NH—, —NHC(O)—, or —S(O)$_2$—.

In some embodiments, L is

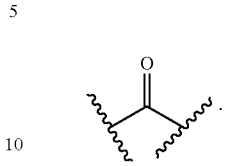

In some embodiments, L is

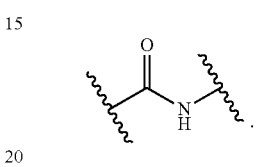

In some embodiments, L is

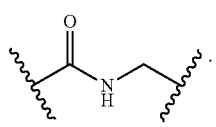 [SMILES: *CNC(*)=O]

In some embodiments, L is

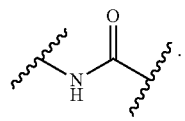 [SMILES: *NC(*)=O]

In some embodiments, L is

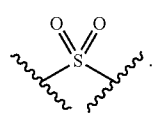

In some embodiments, L is selected from those depicted in Table 1, below.

As defined above and described herein, $R^3$ is hydrogen or Ring A. In some embodiments, $R^3$ is hydrogen. In some embodiments, $R^3$ is Ring A.

In some embodiments, $R^3$ is selected from those depicted in Table 1, below.

As defined above and described herein, Ring A is an optionally substituted ring selected from a 3-7 membered monocyclic saturated or partially unsaturated carbocyclic ring, phenyl, a 5-6 membered monocyclic heteroaryl ring having 1-3 heteroatoms independently selected from nitrogen, oxygen, or sulfur, or a 4-7 membered monocyclic saturated or partially unsaturated heterocyclic ring having 1-2 heteroatoms independently selected from nitrogen, oxygen, or sulfur, or an 8-10 membered bicyclic heteroaromatic ring having 1-5 heteroatoms independently selected from nitrogen, oxygen, or sulfur.

In some embodiments, Ring A is an optionally substituted ring selected from a 3-7 membered monocyclic saturated carbocyclic ring. In some embodiments, Ring A is an optionally substituted 3-7 membered monocyclic partially unsaturated carbocyclic ring. In some embodiments, Ring A is an optionally substituted phenyl ring. In some embodiments, Ring A is an optionally substituted 5-6 membered monocyclic heteroaryl ring having 1-3 heteroatoms independently selected from nitrogen, oxygen, or sulfur. In some embodiments, Ring A is an optionally substituted 4-7 membered monocyclic saturated or partially unsaturated heterocyclic ring having 1-2 heteroatoms independently selected from nitrogen, oxygen, or sulfur. In some embodiments, Ring A is an 8-10 membered bicyclic heteroaromatic ring having 1-5 heteroatoms independently selected from nitrogen, oxygen, or sulfur.

In some embodiments, Ring A is

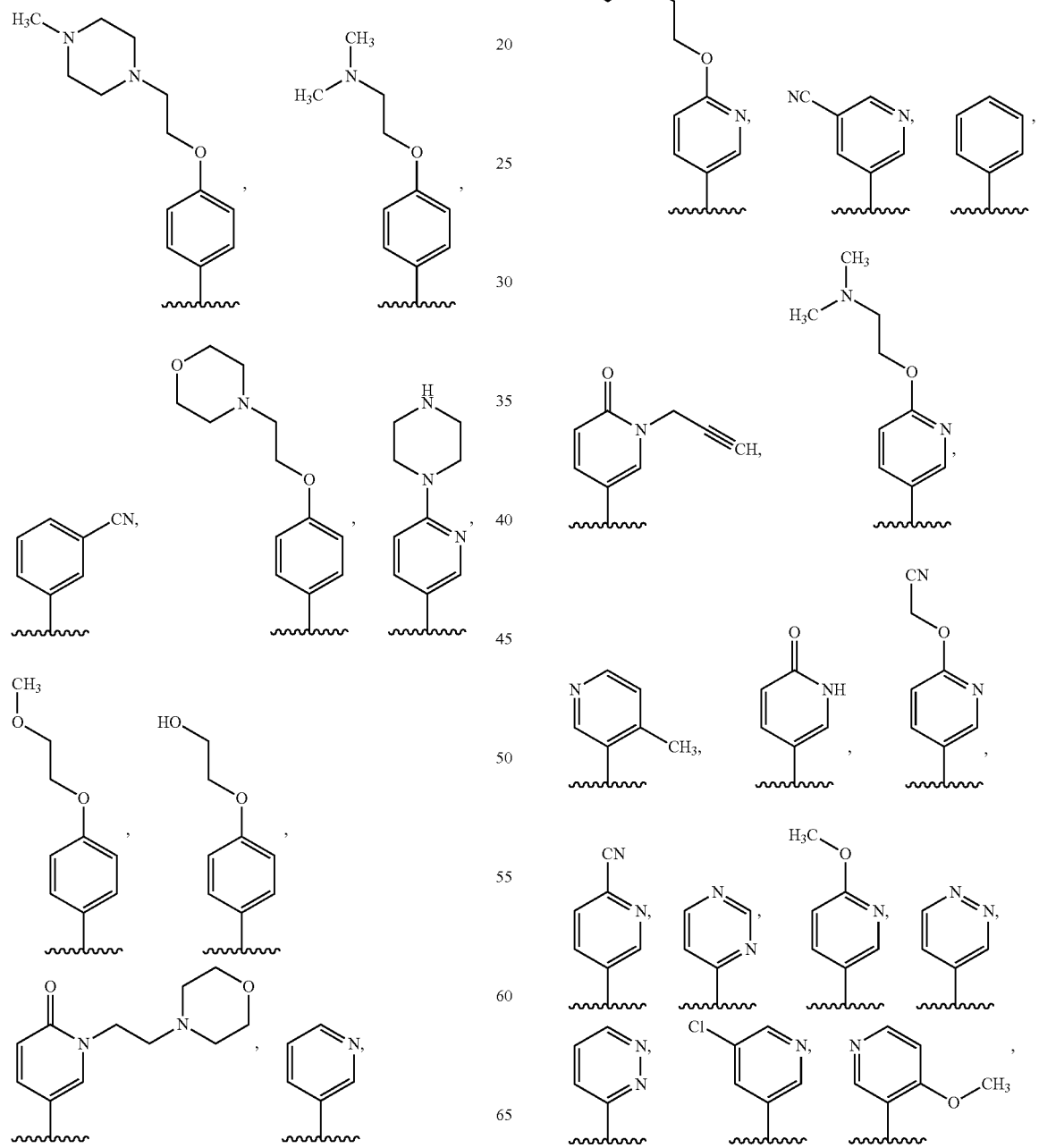

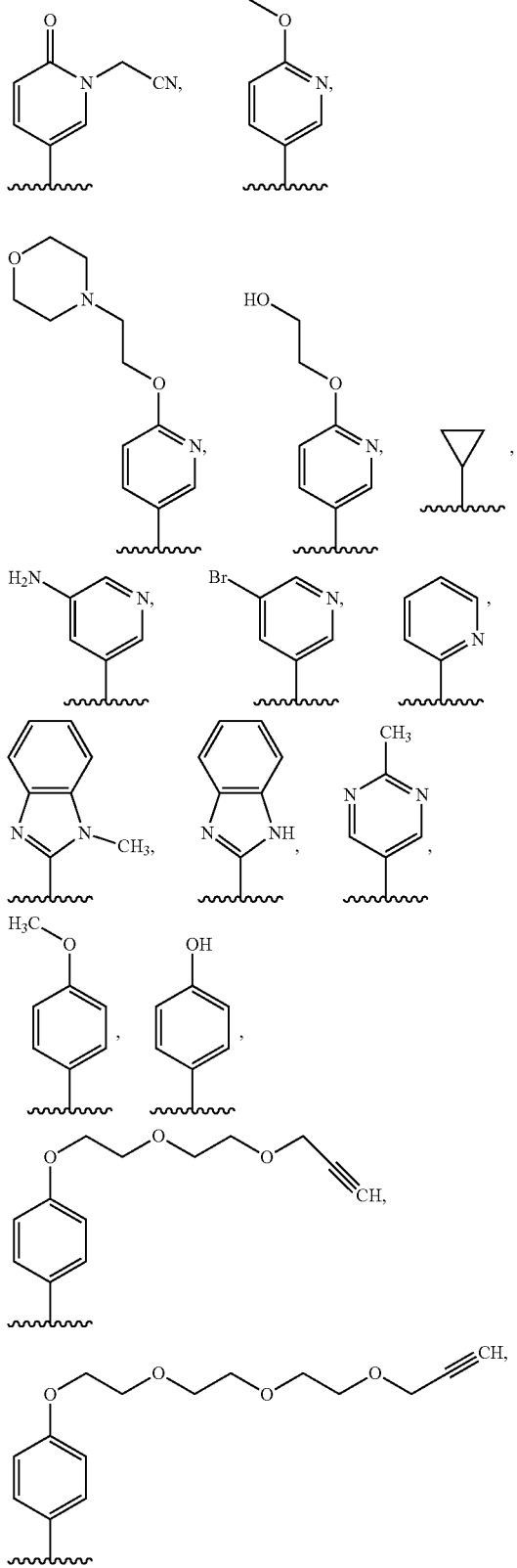

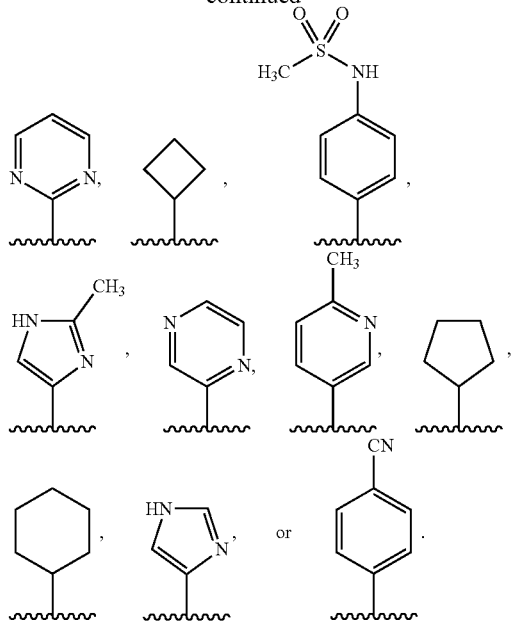

In some embodiments, Ring A is selected from those depicted in Table 1, below.

As defined above and described herein, $R^4$ is R or —C(O)OR.

In some embodiments, $R^4$ is R. In some embodiments, $R^4$ is methyl. In some embodiments, $R^4$ is —C(O)OR. In some embodiments, R is —C(O)OCH$_3$.

In some embodiments, $R^4$ is selected from those depicted in Table 1, below.

As defined above and described herein, each R is independently hydrogen or $C_{1-6}$ aliphatic optionally substituted with 1-3 fluorine atoms;

In some embodiments, each R is independently hydrogen. In some embodiments, each R is independently $C_{1-6}$ aliphatic optionally substituted with 1-3 fluorines. In some embodiments R is methyl.

In some embodiments, R is selected from those depicted in Table 1, below. As defined above and described herein, $R^5$ is hydrogen or CN, or: $R^5$ and $R^4$ are taken together with their intervening atoms to form a triazole ring; or $R^5$ and $R^3$ are taken together with their intervening atoms to form a triazole ring.

In some embodiments, $R^5$ is hydrogen. In some embodiments, $R^5$ is CN. In some embodiments, $R^5$ and $R^4$ are taken together with their intervening atoms to form a triazole ring. In some embodiments, $R^5$ and $R^3$ are taken together with their intervening atoms to form a triazole ring.

In some embodiments, $R^5$ is selected from those depicted in Table 1, below.

As defined above and described herein, $R^x$ and $R^y$ are each independently selected from hydrogen, halogen, optionally substituted $C_{1-6}$ aliphatic, or $R^x$ and $R^y$ are taken together with their intervening atoms to form an optionally substituted 5-6 membered saturated, partially unsaturated, or aromatic fused ring having 1-2 heteroatoms independently selected from nitrogen, oxygen, or sulfur.

In some embodiments, $R^x$ and $R^y$ are each independently selected from hydrogen, halogen, or optionally substituted $C_{1-6}$ aliphatic. In some embodiments $R^x$ and $R^y$ are each hydrogen. In some embodiments, $R^x$ and $R^y$ are taken together with their intervening atoms to form an optionally substituted 5-6 membered saturated, partially unsaturated, or aromatic fused ring having 1-2 heteroatoms independently selected from nitrogen, oxygen or sulfur.

In some embodiments, $R^x$ and $R^y$ taken together with their intervening atoms form

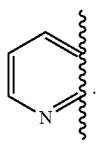

In some embodiments, $R^x$ and $R^y$ taken together with their intervening atoms form

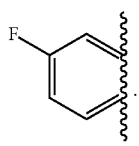

In some embodiments, $R^x$ and $R^y$ taken together with their intervening atoms form

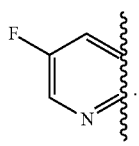

In some embodiments $R^x$ and $R^y$ taken together with their intervening atoms form

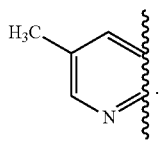

In some embodiments $R^x$ and $R^y$ taken together with their intervening atoms form

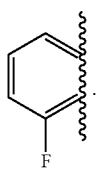

In some embodiments $R^x$ and $R^y$ taken together with their intervening atoms form

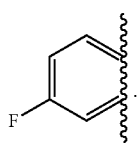

In some embodiments $R^x$ and $R^y$ taken together with their intervening atoms form

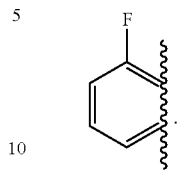

In some embodiments $R^x$ and $R^y$ taken together with their intervening atoms form

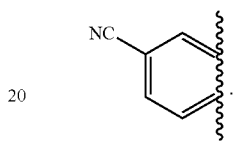

In some embodiments $R^x$ and $R^y$ taken together with their intervening atoms form

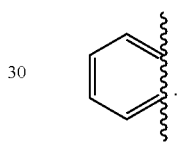

In some embodiments $R^x$ and $R^y$ taken together with their intervening atoms form

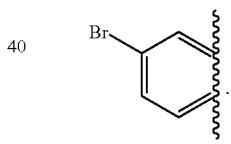

In some embodiments, $R^x$ and $R^y$ taken together with their intervening atoms form

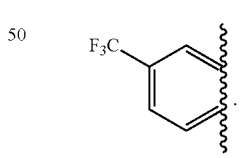

In some embodiments, $R^x$ and $R^y$ taken together with their intervening atoms form

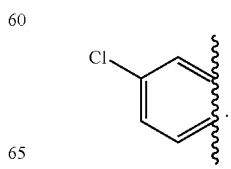

In some embodiments, $R^x$ and $R^y$ taken together with their intervening atoms form

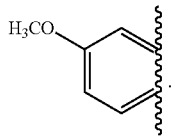

In some embodiments, $R^x$ and $R^y$ taken together with their intervening atoms form

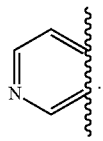

In some embodiments, $R^x$ and $R^y$ taken together with their intervening atoms form

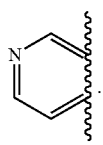

In some embodiments, $R^x$ and $R^y$ taken together with their intervening atoms form

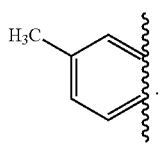

In some embodiments, $R^x$ and $R^y$ taken together with their intervening atoms form

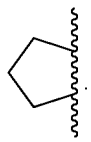

In some embodiments, $R^x$ and $R^y$ taken together with their intervening atoms is selected from those depicted in Table 1, below.

In certain embodiments, the present invention provides a compound of formula I-a or II-a:

I-a

II-a or a pharmaceutically acceptable salt thereof, wherein each of $R^1$, $R^2$, $R^4$, $R^5$, Ring A, $R^x$, and $R^y$ is as defined above and described in embodiments herein, both singly and in combination.

In some embodiments, the present invention provides a compound of formula III-a, III-b, III-c, III-d, III-e, III-f, III-g, III-h, IV-a, IV-b, IV-c, IV-d, IV-e, IV-f, IV-g or IV-h:

III-a

III-b

III-c

III-d

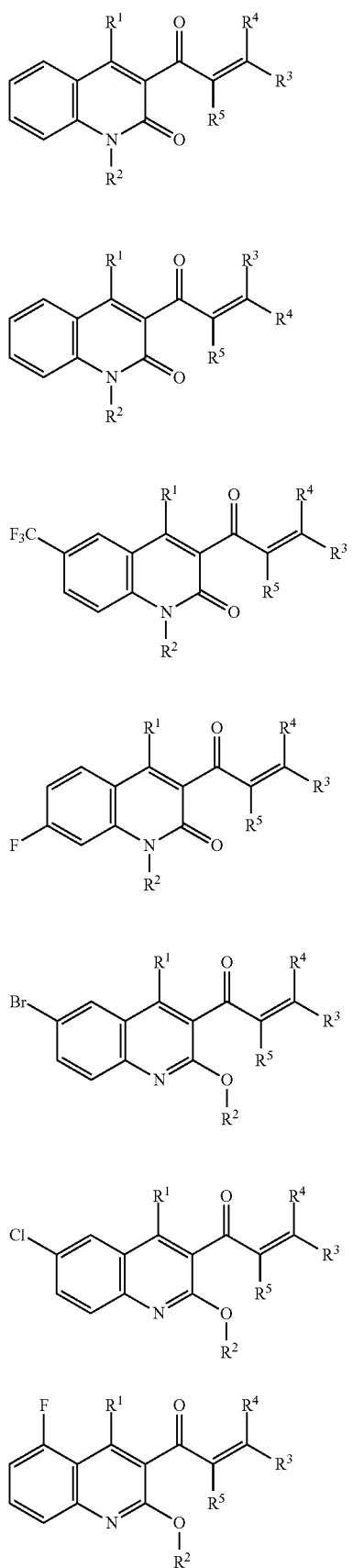
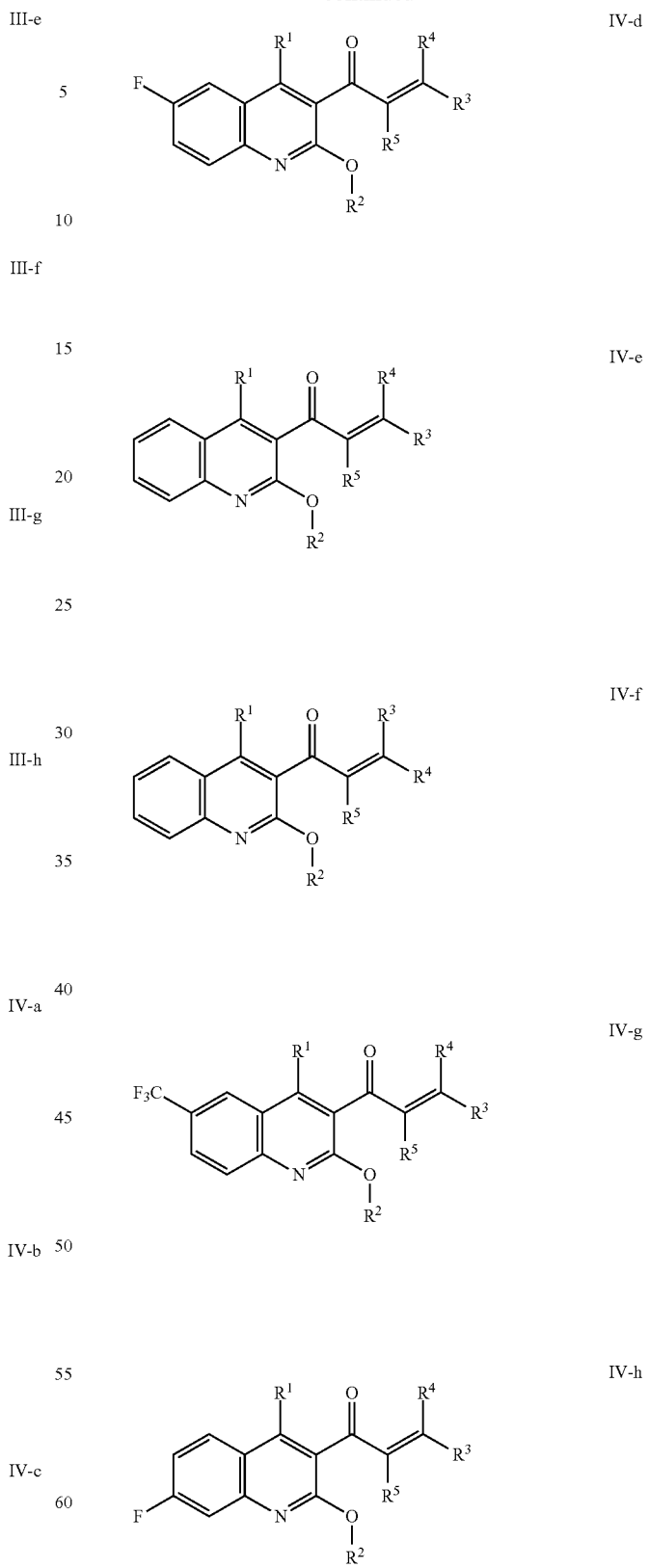
or a pharmaceutically acceptable salt thereof, wherein each of $R^1$, $R^2$, $R^3$, $R^4$, and $R^5$ is as defined above and described in embodiments herein, both singly and in combination.

In some embodiments, the compound of formula I is selected from those depicted below in Table 1.
TABLE 1
Exemplary Compounds of Formula I
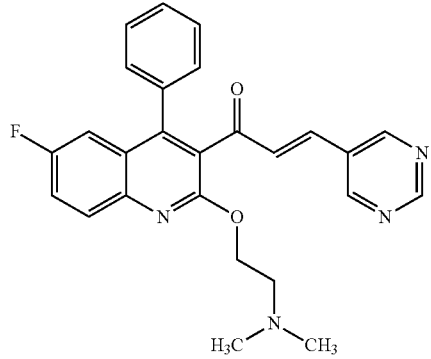 [SMILES: CN(C)CCOc1nc2ccc(F)cc2c(-c2ccccc2)c1C(=O)/C=C/c1cncnc1]
I-1
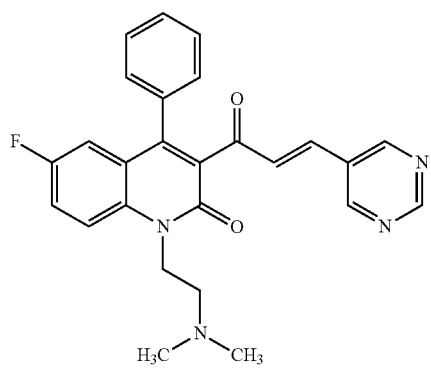 [SMILES: CN(C)CCn1c(=O)c(C(=O)/C=C/c2cncnc2)c(-c2ccccc2)c2cc(F)ccc21]
I-2
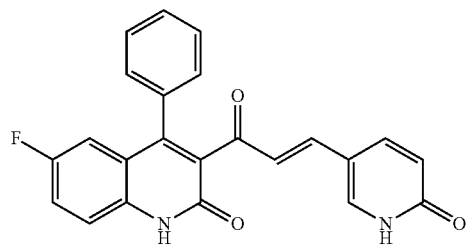 [SMILES: O=C(/C=C/c1ccc(=O)[nH]c1)c1c(-c2ccccc2)c2cc(F)ccc2[nH]c1=O]
I-3
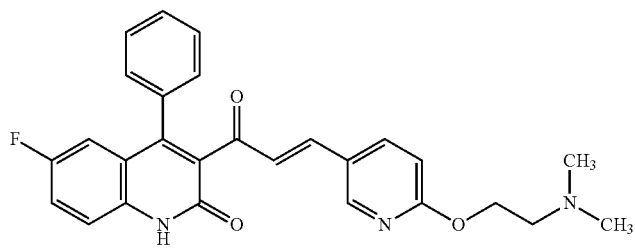 [SMILES: CN(C)CCOc1ccc(/C=C/C(=O)c2c(-c3ccccc3)c3cc(F)ccc3[nH]c2=O)cn1]
I-4
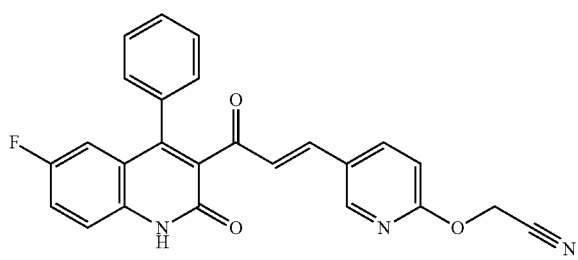 [SMILES: N#CCOc1ccc(/C=C/C(=O)c2c(-c3ccccc3)c3cc(F)ccc3[nH]c2=O)cn1]
I-5

TABLE 1-continued
Exemplary Compounds of Formula I
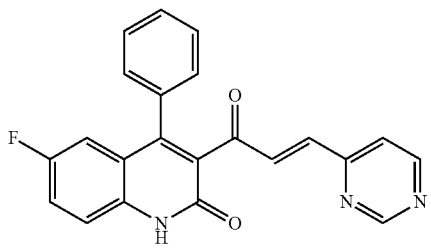 [SMILES: O=C(/C=C/c1ccncn1)c1c(-c2ccccc2)c2cc(F)ccc2[nH]c1=O]
I-6
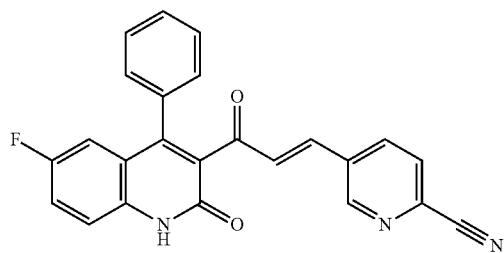 [SMILES: N#Cc1ccc(/C=C/C(=O)c2c(-c3ccccc3)c3cc(F)ccc3[nH]c2=O)cn1]
I-7
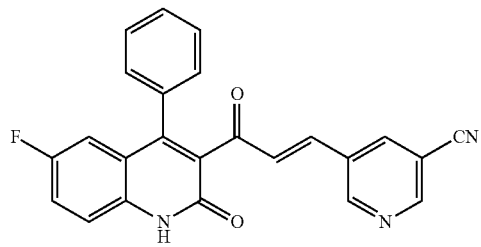 [SMILES: N#Cc1cncc(/C=C/C(=O)c2c(-c3ccccc3)c3cc(F)ccc3[nH]c2=O)c1]
I-8
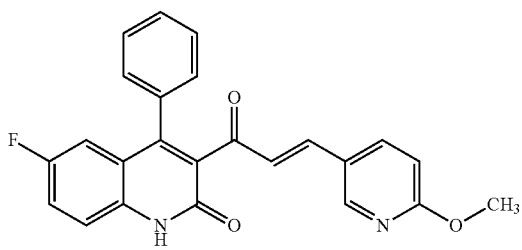 [SMILES: COc1ccc(/C=C/C(=O)c2c(-c3ccccc3)c3cc(F)ccc3[nH]c2=O)cn1]
I-9
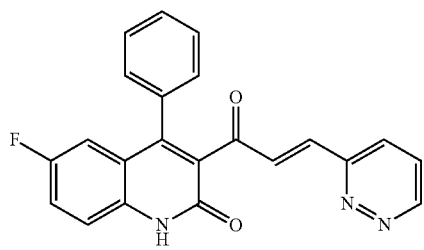 [SMILES: O=C(/C=C/c1cccnn1)c1c(-c2ccccc2)c2cc(F)ccc2[nH]c1=O]
I-10
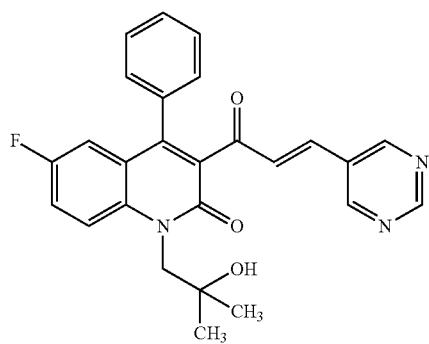 [SMILES: CC(C)(O)Cn1c(=O)c(C(=O)/C=C/c2cncnc2)c(-c2ccccc2)c2cc(F)ccc21]
I-11

TABLE 1-continued
Exemplary Compounds of Formula I
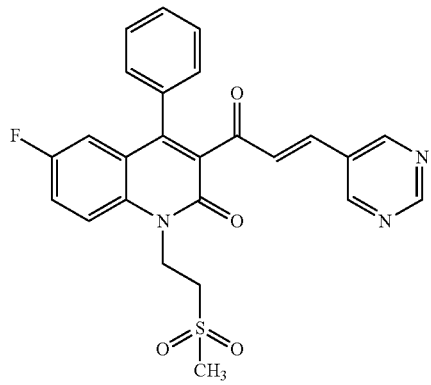 [SMILES: CS(=O)(=O)CCn1c(=O)c(C(=O)/C=C/c2cncnc2)c(-c2ccccc2)c2cc(F)ccc21]
I-12
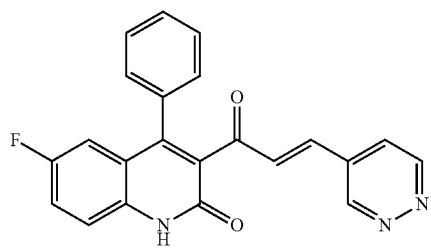 [SMILES: O=C(/C=C/c1ccnnc1)c1c(-c2ccccc2)c2cc(F)ccc2[nH]c1=O]
I-13
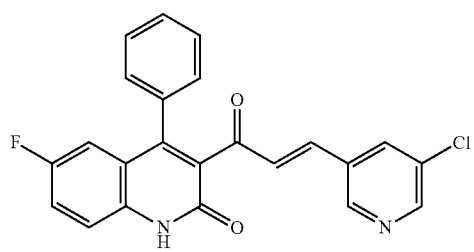 [SMILES: O=C(/C=C/c1cncc(Cl)c1)c1c(-c2ccccc2)c2cc(F)ccc2[nH]c1=O]
I-14
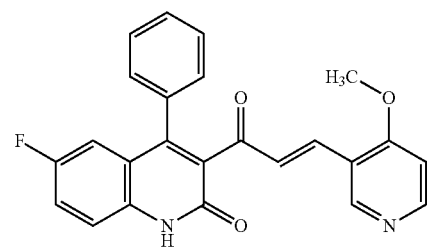 [SMILES: COc1ccncc1/C=C/C(=O)c1c(-c2ccccc2)c2cc(F)ccc2[nH]c1=O]
I-15
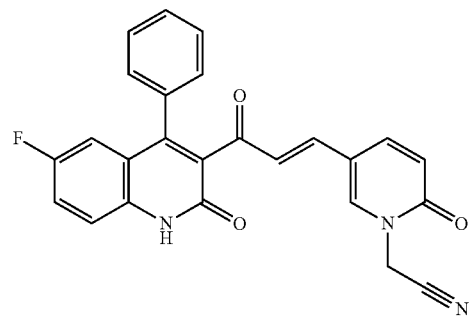 [SMILES: N#CCn1cc(/C=C/C(=O)c2c(-c3ccccc3)c3cc(F)ccc3[nH]c2=O)ccc1=O]
I-16

TABLE 1-continued
Exemplary Compounds of Formula I
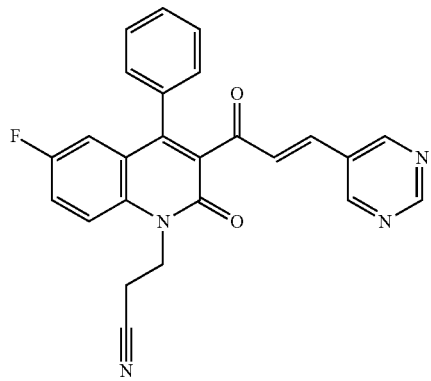 [SMILES: N#CCCn1c(=O)c(C(=O)/C=C/c2cncnc2)c(-c2ccccc2)c2cc(F)ccc21]
I-17
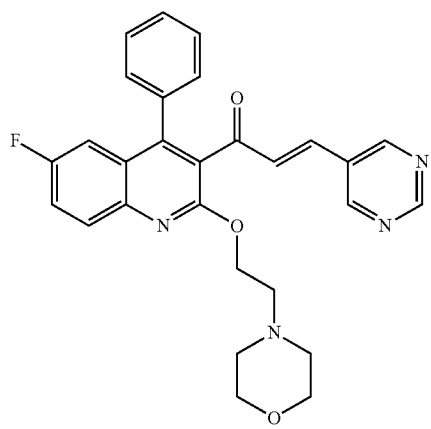 [SMILES: O=C(/C=C/c1cncnc1)c1c(OCCN2CCOCC2)nc2ccc(F)cc2c1-c1ccccc1]
I-18
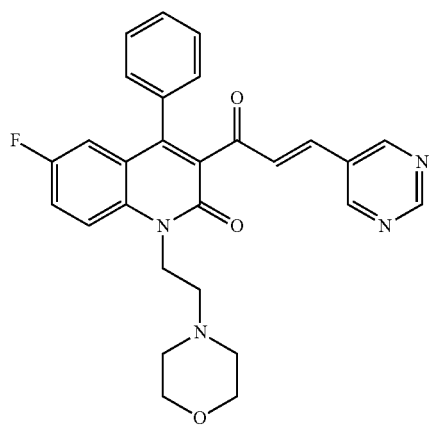 [SMILES: O=C(/C=C/c1cncnc1)c1c(-c2ccccc2)c2cc(F)ccc2n(CCN2CCOCC2)c1=O]
I-19
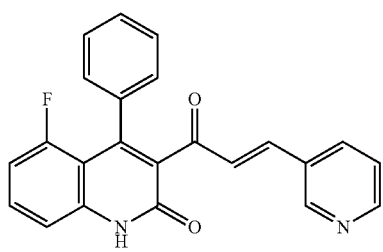 [SMILES: O=C(/C=C/c1cccnc1)c1c(-c2ccccc2)c2c(F)cccc2[nH]c1=O]
I-20

TABLE 1-continued
Exemplary Compounds of Formula I
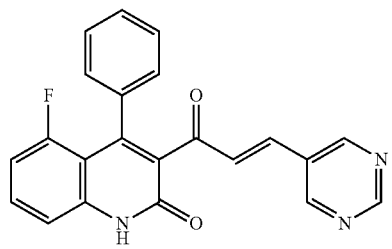 [SMILES: O=C(/C=C/c1cncnc1)c1c(-c2ccccc2)c2c(F)cccc2[nH]c1=O]
I-21
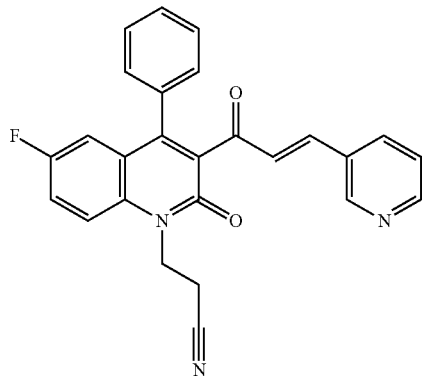
I-22
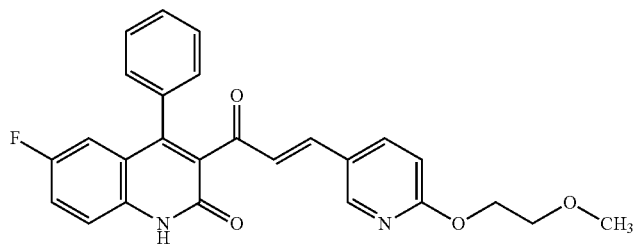 [SMILES: COCCOc1ccc(/C=C/C(=O)c2c(-c3ccccc3)c3cc(F)ccc3[nH]c2=O)cn1]
I-23
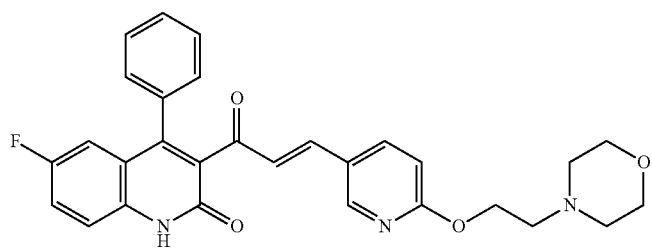 [SMILES: O=C(/C=C/c1ccc(OCCN2CCOCC2)nc1)c1c(-c2ccccc2)c2cc(F)ccc2[nH]c1=O]
I-24
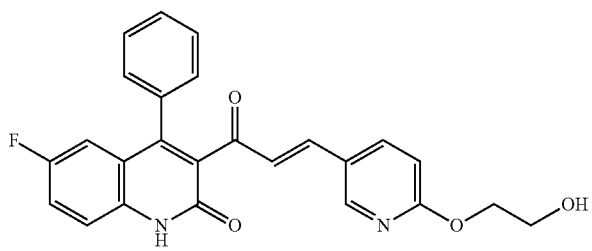 [SMILES: O=C(/C=C/c1ccc(OCCO)nc1)c1c(-c2ccccc2)c2cc(F)ccc2[nH]c1=O]
I-25

TABLE 1-continued
Exemplary Compounds of Formula I
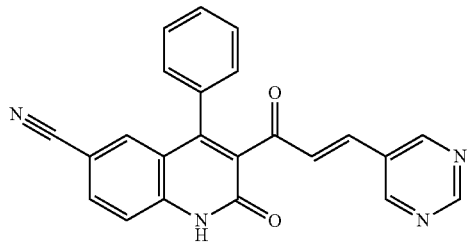 [SMILES: N#Cc1ccc2[nH]c(=O)c(C(=O)/C=C/c3cncnc3)c(-c3ccccc3)c2c1]
I-26
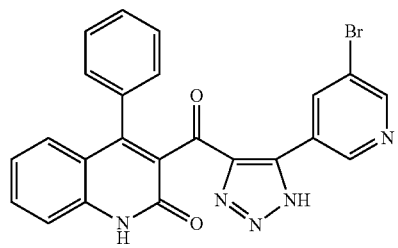 [SMILES: O=C(c1nn[nH]c1-c1cncc(Br)c1)c1c(-c2ccccc2)c2ccccc2[nH]c1=O]
I-27
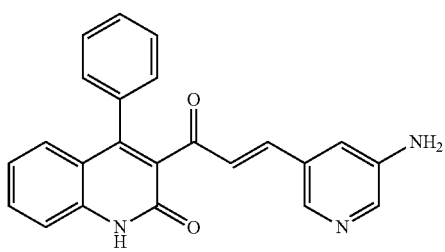 [SMILES: Nc1cncc(/C=C/C(=O)c2c(-c3ccccc3)c3ccccc3[nH]c2=O)c1]
I-28
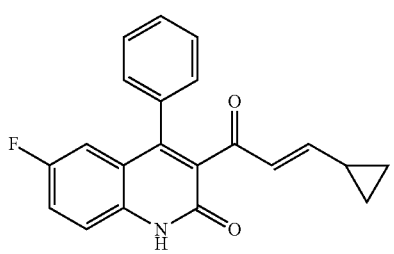 [SMILES: O=C(/C=C/C1CC1)c1c(-c2ccccc2)c2cc(F)ccc2[nH]c1=O]
I-29
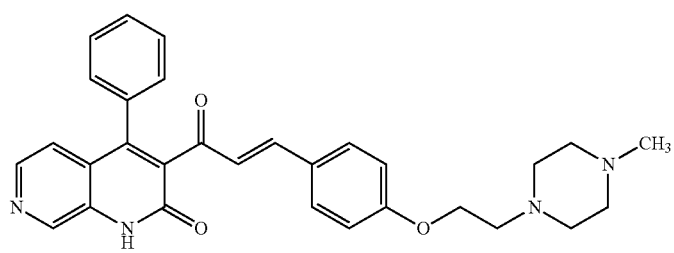 [SMILES: CN1CCN(CCOc2ccc(/C=C/C(=O)c3c(-c4ccccc4)c4ccncc4[nH]c3=O)cc2)CC1]
I-30
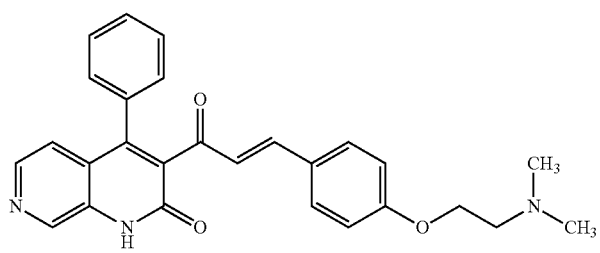 [SMILES: CN(C)CCOc1ccc(/C=C/C(=O)c2c(-c3ccccc3)c3ccncc3[nH]c2=O)cc1]
I-31

TABLE 1-continued
Exemplary Compounds of Formula I
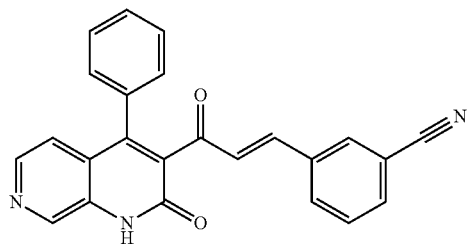 [SMILES: N#Cc1cccc(/C=C/C(=O)c2c(-c3ccccc3)c3ccncc3[nH]c2=O)c1]
I-32
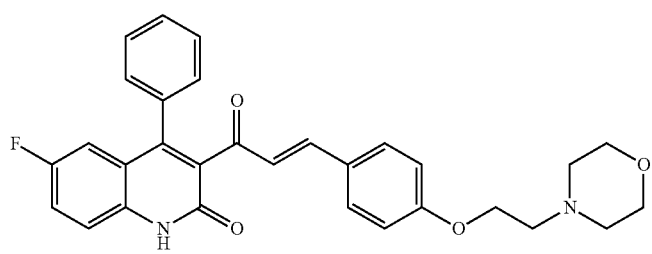 [SMILES: O=C(/C=C/c1ccc(OCCN2CCOCC2)cc1)c1c(-c2ccccc2)c2cc(F)ccc2[nH]c1=O]
I-33
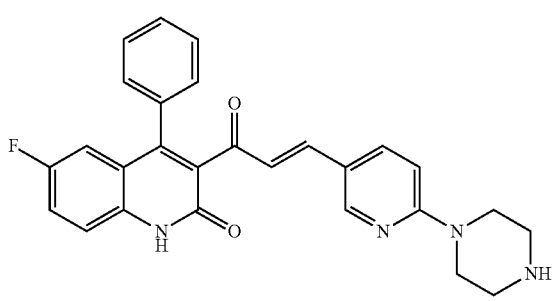 [SMILES: O=C(/C=C/c1ccc(N2CCNCC2)nc1)c1c(-c2ccccc2)c2cc(F)ccc2[nH]c1=O]
I-34
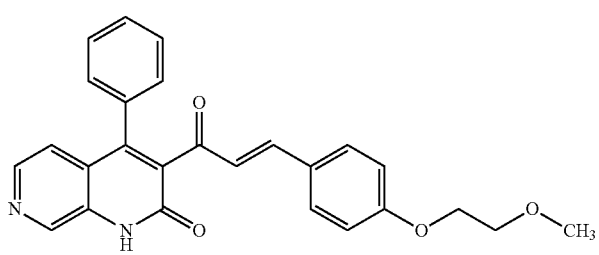 [SMILES: COCCOc1ccc(/C=C/C(=O)c2c(-c3ccccc3)c3ccncc3[nH]c2=O)cc1]
I-35
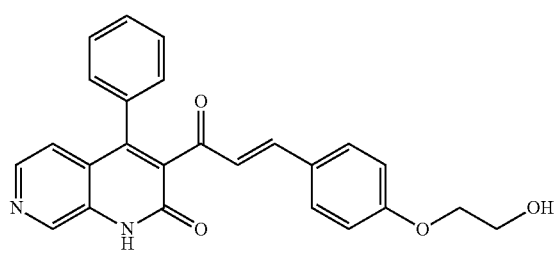 [SMILES: O=C(/C=C/c1ccc(OCCO)cc1)c1c(-c2ccccc2)c2ccncc2[nH]c1=O]
I-36
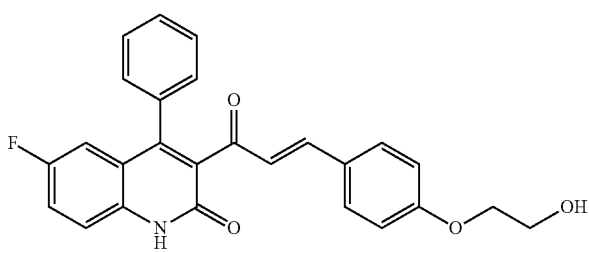 [SMILES: O=C(/C=C/c1ccc(OCCO)cc1)c1c(-c2ccccc2)c2cc(F)ccc2[nH]c1=O]
I-37

TABLE 1-continued
Exemplary Compounds of Formula I
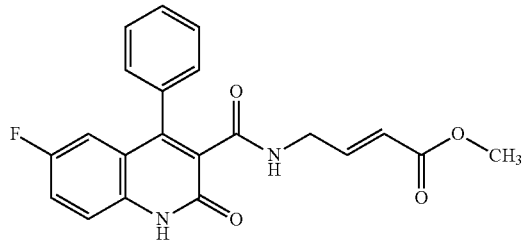 [SMILES: COC(=O)/C=C/CNC(=O)c1c(-c2ccccc2)c2cc(F)ccc2[nH]c1=O]
I-38
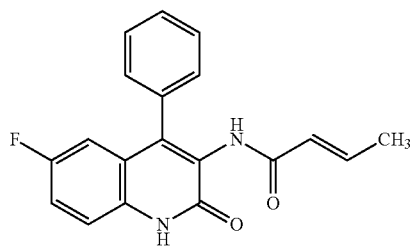 [SMILES: C/C=C/C(=O)Nc1c(-c2ccccc2)c2cc(F)ccc2[nH]c1=O]
I-40
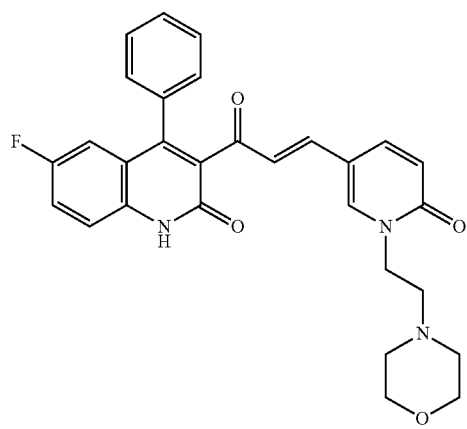 [SMILES: O=C(/C=C/c1ccc(=O)n(CCN2CCOCC2)c1)c1c(-c2ccccc2)c2cc(F)ccc2[nH]c1=O]
I-41
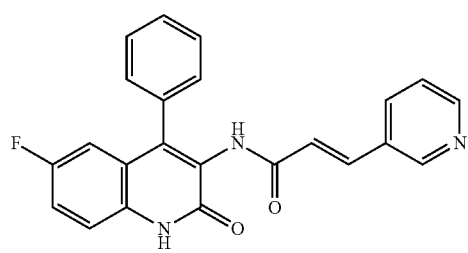 [SMILES: O=C(/C=C/c1cccnc1)Nc1c(-c2ccccc2)c2cc(F)ccc2[nH]c1=O]
I-42
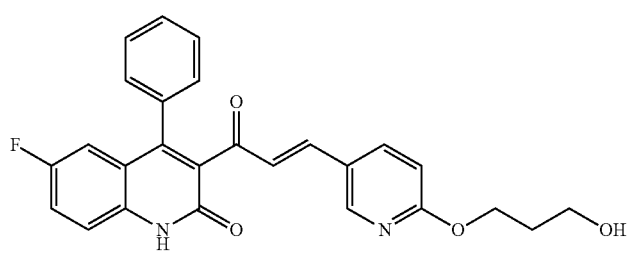 [SMILES: O=C(/C=C/c1ccc(OCCCO)nc1)c1c(-c2ccccc2)c2cc(F)ccc2[nH]c1=O]
I-43

TABLE 1-continued
Exemplary Compounds of Formula I
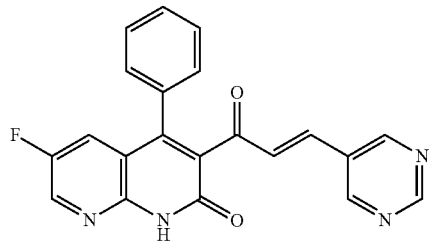 [SMILES: O=C(/C=C/c1cncnc1)c1c(-c2ccccc2)c2cc(F)cnc2[nH]c1=O]
I-44
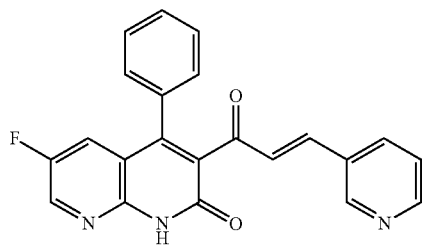 [SMILES: O=C(/C=C/c1cccnc1)c1c(-c2ccccc2)c2cc(F)cnc2[nH]c1=O]
I-45
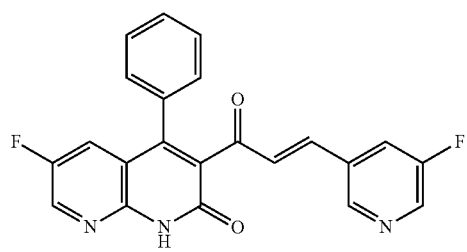 [SMILES: O=C(/C=C/c1cncc(F)c1)c1c(-c2ccccc2)c2cc(F)cnc2[nH]c1=O]
I-46
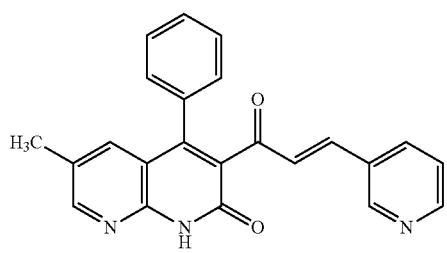 [SMILES: Cc1cnc2[nH]c(=O)c(C(=O)/C=C/c3cccnc3)c(-c3ccccc3)c2c1]
I-47
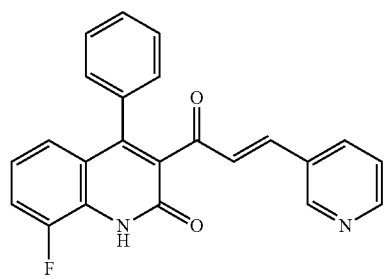 [SMILES: O=C(/C=C/c1cccnc1)c1c(-c2ccccc2)c2cccc(F)c2[nH]c1=O]
I-48
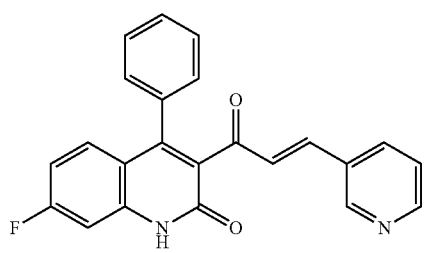 [SMILES: O=C(/C=C/c1cccnc1)c1c(-c2ccccc2)c2ccc(F)cc2[nH]c1=O]
I-49

TABLE 1-continued
Exemplary Compounds of Formula I
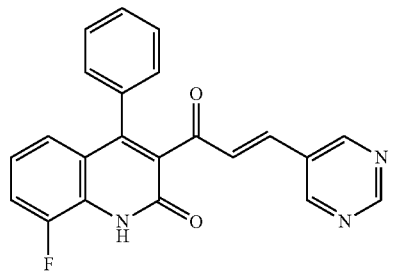 [SMILES: O=C(/C=C/c1cncnc1)c1c(-c2ccccc2)c2cccc(F)c2[nH]c1=O]
I-50
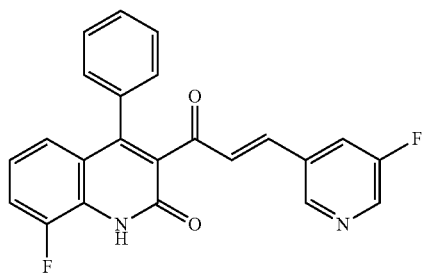 [SMILES: O=C(/C=C/c1cncc(F)c1)c1c(-c2ccccc2)c2cccc(F)c2[nH]c1=O]
I-51
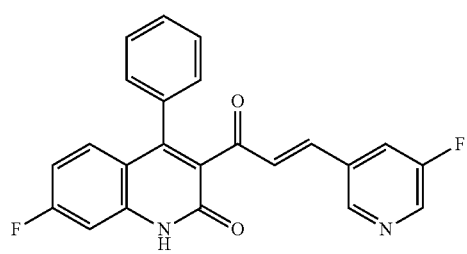 [SMILES: O=C(/C=C/c1cncc(F)c1)c1c(-c2ccccc2)c2ccc(F)cc2[nH]c1=O]
I-52
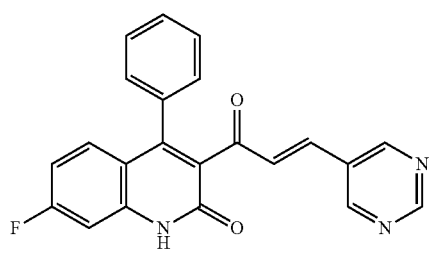 [SMILES: O=C(/C=C/c1cncnc1)c1c(-c2ccccc2)c2ccc(F)cc2[nH]c1=O]
I-53
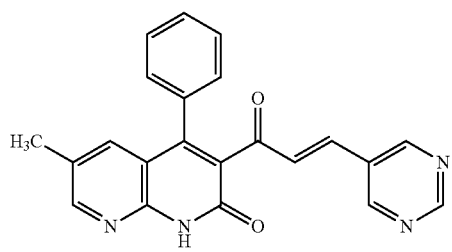 [SMILES: Cc1cnc2[nH]c(=O)c(C(=O)/C=C/c3cncnc3)c(-c3ccccc3)c2c1]
I-54
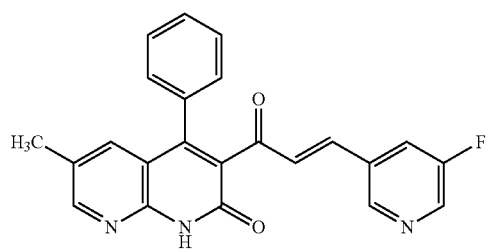 [SMILES: Cc1cnc2[nH]c(=O)c(C(=O)/C=C/c3cncc(F)c3)c(-c3ccccc3)c2c1]
I-55

TABLE 1-continued
Exemplary Compounds of Formula I
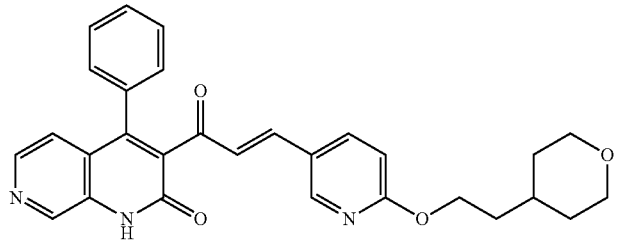 [SMILES: O=C(/C=C/c1ccc(OCCC2CCOCC2)nc1)c1c(-c2ccccc2)c2ccncc2[nH]c1=O]
I-56
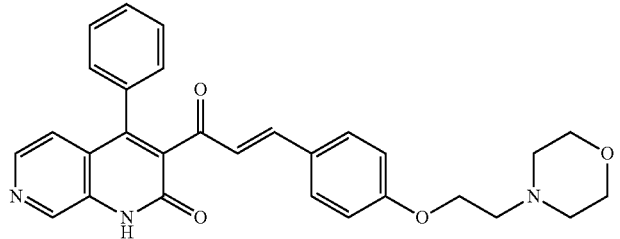 [SMILES: O=C(/C=C/c1ccc(OCCN2CCOCC2)cc1)c1c(-c2ccccc2)c2ccncc2[nH]c1=O]
I-57
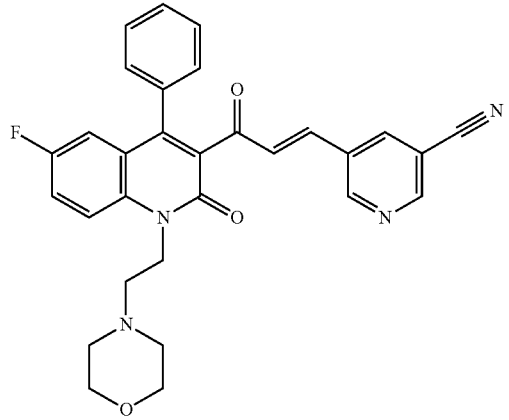 [SMILES: N#Cc1cncc(/C=C/C(=O)c2c(-c3ccccc3)c3cc(F)ccc3n(CCN3CCOCC3)c2=O)c1]
I-58
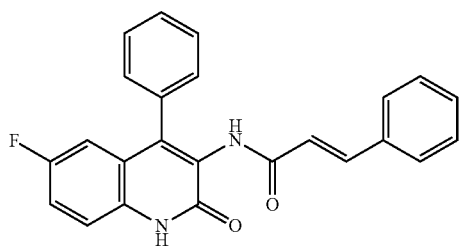 [SMILES: O=C(/C=C/c1ccccc1)Nc1c(-c2ccccc2)c2cc(F)ccc2[nH]c1=O]
I-59
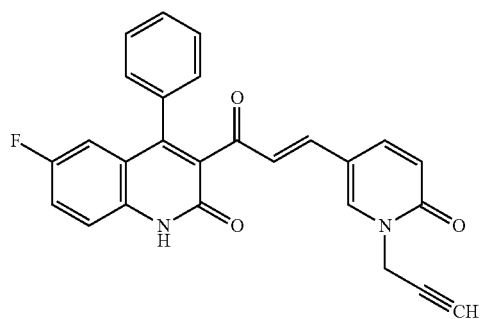 [SMILES: C#CCn1cc(/C=C/C(=O)c2c(-c3ccccc3)c3cc(F)ccc3[nH]c2=O)ccc1=O]
I-60

TABLE 1-continued
Exemplary Compounds of Formula I
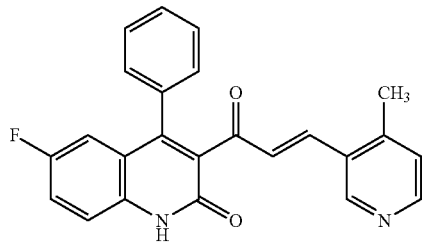 [SMILES: Cc1ccncc1/C=C/C(=O)c1c(-c2ccccc2)c2cc(F)ccc2[nH]c1=O] I-61
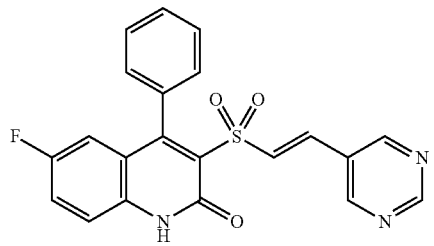 [SMILES: O=c1[nH]c2ccc(F)cc2c(-c2ccccc2)c1S(=O)(=O)/C=C/c1cncnc1] I-62
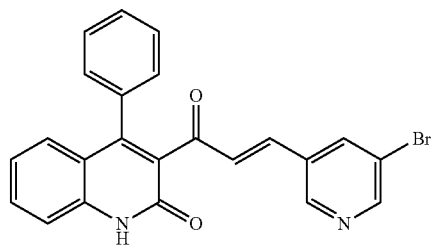 [SMILES: O=C(/C=C/c1cncc(Br)c1)c1c(-c2ccccc2)c2ccccc2[nH]c1=O] I-63
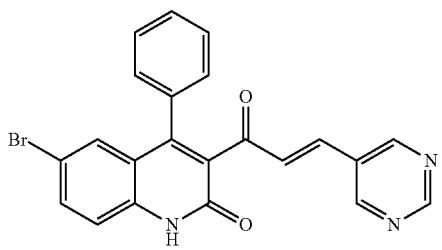 I-64
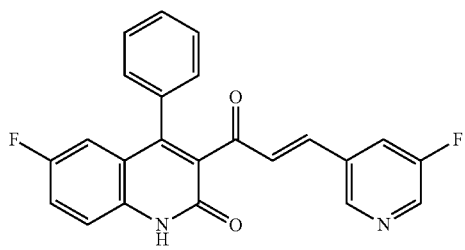 [SMILES: O=C(/C=C/c1cncc(F)c1)c1c(-c2ccccc2)c2cc(F)ccc2[nH]c1=O] I-65
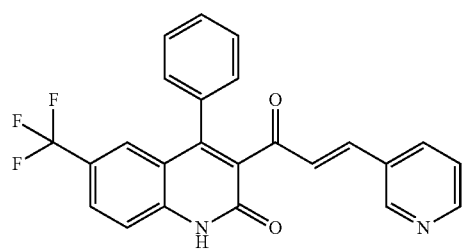 [SMILES: O=C(/C=C/c1cccnc1)c1c(-c2ccccc2)c2cc(C(F)(F)F)ccc2[nH]c1=O] I-66

TABLE 1-continued
Exemplary Compounds of Formula I
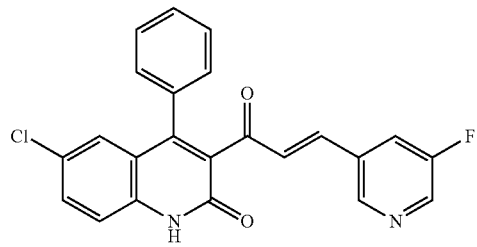 [SMILES: O=C(/C=C/c1cncc(F)c1)c1c(-c2ccccc2)c2cc(Cl)ccc2[nH]c1=O]
I-67
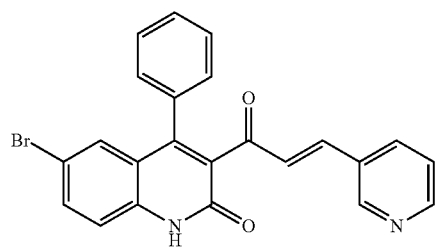 [SMILES: O=C(/C=C/c1cccnc1)c1c(-c2ccccc2)c2cc(Br)ccc2[nH]c1=O]
I-68
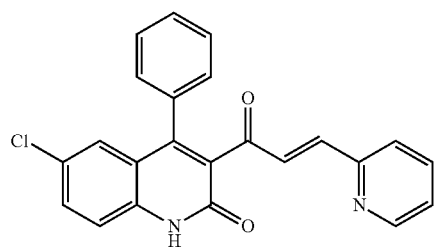 [SMILES: O=C(/C=C/c1ccccn1)c1c(-c2ccccc2)c2cc(Cl)ccc2[nH]c1=O]
I-69
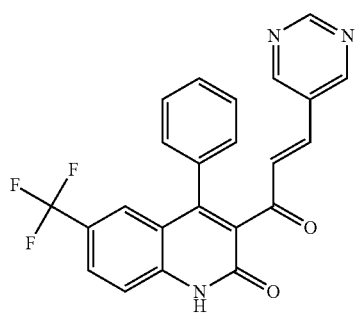 [SMILES: O=C(/C=C/c1cncnc1)c1c(-c2ccccc2)c2cc(C(F)(F)F)ccc2[nH]c1=O]
I-70
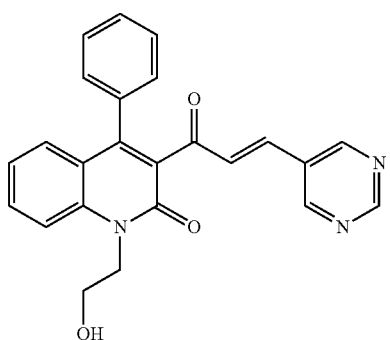 [SMILES: O=C(/C=C/c1cncnc1)c1c(-c2ccccc2)c2ccccc2n(CCO)c1=O]
I-71

TABLE 1-continued
Exemplary Compounds of Formula I
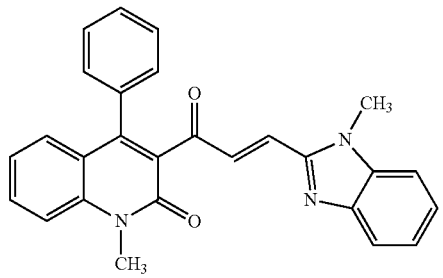 [SMILES: Cn1c(/C=C/C(=O)c2c(-c3ccccc3)c3ccccc3n(C)c2=O)nc2ccccc21]
I-72
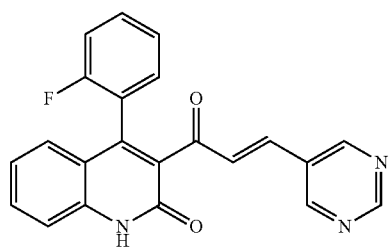 [SMILES: O=C(/C=C/c1cncnc1)c1c(-c2ccccc2F)c2ccccc2[nH]c1=O]
I-73
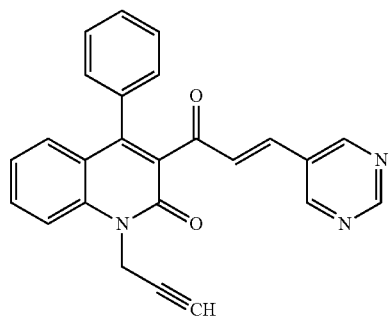 [SMILES: C#CCn1c(=O)c(C(=O)/C=C/c2cncnc2)c(-c2ccccc2)c2ccccc21]
I-74
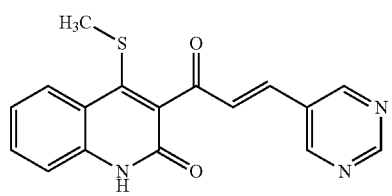 [SMILES: CSc1c(C(=O)/C=C/c2cncnc2)c(=O)[nH]c2ccccc12]
I-75
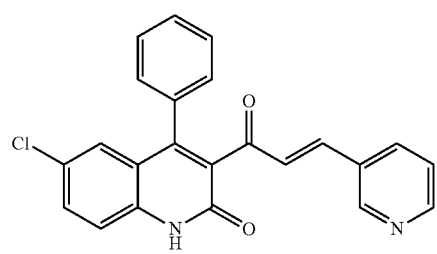 [SMILES: O=C(/C=C/c1cccnc1)c1c(-c2ccccc2)c2cc(Cl)ccc2[nH]c1=O]
I-76

TABLE 1-continued
Exemplary Compounds of Formula I
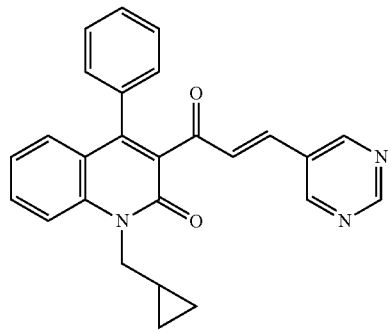 [SMILES: O=C(/C=C/c1cncnc1)c1c(-c2ccccc2)c2ccccc2n(CC2CC2)c1=O]
I-77
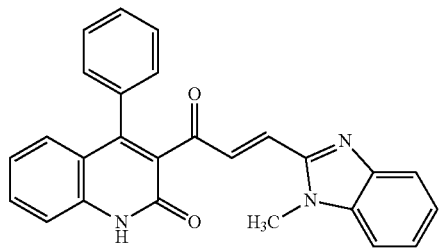 [SMILES: Cn1c(/C=C/C(=O)c2c(-c3ccccc3)c3ccccc3[nH]c2=O)nc2ccccc21]
I-78
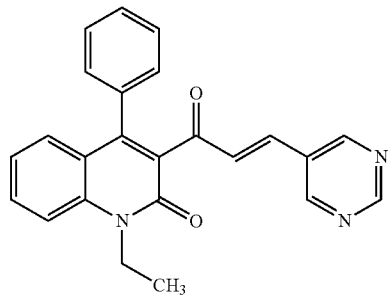 [SMILES: CCn1c(=O)c(C(=O)/C=C/c2cncnc2)c(-c2ccccc2)c2ccccc21]
I-79
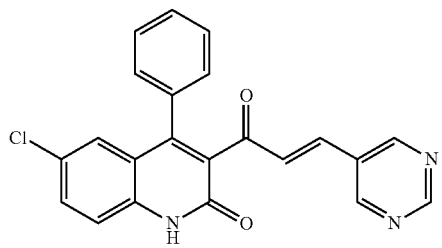 [SMILES: O=C(/C=C/c1cncnc1)c1c(-c2ccccc2)c2cc(Cl)ccc2[nH]c1=O]
I-80
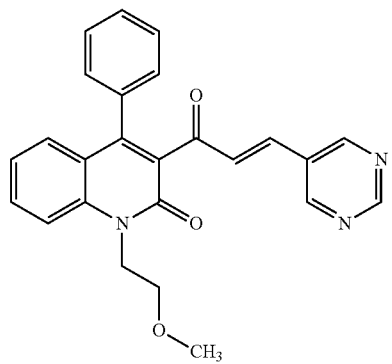 [SMILES: COCCn1c(=O)c(C(=O)/C=C/c2cncnc2)c(-c2ccccc2)c2ccccc21]
I-81

TABLE 1-continued
Exemplary Compounds of Formula I
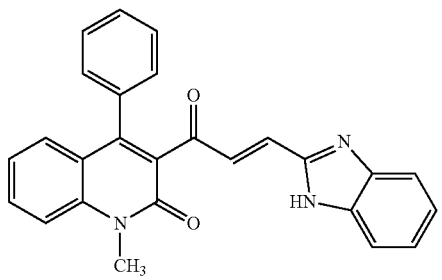 [SMILES: Cn1c(=O)c(C(=O)/C=C/c2nc3ccccc3[nH]2)c(-c2ccccc2)c2ccccc21]
I-82
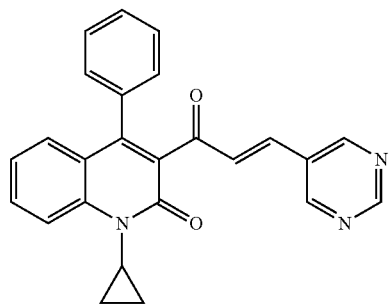 [SMILES: O=C(/C=C/c1cncnc1)c1c(-c2ccccc2)c2ccccc2n(C2CC2)c1=O]
I-83
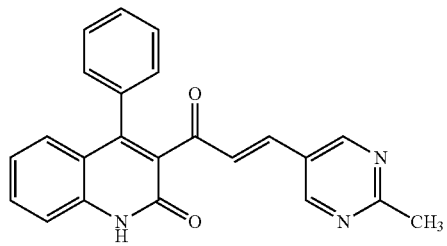 [SMILES: Cc1ncc(/C=C/C(=O)c2c(-c3ccccc3)c3ccccc3[nH]c2=O)cn1]
I-84
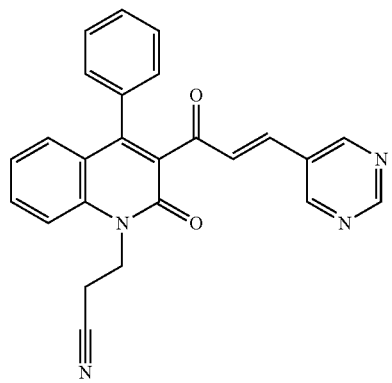 [SMILES: N#CCCn1c(=O)c(C(=O)/C=C/c2cncnc2)c(-c2ccccc2)c2ccccc21]
I-85
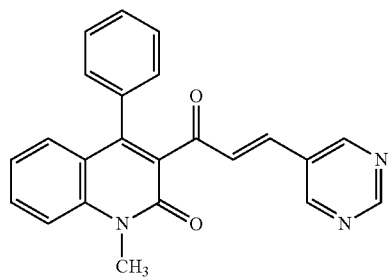 [SMILES: Cn1c(=O)c(C(=O)/C=C/c2cncnc2)c(-c2ccccc2)c2ccccc21]
I-86

TABLE 1-continued
Exemplary Compounds of Formula I
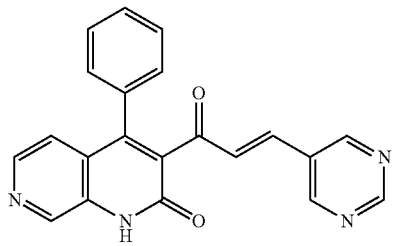 [SMILES: O=C(/C=C/c1cncnc1)c1c(-c2ccccc2)c2ccncc2[nH]c1=O]
I-87
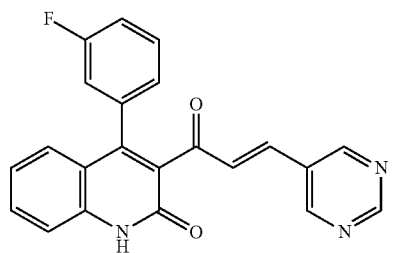 [SMILES: O=C(/C=C/c1cncnc1)c1c(-c2cccc(F)c2)c2ccccc2[nH]c1=O]
I-88
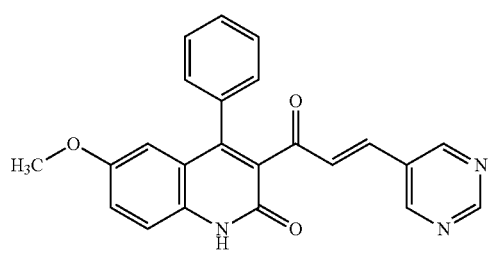 [SMILES: COc1ccc2[nH]c(=O)c(C(=O)/C=C/c3cncnc3)c(-c3ccccc3)c2c1]
I-89
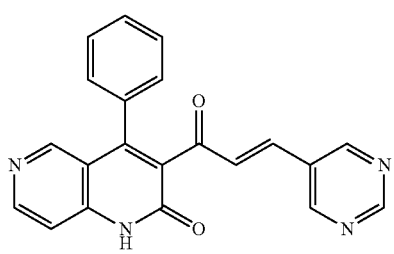 [SMILES: O=C(/C=C/c1cncnc1)c1c(-c2ccccc2)c2cnccc2[nH]c1=O]
I-90
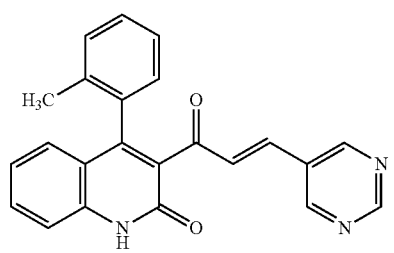 [SMILES: Cc1ccccc1-c1c(C(=O)/C=C/c2cncnc2)c(=O)[nH]c2ccccc12]
I-91
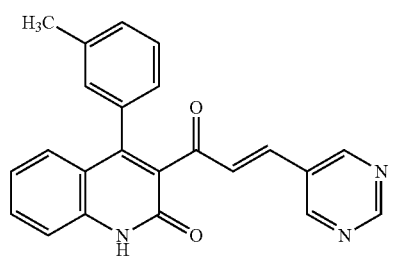 [SMILES: Cc1cccc(-c2c(C(=O)/C=C/c3cncnc3)c(=O)[nH]c3ccccc23)c1]
I-92

TABLE 1-continued
Exemplary Compounds of Formula I
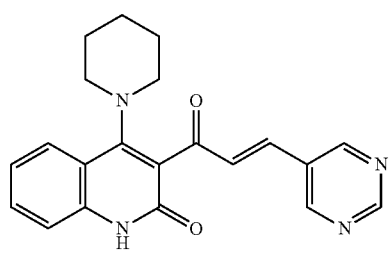 [SMILES: O=C(/C=C/c1cncnc1)c1c(N2CCCCC2)c2ccccc2[nH]c1=O]
I-93
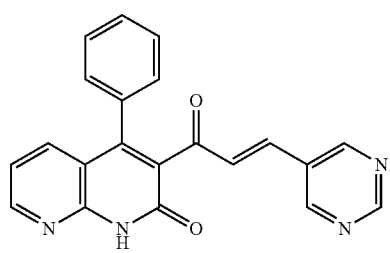 [SMILES: O=C(/C=C/c1cncnc1)c1c(-c2ccccc2)c2cccnc2[nH]c1=O]
I-94
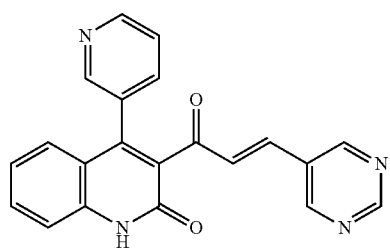 [SMILES: O=C(/C=C/c1cncnc1)c1c(-c2cccnc2)c2ccccc2[nH]c1=O]
I-95
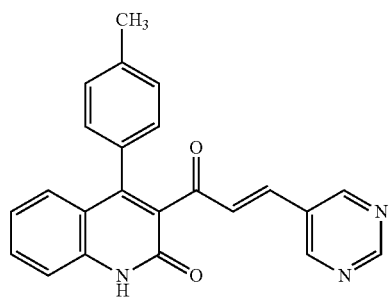 [SMILES: Cc1ccc(-c2c(C(=O)/C=C/c3cncnc3)c(=O)[nH]c3ccccc23)cc1]
I-96
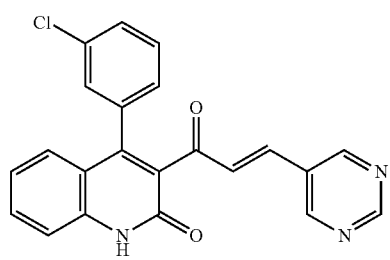
I-97

TABLE 1-continued
Exemplary Compounds of Formula I
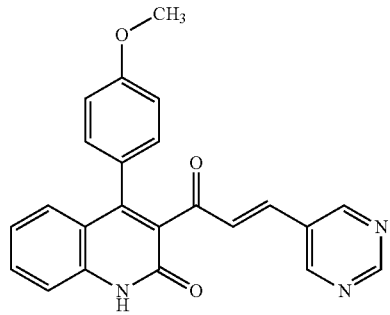 [SMILES: COc1ccc(-c2c(C(=O)/C=C/c3cncnc3)c(=O)[nH]c3ccccc23)cc1]
I-98
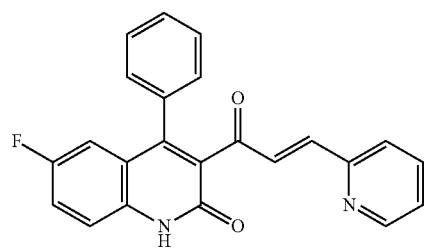 [SMILES: O=C(/C=C/c1ccccn1)c1c(-c2ccccc2)c2cc(F)ccc2[nH]c1=O]
I-99
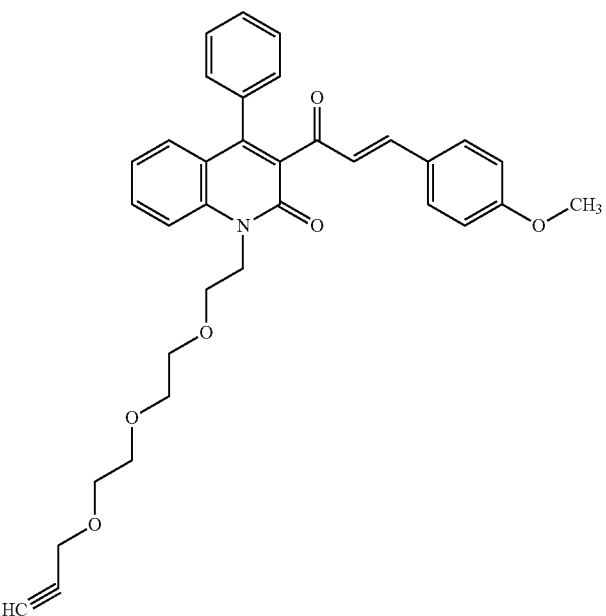 [SMILES: C#CCOCCOCCOCCn1c(=O)c(C(=O)/C=C/c2ccc(OC)cc2)c(-c2ccccc2)c2ccccc21]
I-100

TABLE 1-continued
Exemplary Compounds of Formula I
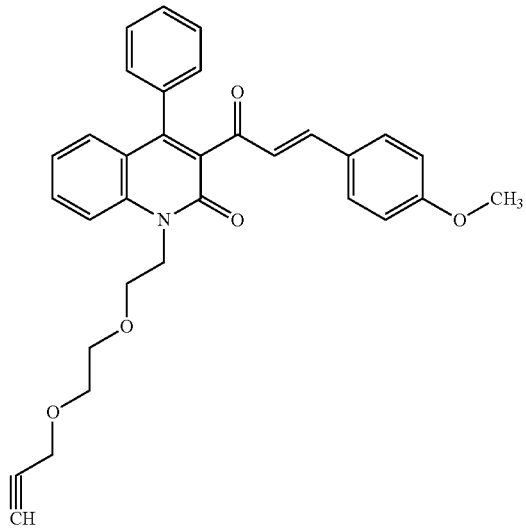 [SMILES: C#CCOCCOCCn1c(=O)c(C(=O)/C=C/c2ccc(OC)cc2)c(-c2ccccc2)c2ccccc21]
I-101
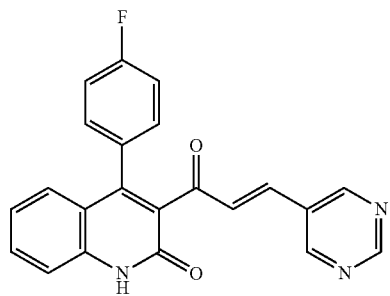 [SMILES: O=C(/C=C/c1cncnc1)c1c(-c2ccc(F)cc2)c2ccccc2[nH]c1=O]
I-102
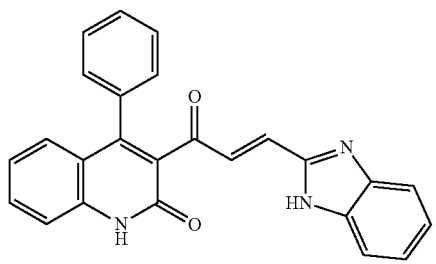 [SMILES: O=C(/C=C/c1nc2ccccc2[nH]1)c1c(-c2ccccc2)c2ccccc2[nH]c1=O]
I-103
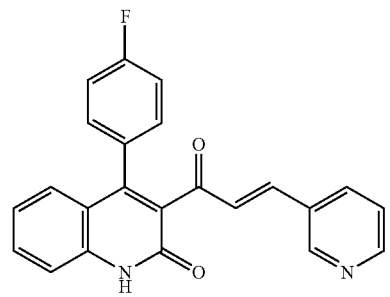 [SMILES: O=C(/C=C/c1cccnc1)c1c(-c2ccc(F)cc2)c2ccccc2[nH]c1=O]
I-104

TABLE 1-continued
Exemplary Compounds of Formula I
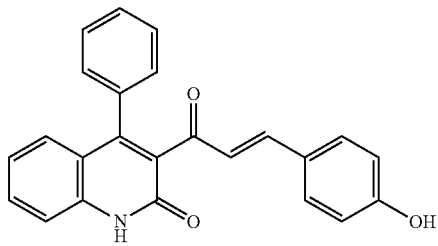 [SMILES: O=C(/C=C/c1ccc(O)cc1)c1c(-c2ccccc2)c2ccccc2[nH]c1=O]
I-105
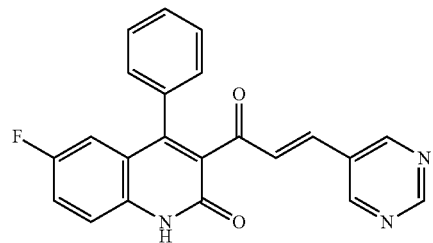 [SMILES: O=C(/C=C/c1cncnc1)c1c(-c2ccccc2)c2cc(F)ccc2[nH]c1=O]
I-106
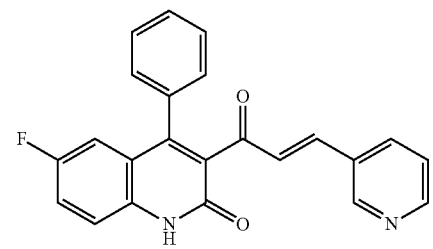 [SMILES: O=C(/C=C/c1cccnc1)c1c(-c2ccccc2)c2cc(F)ccc2[nH]c1=O]
I-107
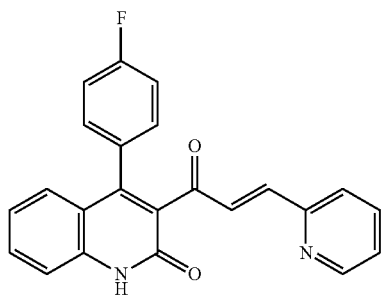 [SMILES: O=C(/C=C/c1ccccn1)c1c(-c2ccc(F)cc2)c2ccccc2[nH]c1=O]
I-108
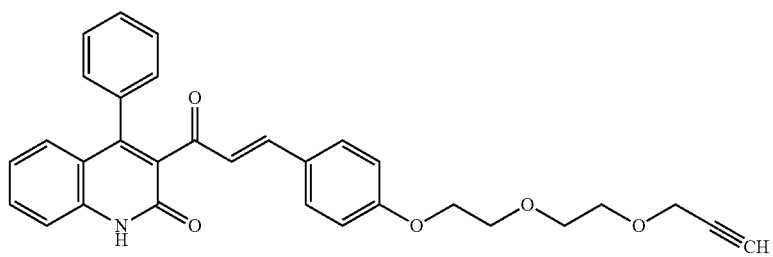 [SMILES: C#CCOCCOCCOc1ccc(/C=C/C(=O)c2c(-c3ccccc3)c3ccccc3[nH]c2=O)cc1]
I-109
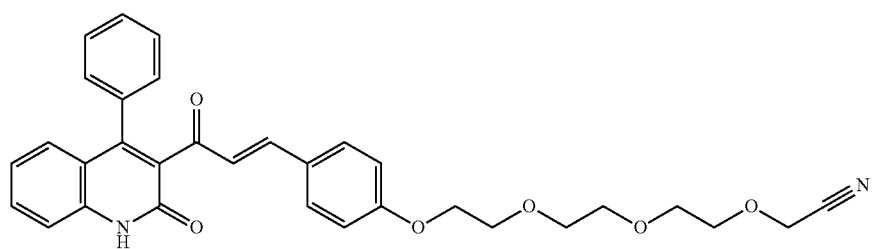 [SMILES: N#CCOCCOCCOCCOc1ccc(/C=C/C(=O)c2c(-c3ccccc3)c3ccccc3[nH]c2=O)cc1]
I-110

TABLE 1-continued
Exemplary Compounds of Formula I
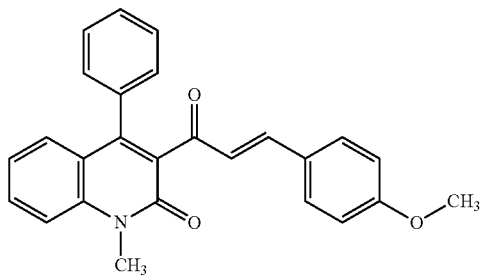 [SMILES: COc1ccc(/C=C/C(=O)c2c(-c3ccccc3)c3ccccc3n(C)c2=O)cc1] I-111
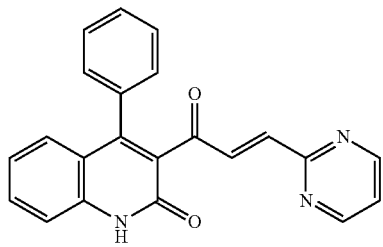 [SMILES: O=C(/C=C/c1ncccn1)c1c(-c2ccccc2)c2ccccc2[nH]c1=O] I-112
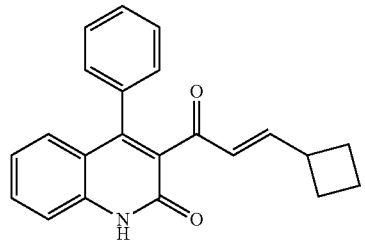 [SMILES: O=C(/C=C/C1CCC1)c1c(-c2ccccc2)c2ccccc2[nH]c1=O] I-113
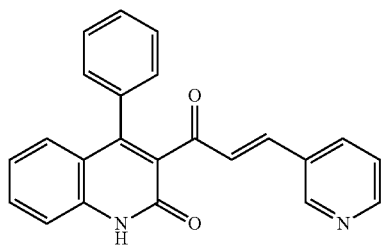 [SMILES: O=C(/C=C/c1cccnc1)c1c(-c2ccccc2)c2ccccc2[nH]c1=O] I-114
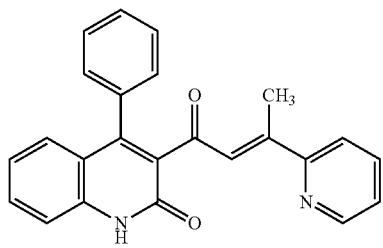 [SMILES: C/C(=C\C(=O)c1c(-c2ccccc2)c2ccccc2[nH]c1=O)c1ccccn1] I-115
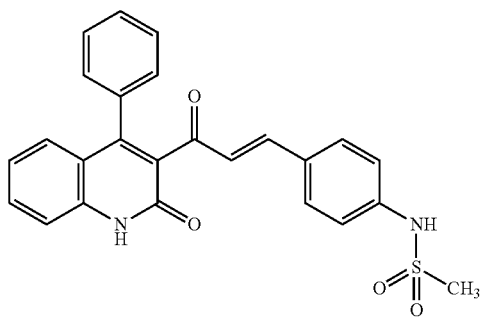 [SMILES: CS(=O)(=O)Nc1ccc(/C=C/C(=O)c2c(-c3ccccc3)c3ccccc3[nH]c2=O)cc1] I-116

TABLE 1-continued
Exemplary Compounds of Formula I
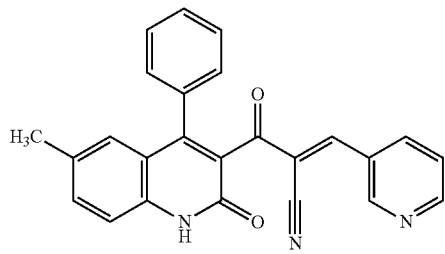 [SMILES: Cc1ccc2[nH]c(=O)c(C(=O)/C(C#N)=C/c3cccnc3)c(-c3ccccc3)c2c1]
I-117
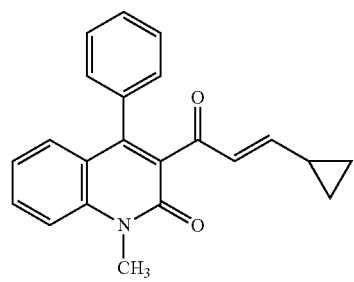 [SMILES: Cn1c(=O)c(C(=O)/C=C/C2CC2)c(-c2ccccc2)c2ccccc21]
I-118
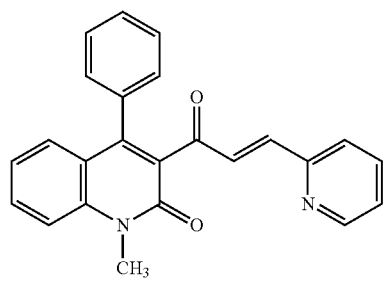 [SMILES: Cn1c(=O)c(C(=O)/C=C/c2ccccn2)c(-c2ccccc2)c2ccccc21]
I-119
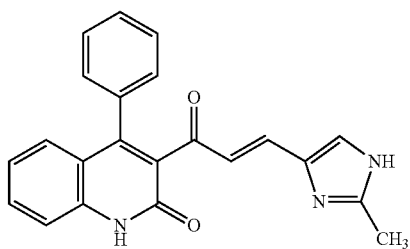 [SMILES: Cc1nc(/C=C/C(=O)c2c(-c3ccccc3)c3ccccc3[nH]c2=O)c[nH]1]
I-120
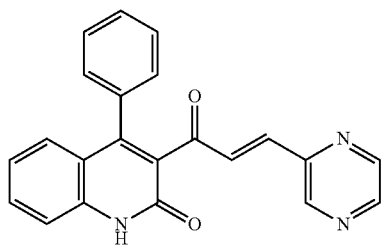 [SMILES: O=C(/C=C/c1cnccn1)c1c(-c2ccccc2)c2ccccc2[nH]c1=O]
I-121
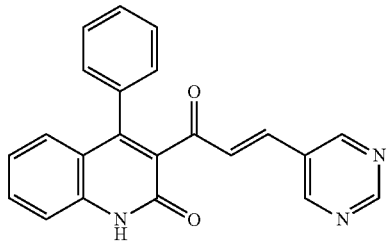 [SMILES: O=C(/C=C/c1cncnc1)c1c(-c2ccccc2)c2ccccc2[nH]c1=O]
I-122

TABLE 1-continued
Exemplary Compounds of Formula I
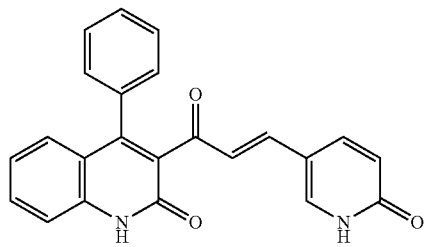 [SMILES: O=C(/C=C/c1ccc(=O)[nH]c1)c1c(-c2ccccc2)c2ccccc2[nH]c1=O] I-123
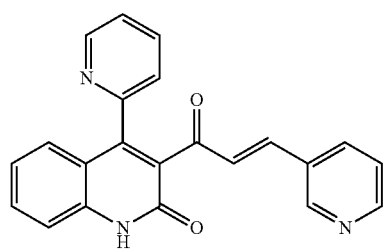 [SMILES: O=C(/C=C/c1cccnc1)c1c(-c2ccccn2)c2ccccc2[nH]c1=O] I-124
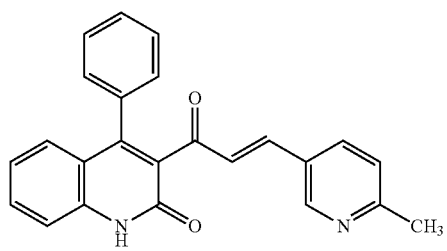 [SMILES: Cc1ccc(/C=C/C(=O)c2c(-c3ccccc3)c3ccccc3[nH]c2=O)cn1] I-125
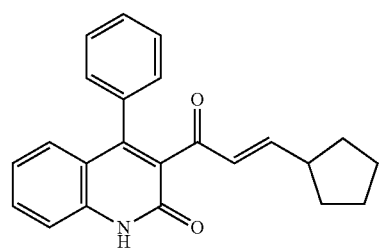 [SMILES: O=C(/C=C/C1CCCC1)c1c(-c2ccccc2)c2ccccc2[nH]c1=O] I-126
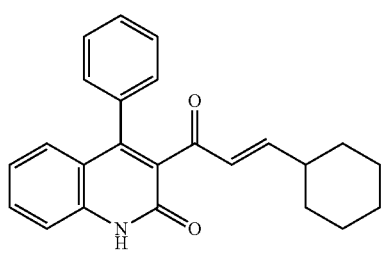 [SMILES: O=C(/C=C/C1CCCCC1)c1c(-c2ccccc2)c2ccccc2[nH]c1=O] I-127
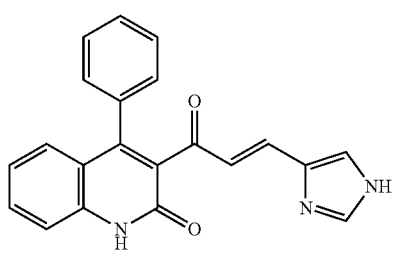 [SMILES: O=C(/C=C/c1c[nH]cn1)c1c(-c2ccccc2)c2ccccc2[nH]c1=O] I-128

TABLE 1-continued
Exemplary Compounds of Formula I
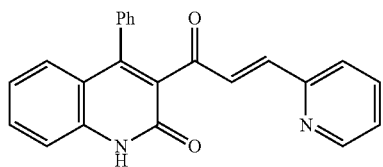 [SMILES: O=C(/C=C/c1ccccn1)c1c(-c2ccccc2)c2ccccc2[nH]c1=O] I-129
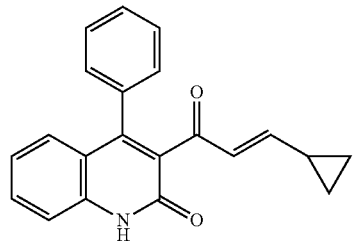 [SMILES: O=C(/C=C/C1CC1)c1c(-c2ccccc2)c2ccccc2[nH]c1=O] I-130
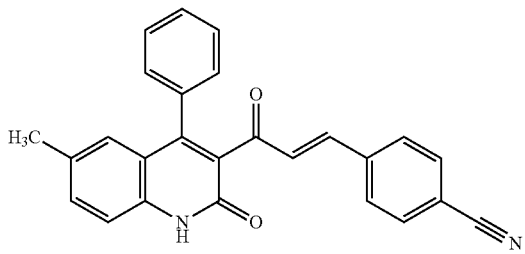 [SMILES: Cc1ccc2[nH]c(=O)c(C(=O)/C=C/c3ccc(C#N)cc3)c(-c3ccccc3)c2c1] I-131
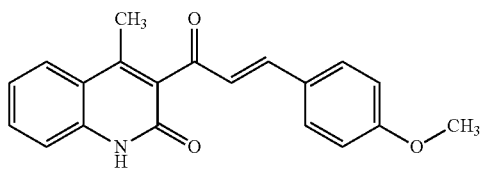 [SMILES: COc1ccc(/C=C/C(=O)c2c(C)c3ccccc3[nH]c2=O)cc1] I-132
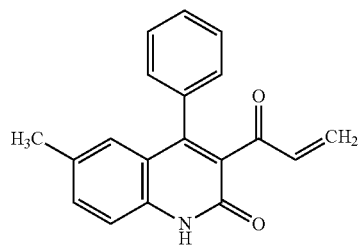 [SMILES: C=CC(=O)c1c(-c2ccccc2)c2cc(C)ccc2[nH]c1=O] I-133
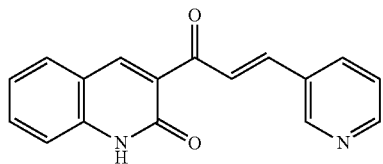 [SMILES: O=C(/C=C/c1cccnc1)c1cc2ccccc2[nH]c1=O] I-134
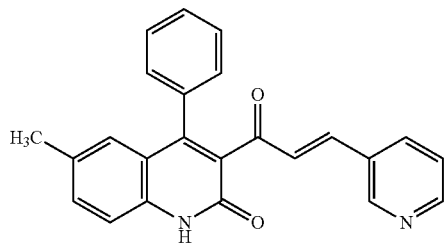 [SMILES: Cc1ccc2[nH]c(=O)c(C(=O)/C=C/c3cccnc3)c(-c3ccccc3)c2c1] I-135

TABLE 1-continued
Exemplary Compounds of Formula I
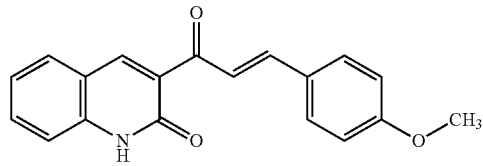 [SMILES: COc1ccc(/C=C/C(=O)c2cc3ccccc3[nH]c2=O)cc1]
I-136
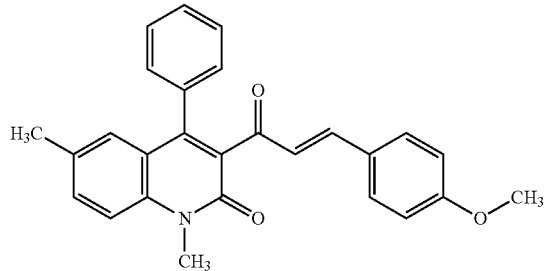
I-137
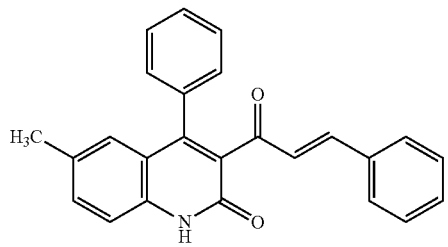 [SMILES: Cc1ccc2[nH]c(=O)c(C(=O)/C=C/c3ccccc3)c(-c3ccccc3)c2c1]
I-138
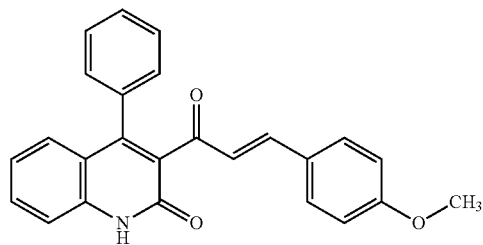 [SMILES: COc1ccc(/C=C/C(=O)c2c(-c3ccccc3)c3ccccc3[nH]c2=O)cc1]
I-139
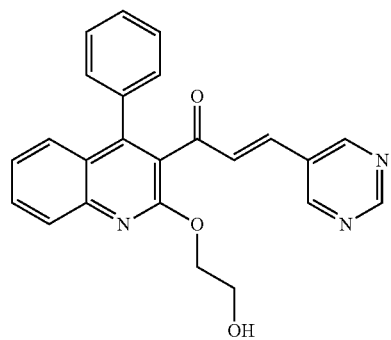 [SMILES: O=C(/C=C/c1cncnc1)c1c(OCCO)nc2ccccc2c1-c1ccccc1]
I-140

TABLE 1-continued
Exemplary Compounds of Formula I
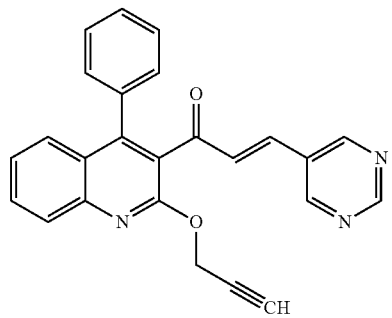 [SMILES: C#CCOc1nc2ccccc2c(-c2ccccc2)c1C(=O)/C=C/c1cncnc1]
I-141
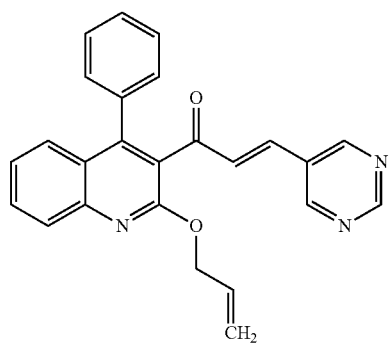 [SMILES: C=CCOc1nc2ccccc2c(-c2ccccc2)c1C(=O)/C=C/c1cncnc1]
I-142
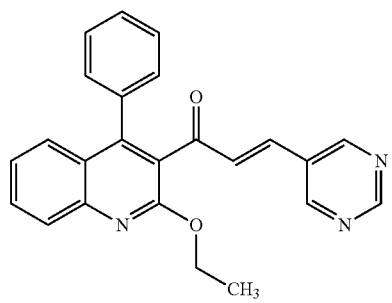 [SMILES: CCOc1nc2ccccc2c(-c2ccccc2)c1C(=O)/C=C/c1cncnc1]
I-143
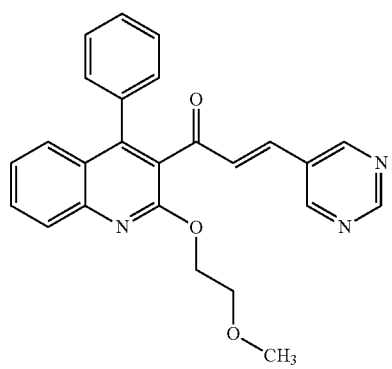 [SMILES: COCCOc1nc2ccccc2c(-c2ccccc2)c1C(=O)/C=C/c1cncnc1]
I-144
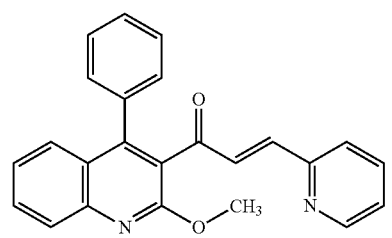 [SMILES: COc1nc2ccccc2c(-c2ccccc2)c1C(=O)/C=C/c1ccccn1]
I-145

TABLE 1-continued
Exemplary Compounds of Formula I
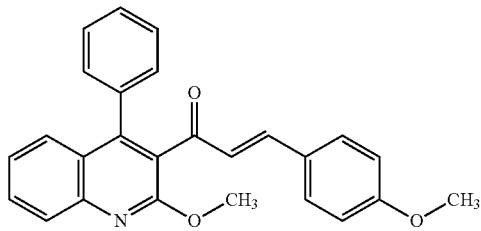 [SMILES: COc1ccc(/C=C/C(=O)c2c(OC)nc3ccccc3c2-c2ccccc2)cc1]
I-146
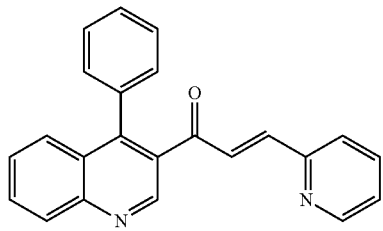 [SMILES: O=C(/C=C/c1ccccn1)c1cnc2ccccc2c1-c1ccccc1]
I-147
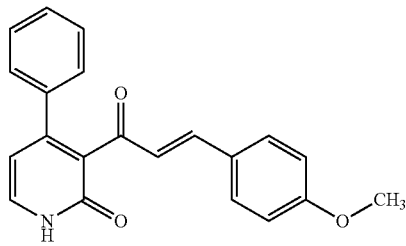 [SMILES: COc1ccc(/C=C/C(=O)c2c(-c3ccccc3)cc[nH]c2=O)cc1]
I-148
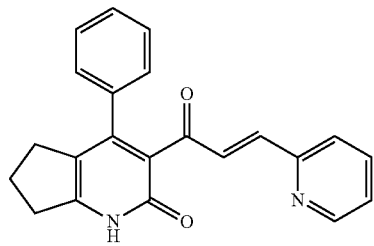 [SMILES: O=C(/C=C/c1ccccn1)c1c(-c2ccccc2)c2c([nH]c1=O)CCC2]
I-149
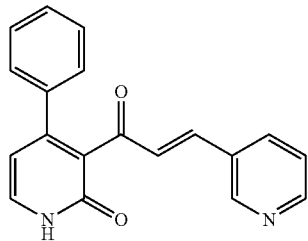 [SMILES: O=C(/C=C/c1cccnc1)c1c(-c2ccccc2)cc[nH]c1=O]
I-150
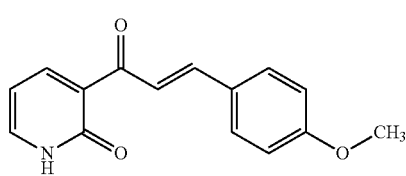 [SMILES: COc1ccc(/C=C/C(=O)c2ccc[nH]c2=O)cc1]
I-151

TABLE 2
| Compounds | |
|---|---|
| 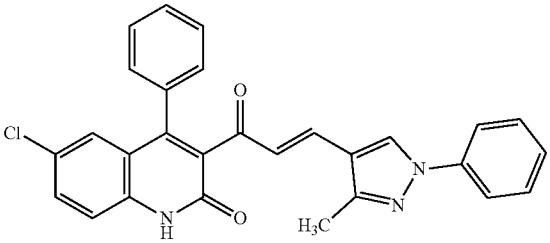 [SMILES: Cc1nn(-c2ccccc2)cc1/C=C/C(=O)c1c(-c2ccccc2)c2cc(Cl)ccc2[nH]c1=O] | 2-1 |
| 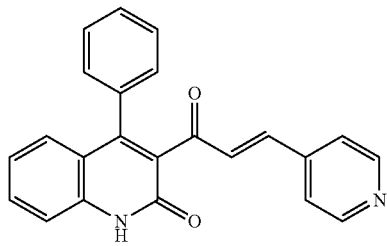 [SMILES: O=C(/C=C/c1ccncc1)c1c(-c2ccccc2)c2ccccc2[nH]c1=O] | 2-2 |
| 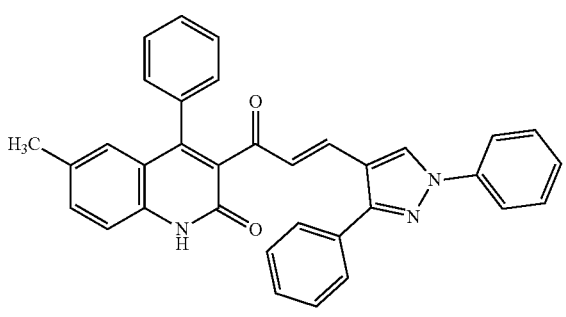 [SMILES: Cc1ccc2[nH]c(=O)c(C(=O)/C=C/c3cn(-c4ccccc4)nc3-c3ccccc3)c(-c3ccccc3)c2c1] | 2-3 |
| 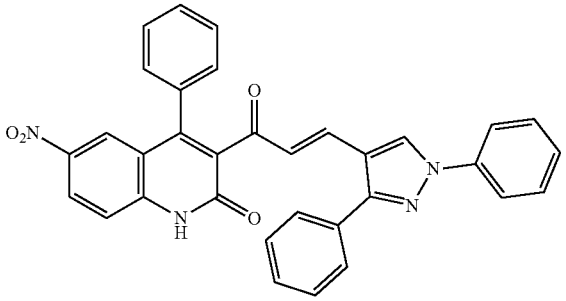 [SMILES: O=C(/C=C/c1cn(-c2ccccc2)nc1-c1ccccc1)c1c(-c2ccccc2)c2cc([N+](=O)[O-])ccc2[nH]c1=O] | 2-4 |
| 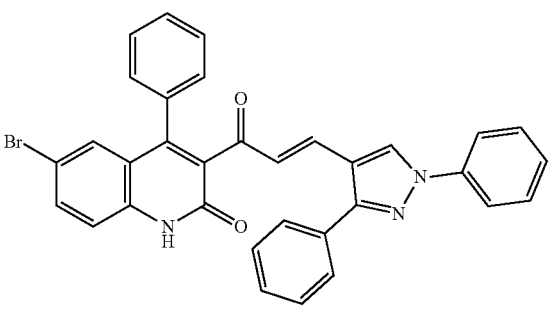 [SMILES: O=C(/C=C/c1cn(-c2ccccc2)nc1-c1ccccc1)c1c(-c2ccccc2)c2cc(Br)ccc2[nH]c1=O] | 2-5 |

TABLE 2-continued
| Compounds | |
|---|---|
| 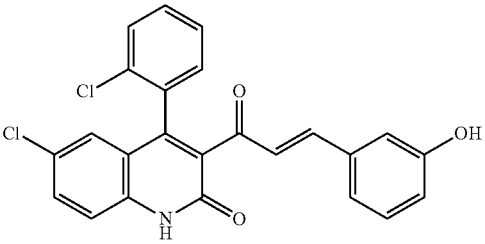 [SMILES: O=C(/C=C/c1cccc(O)c1)c1c(-c2ccccc2Cl)c2cc(Cl)ccc2[nH]c1=O] | 2-6 |
| 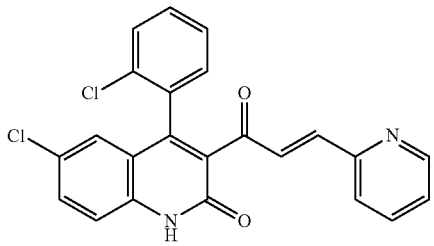 [SMILES: O=C(/C=C/c1ccccn1)c1c(-c2ccccc2Cl)c2cc(Cl)ccc2[nH]c1=O] | 2-7 |
| 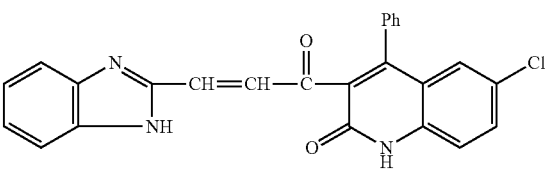 [SMILES: O=C(C=Cc1nc2ccccc2[nH]1)c1c(-c2ccccc2)c2cc(Cl)ccc2[nH]c1=O] | 2-8 |
| 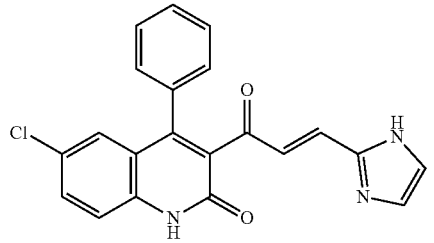 [SMILES: O=C(/C=C/c1ncc[nH]1)c1c(-c2ccccc2)c2cc(Cl)ccc2[nH]c1=O] | 2-9 |
| 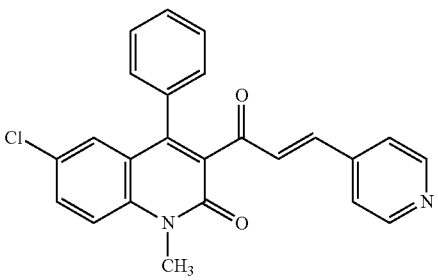 [SMILES: Cn1c(=O)c(C(=O)/C=C/c2ccncc2)c(-c2ccccc2)c2cc(Cl)ccc21] | 2-10 |
| 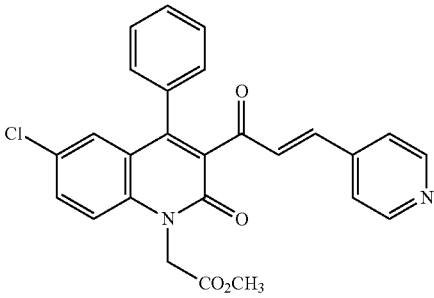 [SMILES: COC(=O)Cn1c(=O)c(C(=O)/C=C/c2ccncc2)c(-c2ccccc2)c2cc(Cl)ccc21] | 2-11 |

TABLE 2-continued
Compounds
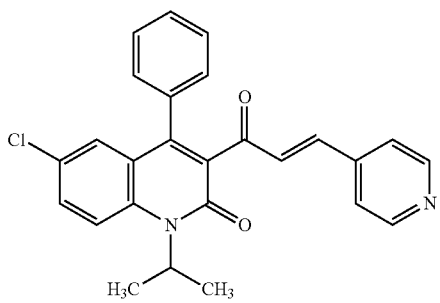
2-12
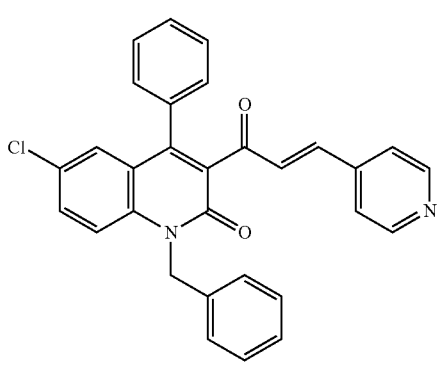 [SMILES: O=C(/C=C/c1ccncc1)c1c(-c2ccccc2)c2cc(Cl)ccc2n(Cc2ccccc2)c1=O]
2-13
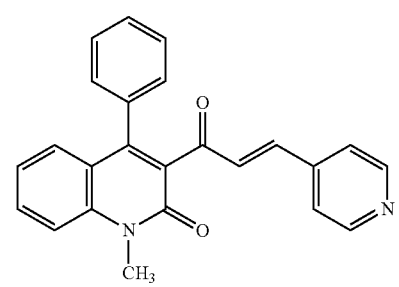 [SMILES: Cn1c(=O)c(C(=O)/C=C/c2ccncc2)c(-c2ccccc2)c2ccccc21]
2-14
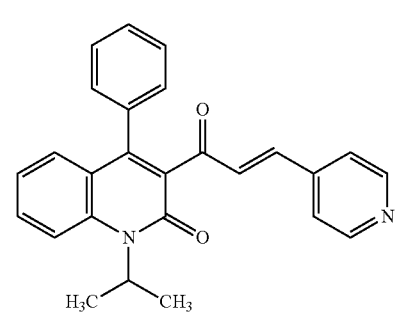 [SMILES: CC(C)n1c(=O)c(C(=O)/C=C/c2ccncc2)c(-c2ccccc2)c2ccccc21]
2-15
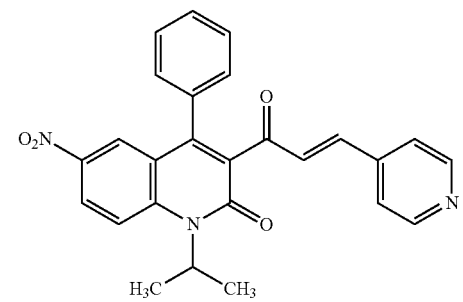 [SMILES: CC(C)n1c(=O)c(C(=O)/C=C/c2ccncc2)c(-c2ccccc2)c2cc([N+](=O)[O-])ccc21]
2-16

TABLE 2-continued

Compounds 2-17

2-18

2-19

2-20

2-21

2-22

2-23

TABLE 2-continued
| Compounds | |
|---|---|
| 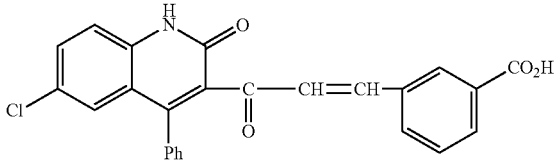 [SMILES: O=C(O)c1cccc(C=CC(=O)c2c(-c3ccccc3)c3cc(Cl)ccc3[nH]c2=O)c1] | 2-24 |
| 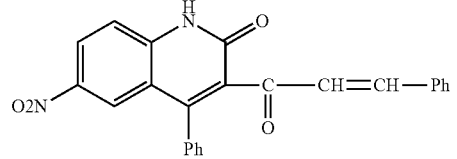 [SMILES: O=C(C=Cc1ccccc1)c1c(-c2ccccc2)c2cc([N+](=O)[O-])ccc2[nH]c1=O] | 2-25 |
| 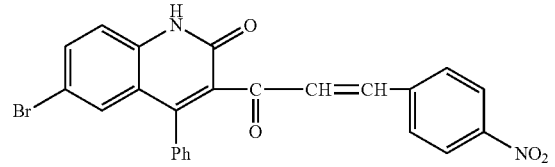 [SMILES: O=C(C=Cc1ccc([N+](=O)[O-])cc1)c1c(-c2ccccc2)c2cc(Br)ccc2[nH]c1=O] | 2-26 |
| 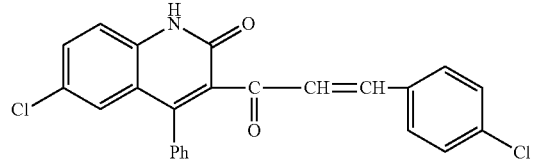 [SMILES: O=C(C=Cc1ccc(Cl)cc1)c1c(-c2ccccc2)c2cc(Cl)ccc2[nH]c1=O] | 2-27 |
| 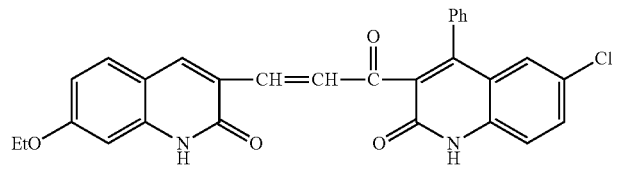 [SMILES: CCOc1ccc2cc(C=CC(=O)c3c(-c4ccccc4)c4cc(Cl)ccc4[nH]c3=O)c(=O)[nH]c2c1] | 2-28 |
| 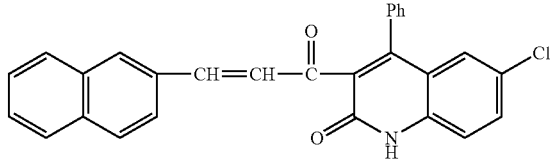 [SMILES: O=C(C=Cc1ccc2ccccc2c1)c1c(-c2ccccc2)c2cc(Cl)ccc2[nH]c1=O] | 2-29 |
| 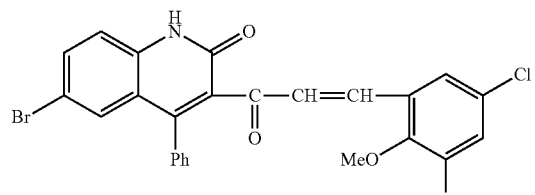 | 2-30 |
| 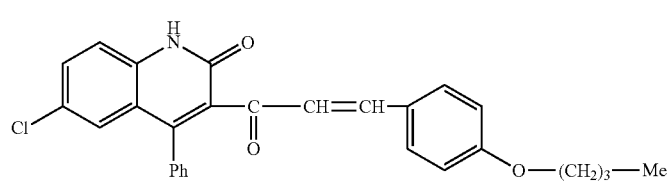 | 2-31 |

TABLE 2-continued

| Compounds | |
|---|---|
| [6-chloro-4-phenyl-quinolin-2(1H)-one-3-yl with CO-CH=CH-(3-nitrophenyl)] | 2-32 |
| [6-bromo-4-(2-fluorophenyl)-quinolin-2(1H)-one-3-yl with CO-CH=CH-(3-nitrophenyl)] | 2-33 |
| [6-bromo-4-phenyl-quinolin-2(1H)-one-3-yl with CO-CH=CH-(4-bromophenyl)] | 2-34 |
| [6-chloro-4-phenyl-quinolin-2(1H)-one-3-yl with CO-CH=CH-(4-NMe₂-phenyl)] | 2-35 |
| [6-chloro-4-phenyl-quinolin-2(1H)-one-3-yl with CO-CH=CH-(2-HO₂C-phenyl)] | 2-36 |
| [6-nitro-4-phenyl-quinolin-2(1H)-one-3-yl with CO-CH=CH-(2-methoxyphenyl)] | 2-37 |
| [6-bromo-4-phenyl-quinolin-2(1H)-one-3-yl with CO-CH=CH-(2,4-dimethoxyphenyl)] | 2-38 |
| [6-chloro-4-phenyl-quinolin-2(1H)-one-3-yl with CO-CH=CH-(3,5-dichlorophenyl)] | 2-39 |

TABLE 2-continued
Compounds
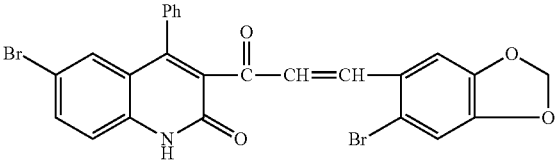 [SMILES: O=C(C=Cc1cc2c(cc1Br)OCO2)c1c(-c2ccccc2)c2cc(Br)ccc2[nH]c1=O]
2-40
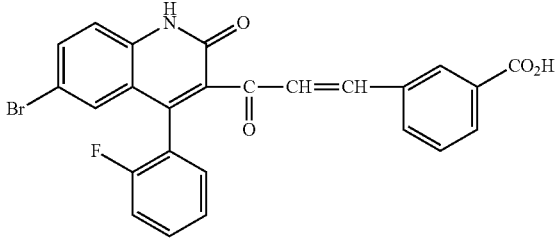 [SMILES: O=C(O)c1cccc(C=CC(=O)c2c(-c3ccccc3F)c3cc(Br)ccc3[nH]c2=O)c1]
2-41
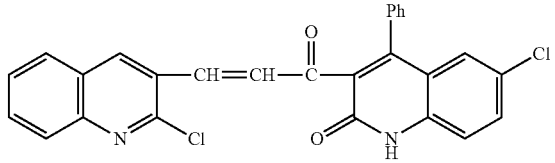 [SMILES: O=C(C=Cc1cc2ccccc2nc1Cl)c1c(-c2ccccc2)c2cc(Cl)ccc2[nH]c1=O]
2-42
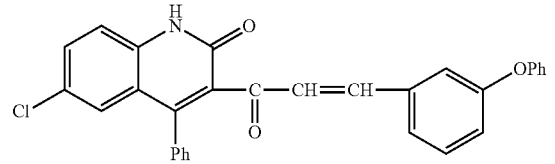 [SMILES: O=C(C=Cc1cccc(Oc2ccccc2)c1)c1c(-c2ccccc2)c2cc(Cl)ccc2[nH]c1=O]
2-43
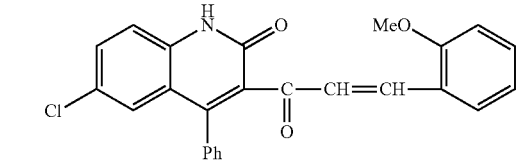 [SMILES: COc1ccccc1C=CC(=O)c1c(-c2ccccc2)c2cc(Cl)ccc2[nH]c1=O]
2-44
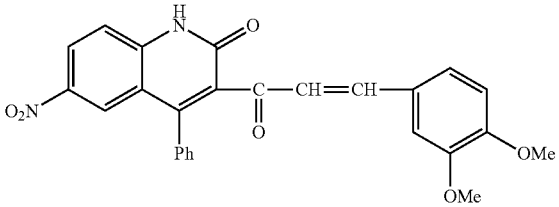 [SMILES: COc1ccc(C=CC(=O)c2c(-c3ccccc3)c3cc([N+](=O)[O-])ccc3[nH]c2=O)cc1OC]
2-45
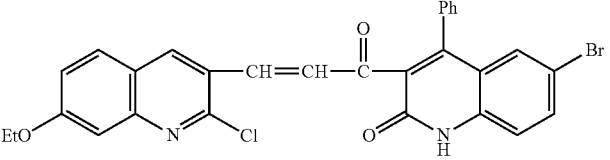 [SMILES: CCOc1ccc2cc(C=CC(=O)c3c(-c4ccccc4)c4cc(Br)ccc4[nH]c3=O)c(Cl)nc2c1]
2-46
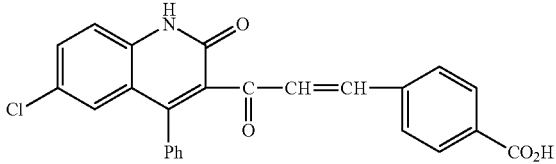 [SMILES: O=C(O)c1ccc(C=CC(=O)c2c(-c3ccccc3)c3cc(Cl)ccc3[nH]c2=O)cc1]
2-47

TABLE 2-continued

| Compounds | |
|---|---|
| (structure) | 2-48 |
| (structure) | 2-49 |
| (structure) | 2-50 |
| (structure) | 2-51 |
| (structure) | 2-52 |
| (structure) | 2-53 |
| (structure) | 2-54 |
| (structure) | 2-55 |

TABLE 2-continued

Compounds

| | |
|---|---|
| [chemical structure] | 2-56 |
| [chemical structure] | 2-57 |
| [chemical structure] | 2-58 |
| [chemical structure] | 2-59 |
| [chemical structure] | 2-60 |
| [chemical structure] | 2-61 |
| [chemical structure] | 2-62 |
| [chemical structure] | 2-63 |

In certain embodiments, the present invention provides any compound described above and herein, or a pharmaceutically acceptable salt thereof. In some embodiments, the present invention provides a compound as depicted in Table 1, above, or a pharmaceutically acceptable salt thereof.

In some embodiments, the present invention provides any compound described above and herein in isolated form.

In certain embodiments, the present invention provides a conjugate comprising PAD4 having a cysteine residue, Cys317, wherein the Cys317 is covalently, and irreversibly, bonded to an inhibitor, such that inhibition of the PAD4 is maintained.

In certain embodiments, the present invention provides a conjugate of formula X:

Cys317-Modifier-Inhibitor Moiety    X wherein:
Cys317 is cysteine 317 of PAD4;
Modifier is a bivalent group resulting from covalent bonding of a Warhead Group with the Cys317 of the PAD4;
Warhead Group is a functional group capable of covalently binding to the Cys317 of the PAD4; and
Inhibitor Moiety is a moiety that binds in the active site of the PAD4.

In certain embodiments, the Inhibitor Moiety of a conjugate of formula X is of formula Y-a or Y-b:

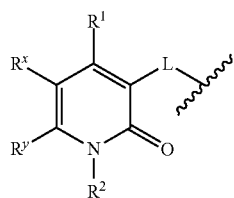

Y-a

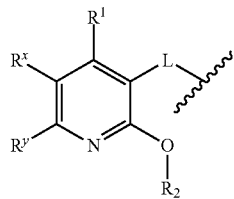

Y-b wherein the wavy bond indicates the point of attachment to the Cys317 of the conjugate of formula X, via the Modifier, and wherein each of L, $R^1$, $R^2$, $R^x$, and $R^y$ is as defined above and described herein.

In some embodiments, the present invention provides a conjugate of formula X-a:

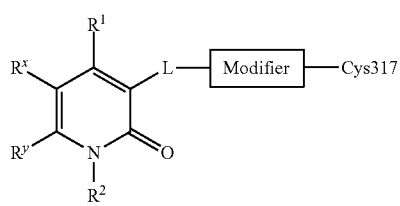

X-a wherein each of the Modifier, Cys317, L, $R^1$, $R^2$, $R^x$, and $R^y$ is as defined above and described herein.

In some embodiments, the present invention provides a conjugate of formula X-b:

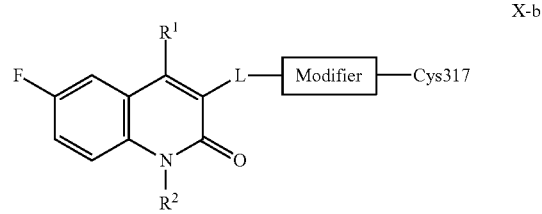

X-b wherein each of the Modifier, Cys317, L, $R^1$, and $R^2$ is as defined above and described herein.

In some embodiments, the present invention provides a conjugate of formula X-c:

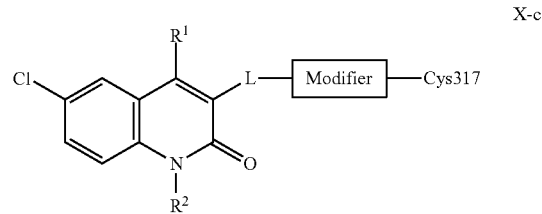

X-c wherein each of the Modifier, Cys317, L, $R^1$, $R^2$, is as defined above and described herein.

In some embodiments, the present invention provides a conjugate of formula X-d:

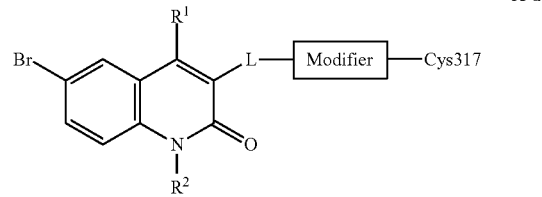

X-d wherein each of the Modifier, Cys317, L, $R^1$, $R^2$, is as defined above and described herein.

In some embodiments, the present invention provides a conjugate of formula X-e:

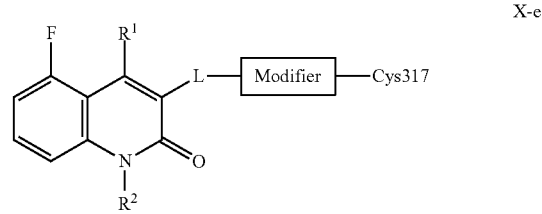

X-e wherein each of the Modifier, Cys317, L, $R^1$, $R^2$, is as defined above and described herein.

In some embodiments, the present invention provides a conjugate of formula X-f:

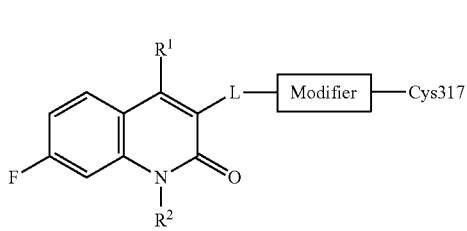

X-f wherein each of the Modifier, Cys317, L, $R^1$, $R^2$, is as defined above and described herein.

In some embodiments, the present invention provides a conjugate of formula X-g:

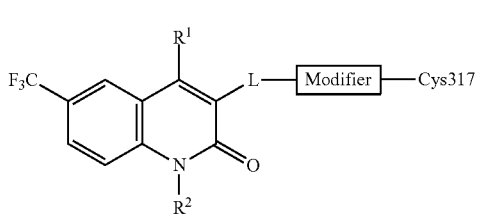

X-g wherein each of the Modifier, Cys317, L, $R^1$, $R^2$, is as defined above and described herein.

In some embodiments, the present invention provides a conjugate of formula XI-a:

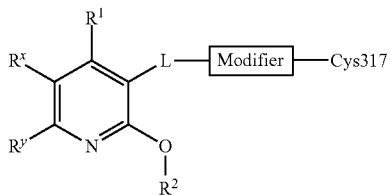

XI-a wherein each of the Modifier, Cys317, L, $R^1$, $R^2$, $R^x$, and $R^y$ is as defined above and described herein.

In some embodiments, the present invention provides a conjugate of formula XI-b:

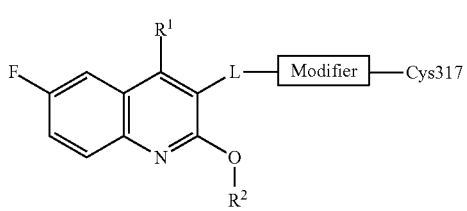

XI-b wherein each of the Modifier, Cys317, L, $R^1$, and $R^2$ is as defined above and described herein.

In some embodiments, the present invention provides a conjugate of formula XI-c:

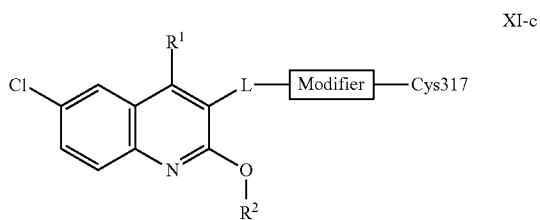

XI-c wherein each of the Modifier, Cys317, L, $R^1$, $R^2$, is as defined above and described herein.

In some embodiments, the present invention provides a conjugate of formula XI-d:

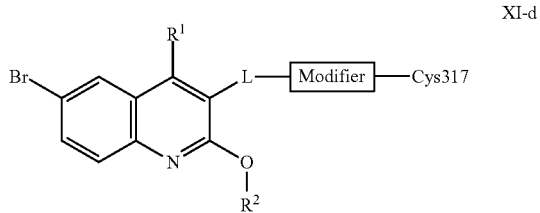

XI-d wherein each of the Modifier, Cys317, L, $R^1$, $R^2$, is as defined above and described herein.

In some embodiments, the present invention provides a conjugate of formula XI-e:

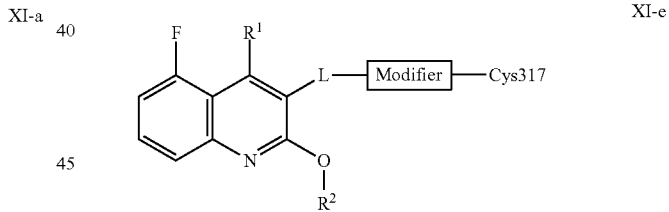

XI-e wherein each of the Modifier, Cys317, L, $R^1$, $R^2$, is as defined above and described herein.

In some embodiments, the present invention provides a conjugate of formula XI-f:

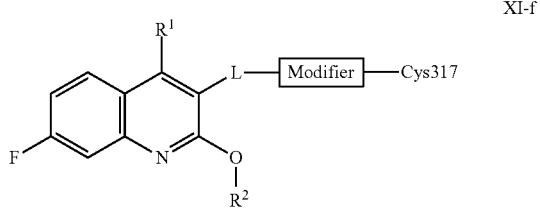

XI-f wherein each of the Modifier, Cys317, L, $R^1$, $R^2$, is as defined above and described herein.

In some embodiments, the present invention provides a conjugate of formula XI-g:

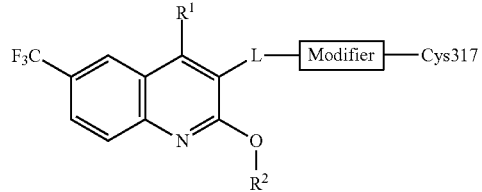

XI-g wherein each of the Modifier, Cys317, L, $R^1$, $R^2$, is as defined above and described herein.

Exemplary modifiers include any bivalent group resulting from covalent bonding of a Warhead Group with the Cys317 of PAD4. It will be understood that the exemplary modifiers below are shown as conjugated to the sulfhydryl of Cys317.

TABLE 3

Exemplary L-Modifiers Conjugated to Cys317 a, b, c

TABLE 3-continued

Exemplary L-Modifiers Conjugated to Cys317 d, e, f, g

TABLE 3-continued
Exemplary L-Modifiers Conjugated to Cys317
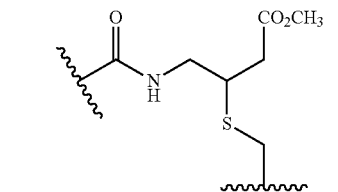 [SMILES: *CSC(CNC(*)=O)CC(=O)OC] h
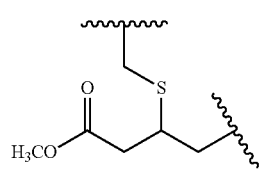 [SMILES: *CSC(C*)CC(=O)OC] i
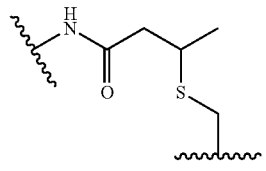 [SMILES: *CSC(C)CC(=O)N*] j
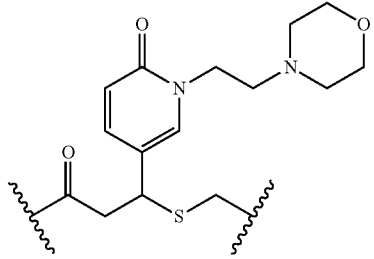 [SMILES: *CSC(CC(*)=O)c1ccc(=O)n(CCN2CCOCC2)c1] k
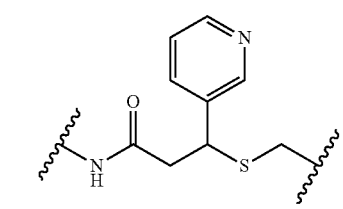 [SMILES: *CSC(CC(=O)N*)c1cccnc1] l
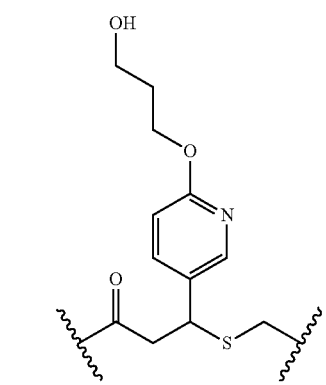 [SMILES: *CSC(CC(*)=O)c1ccc(OCCCO)nc1] m
TABLE 3-continued
Exemplary L-Modifiers Conjugated to Cys317
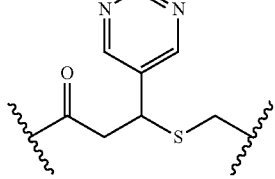 n
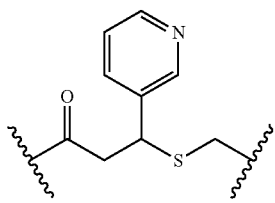 [SMILES: *CSC(CC(*)=O)c1cccnc1] o
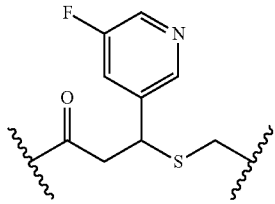 [SMILES: *CSC(CC(*)=O)c1cncc(F)c1] p
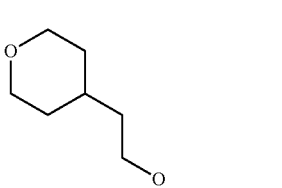 q
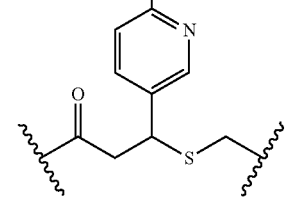 r
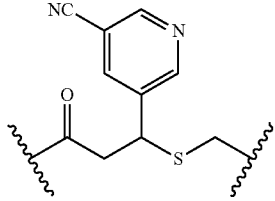 [SMILES: *CSC(CC(*)=O)c1cncc(C#N)c1] s
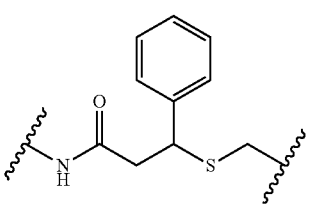 [SMILES: *CSC(CC(=O)N*)c1ccccc1]

TABLE 3-continued
| Exemplary L-Modifiers Conjugated to Cys317 | |
|---|---|
| 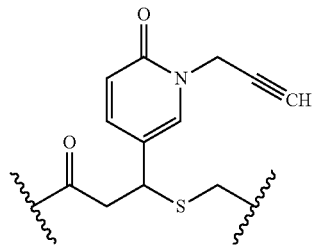 [SMILES: *CSC(CC(*)=O)c1ccc(=O)n(CC#C)c1] | t |
| 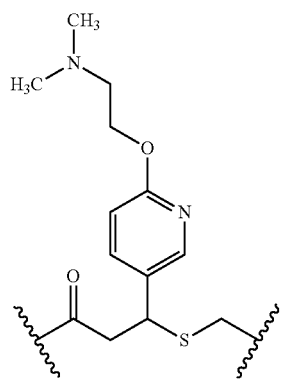 [SMILES: *CSC(CC(*)=O)c1ccc(OCCN(C)C)nc1] | u |
| 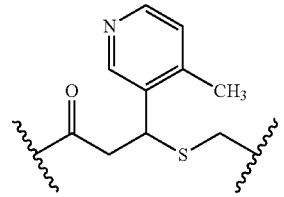 [SMILES: *CSC(CC(*)=O)c1cnccc1C] | v |
| 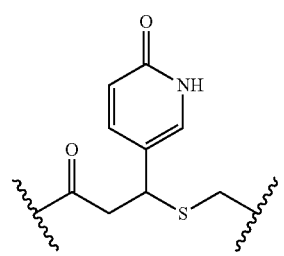 [SMILES: *CSC(CC(*)=O)c1ccc(=O)[nH]c1] | w |
| 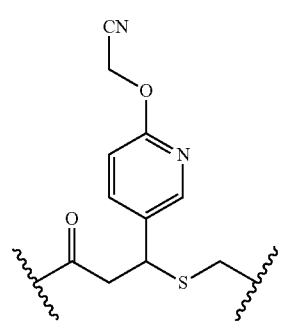 [SMILES: *CSC(CC(*)=O)c1ccc(OCC#N)nc1] | x |
TABLE 3-continued
| Exemplary L-Modifiers Conjugated to Cys317 | |
|---|---|
| 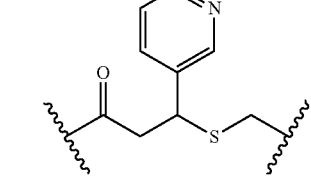 | y |
| 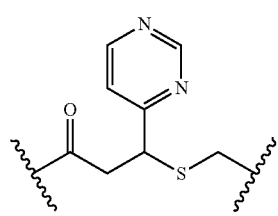 [SMILES: *CSC(CC(*)=O)c1ccncn1] | z |
| 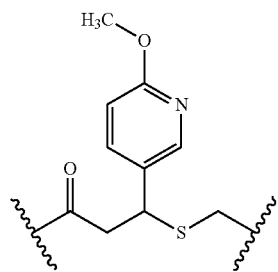 [SMILES: *CSC(CC(*)=O)c1ccc(OC)nc1] | aa |
| 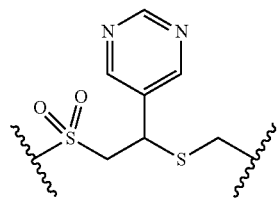 [SMILES: *CSC(CS(*)(=O)=O)c1cncnc1] | bb |
| 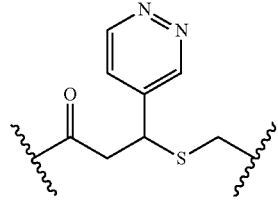 [SMILES: *CSC(CC(*)=O)c1ccnnc1] | cc |
| 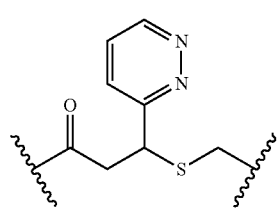 [SMILES: *CSC(CC(*)=O)c1cccnn1] | dd |

TABLE 3-continued
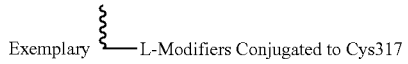
Exemplary L-Modifiers Conjugated to Cys317
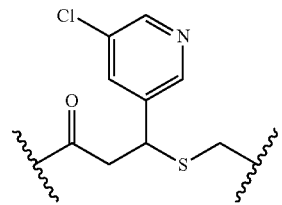
ee
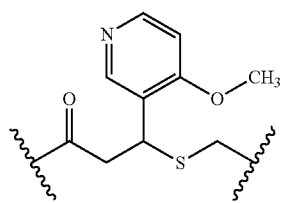 [SMILES: *CSC(CC(*)=O)c1cnccc1OC]
ff
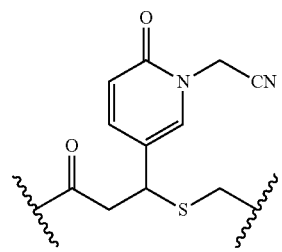 [SMILES: *CSC(CC(*)=O)c1ccc(=O)n(CC#N)c1]
gg
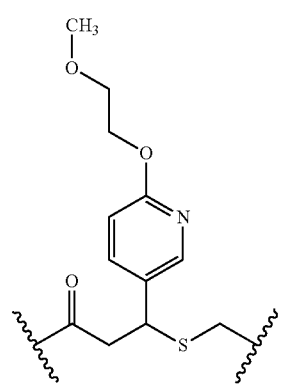 [SMILES: *CSC(CC(*)=O)c1ccc(OCCOC)nc1]
hh
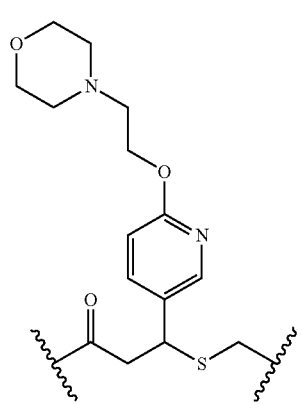 [SMILES: *CSC(CC(*)=O)c1ccc(OCCN2CCOCC2)nc1]
ii
TABLE 3-continued
Exemplary L-Modifiers Conjugated to Cys317
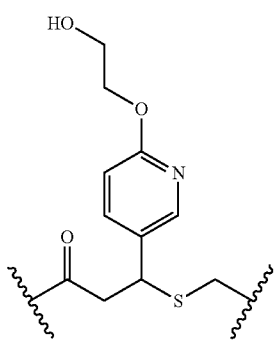 [SMILES: *CSC(CC(*)=O)c1ccc(OCCO)nc1]
jj
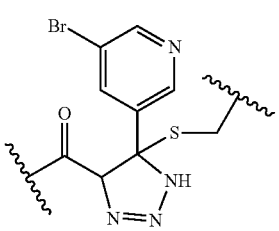 [SMILES: *CSC1(c2cncc(Br)c2)NN=NC1C(*)=O]
kk
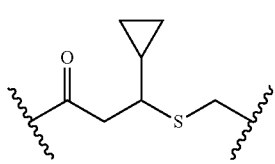 [SMILES: *CSC(CC(*)=O)C1CC1]
ll
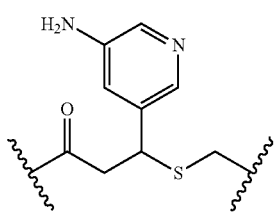 [SMILES: *CSC(CC(*)=O)c1cncc(N)c1]
mm
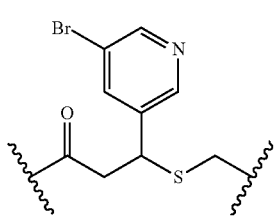 [SMILES: *CSC(CC(*)=O)c1cncc(Br)c1]
nn
oo TABLE 3-continued
Exemplary L-Modifiers Conjugated to Cys317
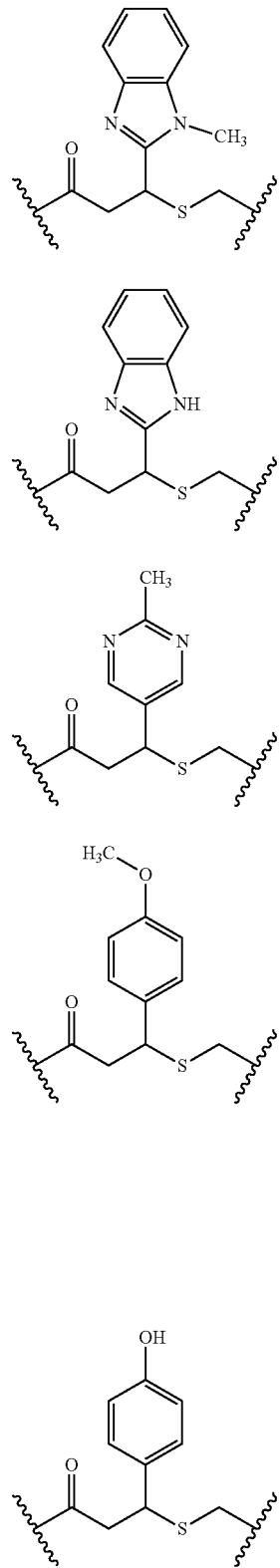
pp
qq
rr
ss
tt
TABLE 3-continued
Exemplary L-Modifiers Conjugated to Cys317
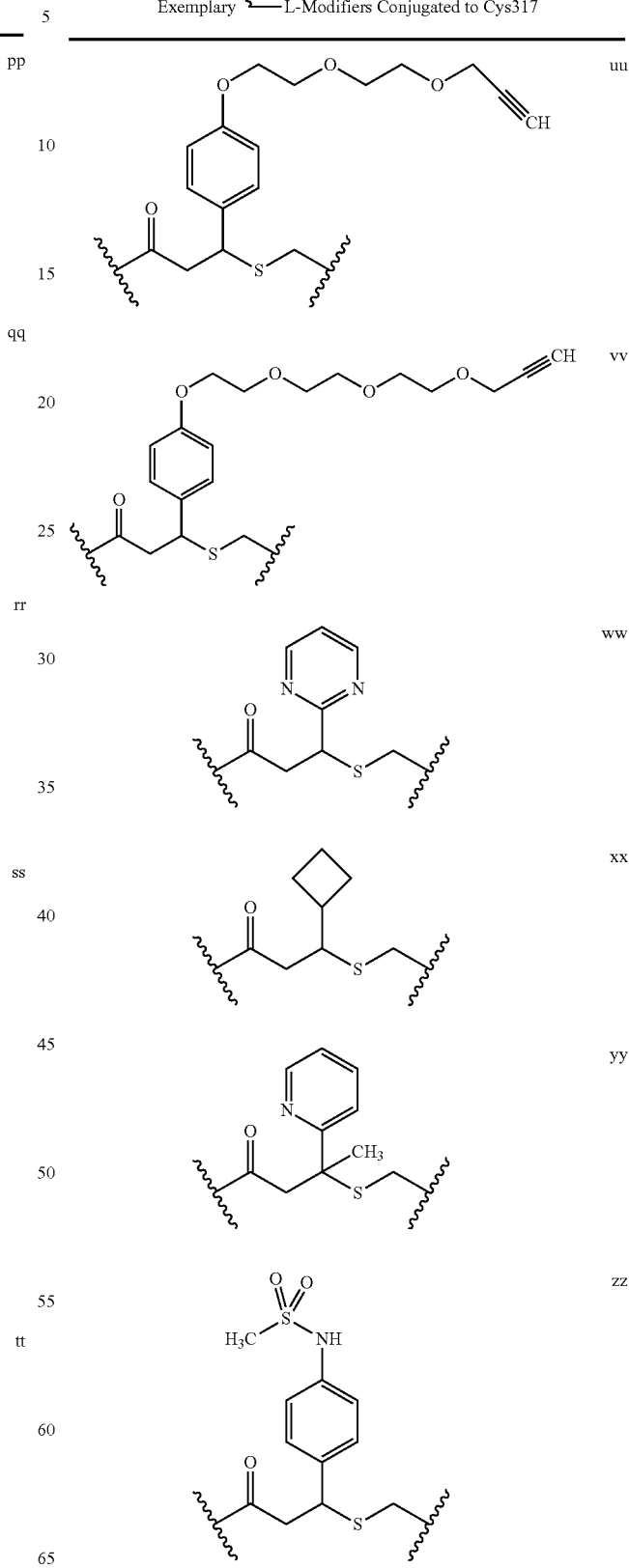
uu
vv
ww
xx
yy
zz TABLE 3-continued Exemplary L-Modifiers Conjugated to Cys317

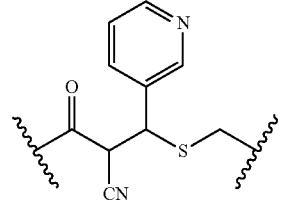 [SMILES: *CSC(c1cccnc1)C(C#N)C(*)=O] aaa

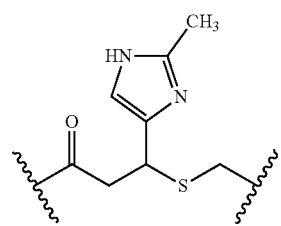 [SMILES: *CSC(CC(*)=O)c1c[nH]c(C)n1] bbb

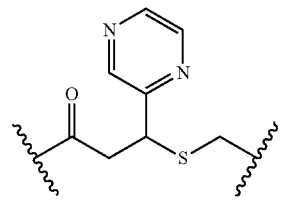 [SMILES: *CSC(CC(*)=O)c1cnccn1] ccc

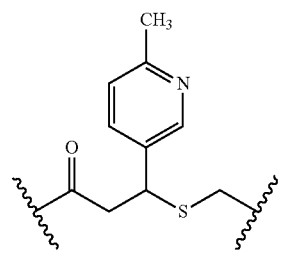 ddd

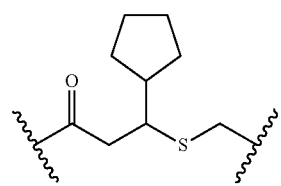 [SMILES: *CSC(CC(*)=O)C1CCCC1] eee

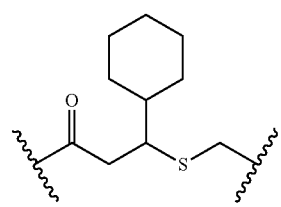 [SMILES: *CSC(CC(*)=O)C1CCCCC1] fff

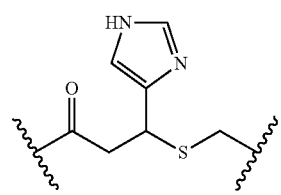 [SMILES: *CSC(CC(*)=O)c1c[nH]cn1] ggg

TABLE 3-continued

Exemplary L-Modifiers Conjugated to Cys317 hhh iii

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit PAD4, in a biological sample or in a patient. In certain embodiments, the amount of compound in compositions of this invention is such that is effective to measurably inhibit PAD4, in a biological sample or in a patient. In certain embodiments, a composition of this invention is formulated for administration to a patient in need of such composition. In some embodiments, a composition of this invention is formulated for oral administration to a patient.

The term "subject," as used herein, is used interchangeably with the term "patient" and means an animal, preferably a mammal. In some embodiments, a subject or patient is a human. In other embodiments, a subject (or patient) is a veterinary subject (or patient). In some embodiments, a veterinary subject (or patient) is a canine, a feline, or an equine subject.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of PAD4.

The activity of a compound utilized in this invention as an inhibitor of PAD4, may be assayed in vitro, in vivo or in a cell line. In vitro assays include assays that determine the inhibition of PAD4. Detailed conditions for assaying a compound utilized in this invention as an inhibitor of PAD4 are set forth in the Examples below. In some embodiments, a provided compound inhibits PAD4 selectively as compared to PAD2.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of PAD4 and are therefore useful for treating one or more disorders associated with activity of PAD4. Thus, in certain embodiments, the present invention provides a method for treating a PAD4-mediated disorder comprising the step of administering to a patient in need thereof a compound of the present invention, or pharmaceutically acceptable composition thereof.

In one embodiment, a PAD4-mediated disorder is a disease, condition, or disorder mediated by inappropriate PAD4 activity. In some embodiments, a PAD4-mediated disorder is selected from the group consisting of rheumatoid arthritis, vasculitis, systemic lupus erythematosus, ulcerative colitis, cancer, cystic fibrosis, asthma, cutaneous lupus erythematosis, and psoriasis. In a further embodiment, the disorder mediated by inappropriate PAD4 activity is rheumatoid arthritis. In a further embodiment, the disorder mediated by inappropriate PAD4 activity is systemic lupus. In a further embodiment, the disorder mediated by inappropriate PAD4 activity is vasculitis. In a further embodiment, the disorder mediated by inappropriate PAD4 activity is cutaneous lupus erythematosis. In a further embodiment, the disorder mediated by inappropriate PAD4 activity is psoriasis.

In one embodiment there is provided a method of treatment of rheumatoid arthritis, vasculitis, systemic lupus erythematosus, ulcerative colitis, cancer, cystic fibrosis, asthma, cutaneous lupus erythematosis, or psoriasis, which method comprises administering to a human subject in need thereof, a therapeutically effective amount of a provided compound or a pharmaceutically acceptable salt thereof.

In one embodiment there is provided a method of treatment of rheumatoid arthritis, which method comprises administering to a human subject in need thereof, a therapeutically effective amount of a provided compound, or a pharmaceutically acceptable salt thereof. In one embodiment there is provided a method of treatment of systemic lupus, which method comprises administering to a human subject in need thereof, a therapeutically effective amount of a provided compound, or a pharmaceutically acceptable salt thereof. In one embodiment there is provided a method of treatment of vasculitis, which method comprises administering to a human subject in need thereof, a therapeutically effective amount of a provided compound, or a pharmaceutically acceptable salt thereof. In one embodiment there is provided a method of treatment of cutaneous lupus erythematosis, which method comprises administering to a human subject in need thereof, a therapeutically effective amount of a provided compound, or a pharmaceutically acceptable salt thereof. In one embodiment there is provided a method of treatment of psoriasis, which method comprises administering to a human subject in need thereof, a therapeutically effective amount of a provided compound, or a pharmaceutically acceptable salt thereof.

In some embodiments, a PAD4-mediated disorder is selected from the group consisting of acid-induced lung injury, acne (PAPA), acute lymphocytic leukemia, acute respiratory distress syndrome, Addison's disease, adrenal hyperplasia, adrenocortical insufficiency, ageing, AIDS, alcoholic hepatitis, alcoholic hepatitis, alcoholic liver disease, allergen induced asthma, allergic bronchopulmonary, aspergillosis, allergic conjunctivitis, alopecia, Alzheimer's disease, amyloidosis, amyotropic lateral sclerosis, and weight loss, angina pectoris, angioedema, anhidrotic ecodermal dysplasia-ID, ankylosing spondylitis, anterior segment, inflammation, antiphospholipid syndrome, aphthous stomatitis, appendicitis, arthritis, asthma, atherosclerosis, atopic dermatitis, autoimmune diseases, autoimmune hepatitis, bee sting-induced inflammation, behcet's disease, Behcet's syndrome, Bell's Palsey, berylliosis, Blau syndrome, bone pain, bronchiolitis, burns, bursitis, cancer, cardiac hypertrophy, carpal tunnel syndrome, catabolic disorders, cataracts, cerebral aneurysm, chemical irritant-induced inflammation, chorioretinitis, chronic heart failure, chronic lung disease of prematurity, chronic lymphocytic leukemia, chronic obstructive pulmonary disease, colitis, complex regional pain syndrome, connective tissue disease, corneal ulcer, crohn's disease, cryopyrin-associated periodic syndromes, cryptococcosis, cystic fibrosis, deficiency of the interleukin-1-receptor antagonist (DIRA), dermatitis, dermatitis endotoxemia, dermatomyositis, diffuse intrinsic pontine glioma, endometriosis, endotoxemia, epicondylitis, erythroblastopenia, familial amyloidotic polyneuropathy, familial cold urticarial, familial mediterranean fever, fetal growth retardation, glaucoma, glomerular disease, glomerular nephritis, gout, gouty arthritis, graft-versus-host disease, gut diseases, head injury, headache, hearing loss, heart disease, hemolytic anemia, Henoch-Scholein purpura, hepatitis, hereditary periodic fever syndrome, herpes zoster and simplex, HIV-1, Hodgkin's disease, Huntington's disease, hyaline membrane disease, hyperammonemia, hypercalcemia, hypercholesterolemia, hyperimmunoglobulinemia D with recurrent fever (HIDS), hypoplastic and other anemias, hypoplastic anemia, idiopathic thrombocytopenic purpura, incontinentia pigmenti, infectious mononucleosis, inflammatory bowel disease, inflammatory lung disease, inflammatory neuropathy, inflammatory pain, insect bite-induced inflammation, iritis, irritant-induced inflammation, ischemia/reperfusion, juvenile rheumatoid arthritis, keratitis, kidney disease, kidney injury caused by parasitic infections, kidney injury caused by parasitic infections, kidney transplant rejection prophylaxis, leptospiriosis, leukemia, Loeffler's syndrome, lung injury, lung injury, lupus, lupus, lupus nephritis, lymphoma, meningitis, mesothelioma, mixed connective tissue disease, Muckle-Wells syndrome (urticaria deafness amyloidosis), multiple sclerosis, muscle wasting, muscular dystrophy, myasthenia gravis, myocarditis, mycosis fungiodes, mycosis fungoides, myelodysplastic syndrome, myositis, nasal sinusitis, necrotizing enterocolitis, neonatal onset multisystem inflammatory disease (NOMID), nephrotic syndrome, neuritis, neuropathological diseases, non-allergen induced asthma, obesity, ocular allergy, optic neuritis, organ transplant, osterarthritis, otitis media, paget's disease, pain, pancreatitis, Parkinson's disease, pemphigus, pericarditis, periodic fever, periodontitis, peritoneal endometriosis, pertussis, pharyngitis and adenitis (PFAPA syndrome), plant irritant-induced inflammation, pneumonia, pneumonitis, pneumosysts infection, poison ivy/urushiol oil-induced inflammation, polyarteritis *nodosa*, polychondritis, polycystic kidney disease, polymyositis, psoriasis, psoriasis, psoriasis, psoriasis, psychosocial stress diseases, pulmonary disease, pulmonary hypertension, pulmonayr fibrosis, pyoderma gangrenosum, pyogenic sterile arthritis, renal disease, retinal disease, rheumatic carditis, rheumatic disease, rheumatoid arthritis, sarcoidosis, seborrhea, sepsis, severe pain, sickle cell, sickle cell anemia, silica-induced disease, Sjogren's syndrome, skin diseases, sleep apnea, solid tumors, spinal cord injury, Stevens-Johnson syndrome, stroke, subarachnoid hemorrhage, sunburn, temporal arteritis, tenosynovitis, thrombocytopenia, thyroiditis, tissue transplant, TNF receptor associated periodic syndrome (TRAPS), toxoplasmosis, transplant, traumatic brain injury, tuberculosis, type 1 diabetes, type 2 diabetes, ulcerative colitis, urticarial, uveitis, and Wegener's granulomatosis.

In one embodiment, the invention provides a provided compound, or a pharmaceutically acceptable salt thereof, for use in therapy. In another embodiment, the invention provides a provided compound, or a pharmaceutically acceptable salt thereof, for use in the treatment of a disorder mediated by inappropriate PAD4 activity. In another embodiment, the invention provides a provided compound, or a pharmaceutically acceptable salt thereof, for use in the treatment of rheumatoid arthritis, vasculitis, systemic lupus erythematosus, ulcerative colitis, cancer, cystic fibrosis, asthma, cutaneous lupus erythematosis, or psoriasis. In another embodiment, the invention provides a provided compound, or a pharmaceutically acceptable salt thereof, for use in the treatment of rheumatoid arthritis. In another embodiment, the invention provides a provided compound, or a pharmaceutically acceptable salt thereof, for use in the treatment of systemic lupus. In another embodiment, the invention provides a provided compound, or a pharmaceutically acceptable salt thereof, for use in the treatment of vasculitis. In another embodiment, the invention provides a provided compound, or a pharmaceutically acceptable salt thereof, for use in the treatment of cutaneous lupus erythematosis. In another embodiment, the invention provides a provided compound, or a pharmaceutically acceptable salt thereof, for use in the treatment of psoriasis. In another embodiment, the invention provides the use of a provided compound, or a pharmaceutically acceptable salt thereof, in the manufacture of a medicament for use in the treatment of a disorder mediated by inappropriate PAD4 activity. In another embodiment, the invention provides the use of a provided compound, or a pharmaceutically acceptable salt thereof, in the manufacture of a medicament for use in the treatment of rheumatoid arthritis, vasculitis, systemic lupus erythematosus, ulcerative colitis, cancer, cystic fibrosis, asthma, cutaneous lupus erythematosis, or psoriasis. In another embodiment, the invention provides the use of a provided compound, or a pharmaceutically acceptable salt thereof, in the manufacture of a medicament for use in the treatment of rheumatoid arthritis. In another embodiment, the invention provides the use of a provided compound, or a pharmaceutically acceptable salt thereof, in the manufacture of a medicament for use in the treatment of systemic lupus. In another embodiment, the invention provides the use of a provided compound, or a pharmaceutically acceptable salt thereof, in the manufacture of a medicament for use in the treatment of vasculitis. In another embodiment, the invention provides the use of a provided compound, or a pharmaceutically acceptable salt thereof, in the manufacture of a medicament for use in the treatment of cutaneous lupus erythematosis. In another embodiment, the invention provides the use of a provided compound, or a pharmaceutically acceptable salt thereof, in the manufacture of a medicament for use in the treatment of psoriasis. In a further embodiment, the invention provides a pharmaceutical composition for the treatment or prophylaxis of a disorder mediated by inappropriate PAD4 activity comprising a provided compound, or a pharmaceutically acceptable salt thereof. In a further embodiment, the invention provides a pharmaceutical composition for the treatment or prophylaxis of rheumatoid arthritis, vasculitis, systemic lupus erythematosus, ulcerative colitis, cancer, cystic fibrosis, asthma, cutaneous lupus erythematosis, or psoriasis, comprising a provided compound, or a pharmaceutically acceptable salt thereof. In a further embodiment, the invention provides a pharmaceutical composition for the treatment or prophylaxis of rheumatoid arthritis comprising a provided compound, or a pharmaceutically acceptable salt thereof. In a further embodiment, the invention provides a pharmaceutical composition for the treatment or prophylaxis of systemic lupus comprising a provided compound, or a pharmaceutically acceptable salt thereof. In a further embodiment, the invention provides a pharmaceutical composition for the treatment or prophylaxis of vasculitis comprising a provided compound, or a pharmaceutically acceptable salt thereof. In a further embodiment, the invention provides a pharmaceutical composition for the treatment or prophylaxis of cutaneous lupus erythematosis comprising a provided compound, or a pharmaceutically acceptable salt thereof. In a further embodiment, the invention provides a pharmaceutical composition for the treatment or prophylaxis of psoriasis comprising a provided compound, or a pharmaceutically acceptable salt thereof All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Preparative HPLC Methods
Basic HPLC Preparative Method A
Column: XBridge™ Prep. C18 10 um OBDTM, 30×100 mm
Mobile Phase: 5-95% Acetonitrile (0.2% ammonium hydroxide) in Water (0.2% ammonium hydroxide) over 14 min
Flow Rate: 40 ml/min
UV Detection: 215 and 254 nm
Basic HPLC Preparative Method B
Instrument: Shimadzu LC-20AP
Column: Phenomenex Gemini C18 250×50 mm×10 µm
Mobile Phase: 1-46% Acetonitrile in Water (0.05% ammonium hydroxide) over 28 min
Flow Rate: 120 ml/min
UV Detection: 220 and 254 nm
Acidic HPLC Preparative Method
Column: Sunfire™ Prep. C18 10 um OBDTM, 30×100 mm
Mobile Phase: 5-95% Acetonitrile (0.1% formic acid) in Water (0.1% formic acid) over 14 min
Flow Rate: 40 ml/min
UV Detection: 215 and 254 nm
Analytical LCMS Methods:
Method A
MET/u-HPLC (low pH MSQ1 7 min method)
Column: Phenomenex Kinetex-XB C18, 2.1 mm×100 mm, 1.7 µm
Flow rate: 0.6 ml/min
Mobile Phase: A, Formic acid (aqueous) 0.1% and B, Formic acid (MeCN) 0.1%
Injection Vol: 3 µl
Temp.: 40° C.
Detection: 215 nm (nominal)
Gradient Time (min)-% B
0.00-5
5.30-100
5.80-100
5.82-5
Method B
MET/CR/1600 (high pH MS 10 7 min method)
Column: Phenomenex Gemini C18, 2.0 mm×100 mm, 3 µm
Flow rate: 0.5 ml/min
Mobile phase: A, 2 mM ammonium bicarbonate in HPLC grade water pH10
B, HPLC grade MeCN
Injection volume: 3 µl
Temperature: 50° C.
Detection: 215 nm
Gradient time: (min)-% B
0.0-5
5.50-100
5.90-100
5.92-5
9.00-5
Method C
METCR 1416 (low pH Shimadzu 7 min method)
Column: Waters Atlantis dC18, 2.1 mm×100 mm, 3 µm column
Flow rate: 0.6 ml/min
Mobile Phase: A, Formic acid (aqueous) 0.1% and B, Formic acid (acetonitrile) 0.1%
Injection Vol: 3 µl
Temp.: 40° C.
Detection: 215 nm (nominal)
Gradient Time (min)-% B
0.00-5
5.00-100
5.40-100
5.42-5
Method D
METCR 1410 (low pH Shimadzu 2 min method)
Column: Kinetex Core-Shell C18, 2.1 mm×50 mm, 5 m column
Flow rate: 1.2 ml/min
Mobile Phase: A, Formic acid (aqueous) 0.1% and B, Formic acid (acetonitrile) 0.1%
Injection Vol: 3 µl
Temp.: 40° C.
Detection: 215 nm (nominal)
Gradient Time (min)-% B
0.00-5
1.20-100

1.30-100
1.31-5
Method E
MET/u-HPLC (high pH MS 16 7 min method)
Column: Waters UPLC CSH C18, 2.1 mm×100 mm 5 μm column
Flow rate: 0.6 ml/min
Mobile Phase: A, 2 mM Ammonium bicarbonate modified to pH 10 with Ammonium hydroxide (aqueous) and B, acetonitrile
Injection Vol: 3 μl
Temp.: 40° C.
Detection: 215 nm (nominal)
Gradient Time (min)-% B
0.00-5
5.30-100
5.80-100
5.82-5
Method F
MET/CR/0990 (high pH 3 min method)
Column: Phenomenex Gemini C18, 2.0 mm×100 mm, 3 μm
Flow rate: 1 ml/min
Mobile phase: A, 2 mM ammonium bicarbonate in HPLC grade water pH10
B, HPLC grade MeCN
Injection volume: 3 μl
Temperature: 60° C.
Detection: 215 nm
Gradient time: (min)-% B
0.0-1
1.80-100
2.10-100
2.30-1
Method G
WUXIAB01.M
Column: Agilent 5 TC-C18, 2.1*50 mm, 5 μm
Flow rate: 0.8 ml/min
Mobile Phase: A: 0.0375% TFA in water (v/v)
B: 0.01875% TFA in Acetonitrile (v/v)
Temperature: 50° C.
Detection: DAD (220 & 254 nm)
Gradient Time (min)-% B
0.0-10
0.40-10
3.40-100
3.90-100
3.91-10
4.00-10
4.50-10
Method H
0-60AB R 220&254.M
Column: Chromolith@Flash RP-18E 25-2MM
Flow rate: 1.5 ml/min
Mobile Phase: A: 0.0375% TFA in water (v/v)
B: 0.01875% TFA in Acetonitrile (v/v)
Temperature: 50° C.
Detection: DAD 220 & 254 nm)
Gradient Time (min)-% B
0.0-0
0.80-60
1.20-60
1.21-0
1.50-0
Method I
5-95AB R 220&254.M
Column: Chromolith@Flash RP-18E 25-2MM
Flow rate: 1.5 ml/min
Mobile Phase: A: 0.0375% TFA in water (v/v)
B: 0.01875% TFA in Acetonitrile (v/v)
Temperature: 50° C.
Detection: DAD (220 & 254 nm)
Gradient Time (min)-% B
0.01-5
0.80-95
1.2-95
1.21-5
1.5-5

Certain compounds of the present invention were prepared according to Schemes 1 through 24, below.

Example 1. Synthesis of 6-methyl-4-phenyl-3-[(2E)-3-phenylprop-2-enoyl]-1,2-dihydroquinolin-2-one, I-138

6-methyl-4-phenyl-3-[(2E)-3-phenylprop-2-enoyl]-1,2-dihydroquinolin-2-one (I-138) (EOAI3435746) was synthesized according to the procedures described in Scheme 1.

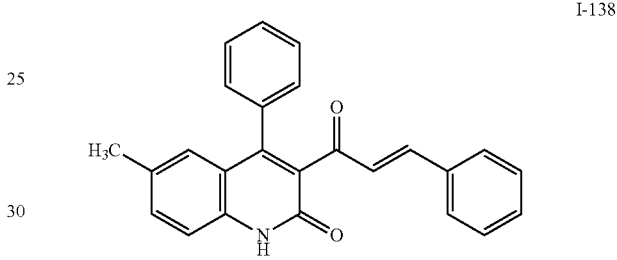

I-138

Scheme 1

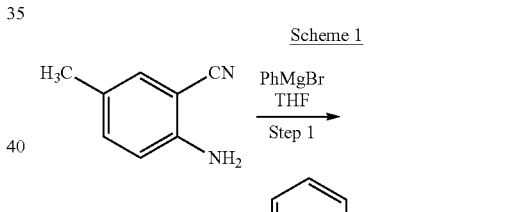

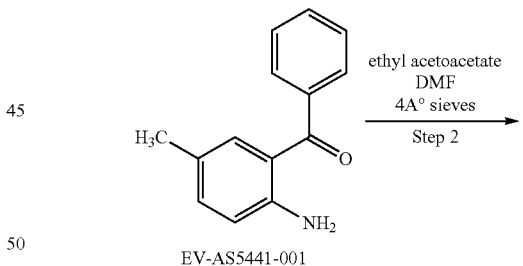

EV-AS5441-001

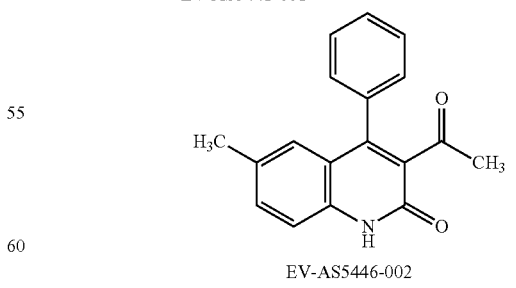

EV-AS5446-002

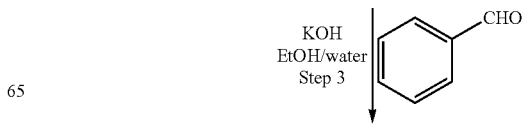

-continued

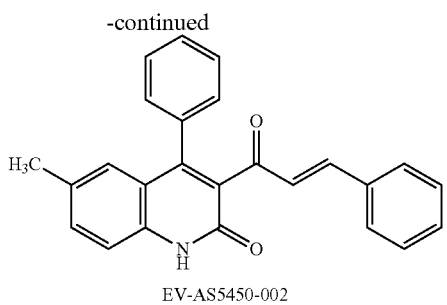

EV-AS5450-002

2-benzoyl-4-methylaniline (EV-AS5441-001)—Step 1

To a solution of Phenylmagnesium bromide (1.6M in CBME, 14.2 ml, 22.7 mmol) at 0° C. was added a solution of 2-amino-5-methylbenzonitrile (1 g, 7.6 mmol) in THF (10 ml) and the solution was allowed to slowly warm to room temperature over 17 h. A further portion of Phenylmagnesium bromide (1.6M in CBME, 7.0 ml, 11.3 mmol) was added and the solution was stirred at room temperature for 17 h. The brown solution was cooled in an ice bath, treated with aq HCl solution (1M, 30 ml) and extracted with ether (2×25 ml). The product was now entirely in the aqueous layer so the organic extracts were discarded. The aqueous extracts were neutralized using saturated $NaHCO_3$ solution and extracted with EtOAc (2×50 ml). The organic extracts were dried over $Na_2SO_4$ and concentrated in vacuo to afford 1.09 g (65%) of 2-benzoyl-4-methylaniline (EV-AS5441-001) as an orange oil. LCMS (method D): retention time 1.19 min, M/z=211.9 (M+1).

3-acetyl-6-methyl-4-phenyl-1,2-dihydroquinolin-2-one (EV-AS5446-002)—Step 2

To a solution of 2-benzoyl-4-methylaniline (EV-AS5441-001, 250 mg, 1.12 mmol) in DMF (2 ml) was added ethyl 3-oxobutanoate (213 µl, 1.69 mmol) and 4A° molecular sieves (60 mg) and the mixture was stirred and heated at 160° C. for 30 min under microwave irradiation. The reaction mixture was concentrated in vacuo to afford a beige powder. Trituration using EtOAc, and washing with $Et_2O$ afforded 311 mg (66%) of 3-acetyl-6-methyl-4-phenyl-1,2-dihydroquinolin-2-one (EV-AS5446-002) as a pale yellow powder. LCMS (method D): retention time 1.10 min, M/z=277.9 (M+1).

6-methyl-4-phenyl-3-[(2E)-3-phenylprop-2-enoyl]-1,2-dihydroquinolin-2-one (I-138) (EV-AS5450-002)—Step 3

To a solution of 3-acetyl-4-phenyl-1,2-dihydroquinolin-2-one (EV-AS5446-002, 43 mg, 0.155 mmol) in EtOH/water (2:1, 3 ml) at 0° C. was added potassium hydroxide (85%, 256 mg, 9.015 mmol) and the solution was stirred for 20 min before benzaldehyde (16 µl, 0.155 mmol) was added and the mixture was stirred and allowed to warm to room temperature over 2 h. The suspension was treated with Acetic acid (0.25 ml) and stirred at RT for 10 min, resulting in the formation of a bright yellow precipitate. The solid was collected by filtration, washed with water, followed by ether, and dried under vacuum to afford 46 mg (74%) of 6-methyl-4-phenyl-3-[(2E)-3-phenylprop-2-enoyl]-1,2-dihydroquinolin-2-one (I-138) (EV-AS5450-002) as a pale yellow powder. LCMS (method A): retention time 3.54 min, M/z=366.1 (M+1).

Special Cases for Scheme 1

Example 2. Synthesis of 6-fluoro-4-phenyl-3-[(2E)-3-(pyridazin-4-yl)prop-2-enoyl]-1,2-dihydroquinolin-2-one, I-13

6-fluoro-4-phenyl-3-[(2E)-3-(pyridazin-4-yl)prop-2-enoyl]-1,2-dihydroquinolin-2-one (I-13) (EOAI3459010) was synthesized according to the procedures described in Scheme 1 using alternative aldol conditions according to Scheme 1.1

Scheme 1.1

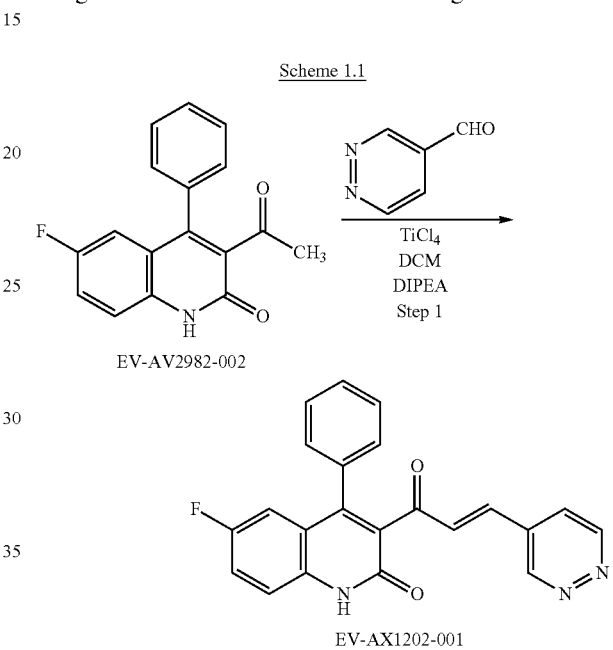

6-fluoro-4-phenyl-3-[(2E)-3-(pyridazin-4-yl)prop-2-enoyl]-1,2-dihydroquinolin-2-one (I-13)

(EV-AX1202-001)—Step 1

To a cold (0° C.) suspension of 3-acetyl-6-fluoro-4-phenyl-1,2-dihydroquinolin-2-one (EV-AV2982-001, 120 mg, 0.43 mmol) in anhydrous DCM (3 ml) was added $TiCl_4$ (1M in DCM, 469.28 µl, 0.47 mmol) dropwise to give a dark brown solution. The mixture was stirred at 0° C. for 20 min. DIPEA (85.46 µl, 0.49 mmol) was then added slowly to the reaction mixture, upon which the mixture fumed and turned deep orange. The mixture was stirred for 10 min at 0° C. before a solution of pyridazine-4-carbaldehyde (55.34 mg, 0.51 mmol) in anhydrous DCM (1 ml) was then added. The mixture was stirred at 0° C. for 30 min and allowed to warm to room temperature overnight. The reaction mixture was diluted with DCM (10 ml) and water (10 ml). The organic layer was collected, dried over $MgSO_4$, filtered and concentrated in vacuo. The residue was then purified by Basic HPLC preparative method A and the relevant fractions were lyophilized to afford 10.3 mg (6.5%) of 6-fluoro-4-phenyl-3-[(2E)-3-(pyridazin-4-yl)prop-2-enoyl]-1,2-dihydroquinolin-2-one (I-13) (EV-AX1202-001) as a yellow powder. LCMS (method A): retention time 2.59 min, M/z=372.1 (M+1).

Example 3. Synthesis of 4-phenyl-3-[(2E)-3-(pyrimidin-5-yl)prop-2-enoyl]-1,2-dihydroquinolin-2-one, I-122

4-phenyl-3-[(2E)-3-(pyrimidin-5-yl)prop-2-enoyl]-1,2-dihydroquinolin-2-one (I-122) (EOAI3447163) was synthesized according to the procedures described in Scheme 1 using alternative aldol conditions according to Scheme 1.2

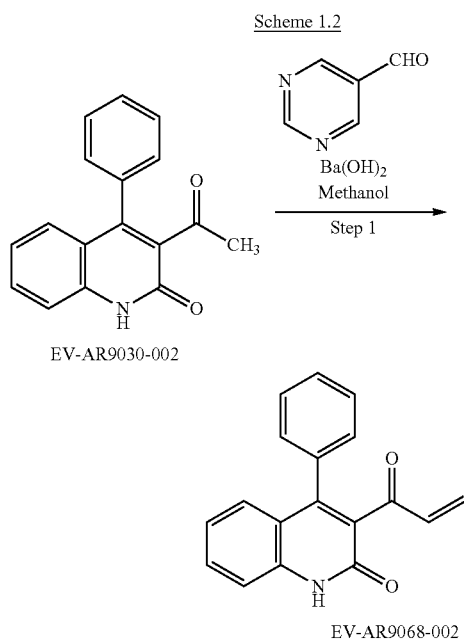

EV-AR9030-002

EV-AR9068-002

4-phenyl-3-[(2E)-3-(pyrimidin-5-yl)prop-2-enoyl]-1,2-dihydroquinolin-2-one (I-122) (EV-AR9068-002)—Step 1

To Ba(OH)$_2$ (95%, 137 mg, 0.76 mmol) was added Water (120 µl) and pyrimidine-5-carbaldehyde (164.23 mg, 1.52 mmol) in Methanol (2 ml). To the resultant mixture was added 3-acetyl-4-phenyl-1,2-dihydroquinolin-2-one (EV-AR9030-002, 200 mg, 0.76 mmol) in Methanol (6 ml) dropwise over 10 min and the reaction was stirred at room temperature for 30 min. The reaction was quenched with Acetic acid (6 ml), diluted with DCM (60 ml) and washed with water (30 ml). The aqueous was extracted with DCM (2×60 ml). The organics were combined, dried over MgSO$_4$ and concentrated in vacuo to afford a yellow oil. The crude material was purified by Basic preparative HPLC method A and the relevant fractions were lyophilized to afford 120 mg (45%) of 4-phenyl-3-[(2E)-3-(pyrimidin-5-yl)prop-2-enoyl]-1,2-dihydroquinolin-2-one (I-122) (EV-AR9068-002) as a yellow powder. LCMS (method A): retention time 3.96 min, M/z=354.2 (M+1).

Example 4. Synthesis of 3-[(2E)-3-cyclohexylprop-2-enoyl]-4-phenyl-1,2-dihydroquinolin-2-one, I-127

3-[(2E)-3-cyclohexylprop-2-enoyl]-4-phenyl-1,2-dihydroquinolin-2-one (I-127) (EOAI3442130) was synthesized according to the procedures described in Scheme 1 using alternative aldol conditions according to Scheme 1.3

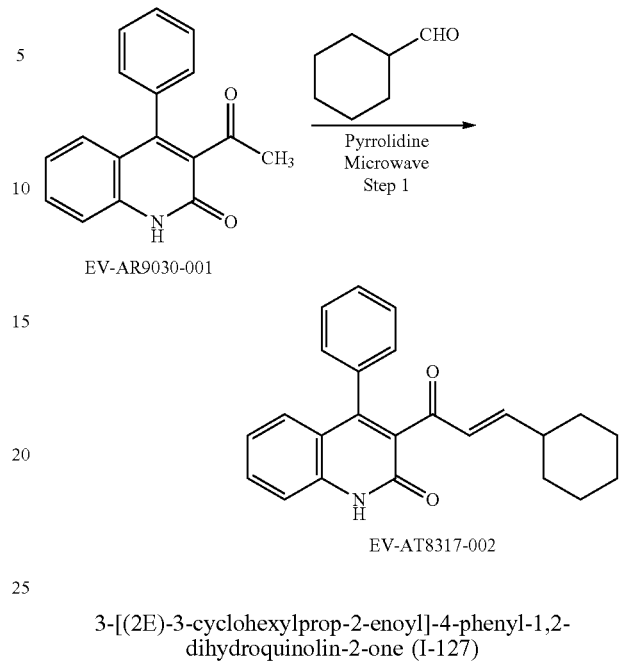

EV-AR9030-001

EV-AT8317-002

3-[(2E)-3-cyclohexylprop-2-enoyl]-4-phenyl-1,2-dihydroquinolin-2-one (I-127)

(EV-AT8317-002)—Step 1

A solution of 3-acetyl-4-phenyl-1,2-dihydroquinolin-2-one (EV-AR9022-001, 100 mg, 0.38 mmol) in cyclohexanecarbaldehyde (2 ml, 16.51 mmol) was treated with pyrrolidine (15.6 l, 0.19 mmol) and the mixture was heated under microwave irradiation at 150° C. for 75 min. More pyrrolidine (15.6 µl, 0.19 mmol) was added and the mixture was heated at 150° C. for 2 h. The brown solution was acidified with Acetic acid, diluted with water and extracted twice with EtOAc. The extracts were washed with water followed by brine, dried over MgSO$_4$ and concentrated in vacuo to afford a mobile brown oil. The material was purified by acidic preparative HPLC and the relevant fractions were lyophilized to afford 3-[(2E)-3-cyclohexylprop-2-enoyl]-4-phenyl-1,2-dihydroquinolin-2-one 42 mg (31%) (I-127) (EV-AT8317-002) as a pinkish powder. LCMS (method A): retention time 3.86 min, M/z=358.2 (M+1)

Example 5. Synthesis of 6-methyl-4-phenyl-3-(prop-2-enoyl)-1,2-dihydroquinolin-2-one, I-133

6-methyl-4-phenyl-3-(prop-2-enoyl)-1,2-dihydroquinolin-2-one (I-133) (EOAI3440735) was synthesized according to the procedures described in Scheme 1 using alternative aldol conditions according to Scheme 1.4

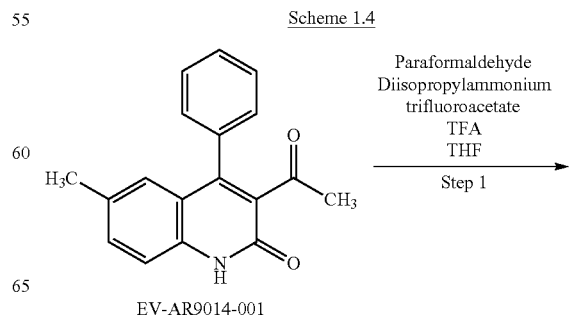

EV-AR9014-001

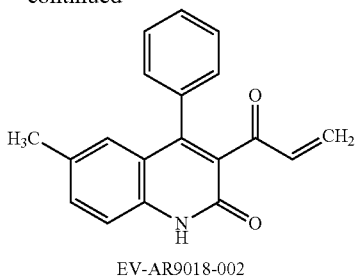

6-methyl-4-phenyl-3-(prop-2-enoyl)-1,2-dihydroquinolin-2-one (EV-AR9018-002)—Step 1

To a solution of 3-acetyl-6-methyl-4-phenyl-1,2-dihydroquinolin-2-one (100 mg, 0.36 mmol) and paraformaldehyde (43.31 mg, 1.44 mmol) in anhydrous THF (4 ml) was added Diisopropylammonium trifluroacetate (77.61 mg, 0.36 mmol) and TFA (2.76 µl, 0.04 mmol). The reaction mixture was sealed and heated at 150° C. for 30 min. The reaction was retreated with 2 equiv. of paraformaldehyde and heated at 150° C. for an additional 30 min. The reaction mixture was concentrated in vacuo and purified by acidic preparative HPLC to afford 6-methyl-4-phenyl-3-(prop-2-enoyl)-1,2-dihydroquinolin-2-one (I-133) (EV-AR9018-002) (22 mg, 20%) as a white powder. LCMS (method A): retention time 2.93 min, M/z=290 (M+1).

Example 6. Synthesis of 3-[(1E)-3-oxo-3-(2-oxo-4-phenyl-1,2-dihydro-1,7-naphthyridin-3-yl)prop-1-en-1-yl]benzonitrile, I-32

3-[(1E)-3-oxo-3-(2-oxo-4-phenyl-1,2-dihydro-1,7-naphthyridin-3-yl)prop-1-en-1-yl]benzonitrile (I-32) was synthesized according to the procedure described in Scheme 1 using alternative aldol conditions according to Scheme 1.5.

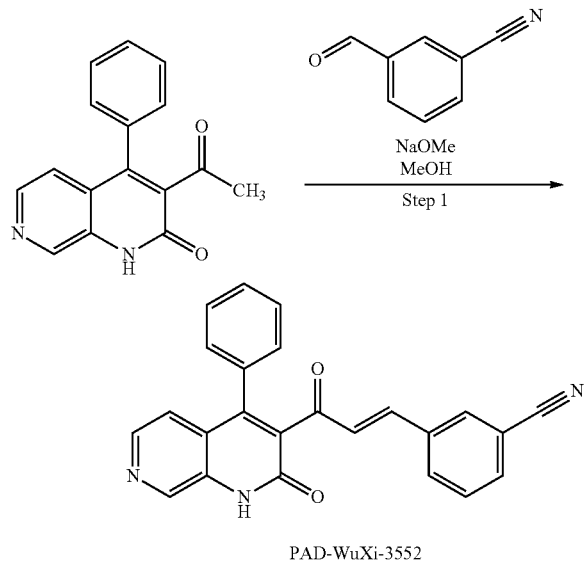

3-[(1E)-3-oxo-3-(2-oxo-4-phenyl-1,2-dihydro-1,7-naphthyridin-3-yl)prop-1-en-1-yl]benzonitrile (EW3861-144)—Step 1

To a solution of 3-acetyl-4-phenyl-1,2-dihydro-1,7-naphthyridin-2-one (1.00 g, 3.78 mmol) in MeOH (10.00 ml) was added 3-formylbenzonitrile (545.24 mg, 4.16 mmol) and sodium methoxide (408.39 mg, 7.56 mmol). The mixture was stirred at 20° C. for 2 hr. Saturated NH$_4$Cl (50 ml) and DCM (50 ml) was added to the solution then extracted with DCM (2×50 ml). The combined organic phase was concentrated in vacuo. The residue was purified by Basic HPLC preparative method B. A white precipitate was formed after acetonitrile was removed in vacuo. The mixture was filtered to afford 3-[(1E)-3-oxo-3-(2-oxo-4-phenyl-1,2-dihydro-1,7-naphthyridin-3-yl)prop-1-en-1-yl]benzonitrile (EW3861-144) (217 mg, 14%) as a yellow solid. LCMS (method G): retention time 2.74 min, M/z=378 (M+1).

Example 7. Synthesis of 4-phenyl-3-[(2E)-3-(pyrimidin-5-yl)prop-2-enoyl]-1,2-dihydro-1,6-naphthyridin-2-one, I-90

4-phenyl-3-[(2E)-3-(pyrimidin-5-yl)prop-2-enoyl]-1,2-dihydro-1,6-naphthyridin-2-one (I-90) (EOAI3454392) was synthesized according to the procedures described in Scheme 1 via 3-benzoylpyridin-4-amine (EV-AT 1790-001) synthesized according to Scheme 1.6

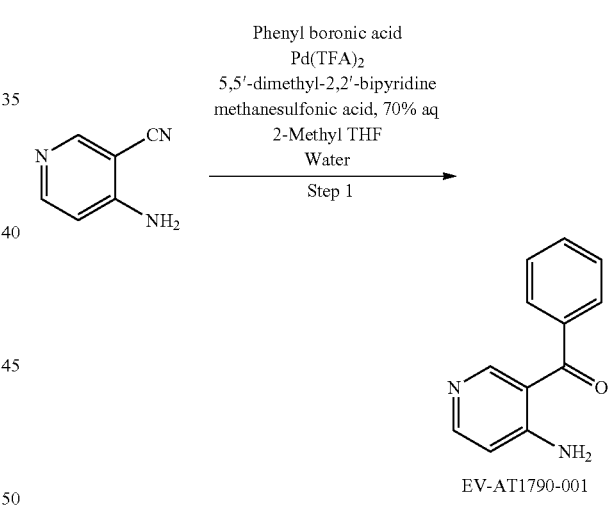

3-benzoylpyridin-4-amine (EV-AT1790-001)—Step 1

To a round-bottomed flask was added 4-aminopyridine-3-carbonitrile (500 mg, 4.2 mmol), phenylboronic acid (1023.6 mg, 8.4 mmol), Pd(TFA)$_2$ (69.8 mg, 0.2 mmol), 5,5'-dimethyl-2,2'-bipyridine (58 mg, 0.3 mmol), methanesulfonic acid, 70% aq (70%, 5762.7 mg, 42 mmol), 2-methyl-THF (10 ml) and water (5 ml). The mixture was heated to 80° C. under N$_2$ for 4 h. The mixture was cooled to room temperature, neutralized with saturated NaHCO$_3$ (aq) and extracted into EtOAc (2×30 ml). The combined organics were concentrated in vacuo and the crude yellow oil purified by flash column chromatography (0-20% MeOH in EtOAc) to afford 501 mg (60%) of 3-benzoylpyridin-4- amine (EV-AT1790-001) as a white crystalline solid. LCMS (method B): retention time 1.40 min, M/z=199.2 (M+1).

Example 8. Synthesis of 4-(4-methylphenyl)-3-[(2E)-3-(pyrimidin-5-yl)prop-2-enoyl]-1,2-dihydroquinolin-2-one, I-96

4-(4-methylphenyl)-3-[(2E)-3-(pyrimidin-5-yl)prop-2-enoyl]-1,2-dihydroquinolin-2-one (I-96) (EOAI3452879) was synthesized according to the procedure described in Scheme 1.2 via 3-acetyl-4-(4-methylphenyl)-1,2-dihydroquinolin-2-one (EV-AT8350-002) synthesized according to Scheme 1.7

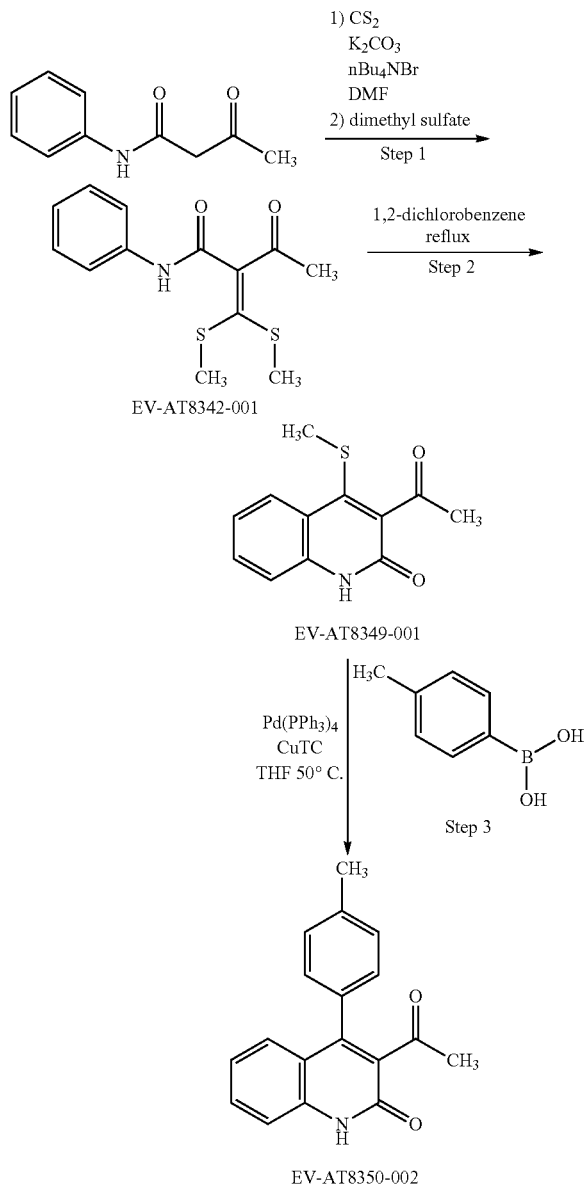

2-[bis(methylsulfanyl)methylidene]-3-oxo-N-phenylbutanamide (EV-AT8342-001)—Step 1

To a stirred solution of 3-oxo-N-phenylbutanamide (CAS 102-01-2, 18 g, 101.58 mmol) in DMF (100 ml) was added potassium carbonate (42.12 g, 304.74 mmol) followed by N,N,N-tributylbutan-1-aminium bromide (2.85 ml, 10.16 mmol). The suspension was stirred for 30 min before methanedithione (6.14 ml, 101.58 mmol) was added in one portion and the mixture was stirred at room temperature for 2h. Dimethylsulfate (21.19 ml, 223.48 mmol) was added and portion-wise over 30 min and once the addition was complete the mixture was stirred at room temperature for 4h. The mixture was then poured onto ice and the resulting solid was collected by filtration, washing with ice cold methanol (2×30 ml) to afford 31 g (quant) of 2-[bis(methylsulfanyl)methylidene]-3-oxo-N-phenylbutanamide (EV-AT8342-001) as a white crystalline solid. LCMS (method D): retention time 1.06 min, M/z=282 (M+1).

3-acetyl-4-(methylsulfanyl)-1,2-dihydroquinolin-2-one (EV-AT8349-001)—Step 2

A stirred suspension of 2-[bis(methylsulfanyl)methylidene]-3-oxo-N-phenylbutanamide (EV-AT8342-001, 5.0 g, 17.8 mmol) in orthodichlorobenzene (20 ml) was heated at 180° C. for 4h. The mixture was allowed to cool to room temperature and the solid was collected by filtration, washed with $Et_2O$ and dried under vacuum to afford 3.49 g (84.2%) of 3-acetyl-4-(methylsulfanyl)-1,2-dihydroquinolin-2-one (EV-AT8349-001) as a beige solid. LCMS (method D): retention time 0.88 min, M/z=234 (M+1).

3-acetyl-4-(4-methylphenyl)-1,2-dihydroquinolin-2-one (EV-AT8350-002)—Step 3

A stirred suspension of 3-acetyl-4-(methylsulfanyl)-1,2-dihydroquinolin-2-one (EV-AT8349-001, 240 mg, 1.03 mmol), (4-methylphenyl)boronic acid (95%, 161.95 mg, 1.13 mmol) and copper(I)-thiophene-2-carboxylate (97%, 262.91 mg, 1.34 mmol) in anhydrous THF (5 ml) was degassed via a stream of nitrogen. Tetrakis(triphenylphosphine)palladium (59.44 mg, 0.05 mmol) was added and the mixture was further degassed via a stream of nitrogen then heated at 50° C. for 16 h. The suspension was allowed to cool to room temperature, diluted with ether (30 ml) and aqueous ammonia (10%, 30 ml). The suspension was filtered through a pad of Kieselguhr and washed through with EtOAc. The filtrate layers were separated and the organic layer was washed with further aqueous ammonia until the aqueous became colourless. The organic later was dried over $MgSO_4$ and concentrated in vacuo and the resulting solid was triturated with EtOAc to obtain 105 mg (36.8%) of 3-acetyl-4-(4-methylphenyl)-1,2-dihydroquinolin-2-one (EV-AT8350-002) as a buff solid. LCMS (method D): retention time 0.99 min, M/z=278 (M+1).

Example 9. Synthesis of 3-[(2E)-3-(4-methoxyphenyl)prop-2-enoyl]-4-methyl-1,2-dihydroquinolin-2-one, I-132

3-[(2E)-3-(4-methoxyphenyl)prop-2-enoyl]-4-methyl-1,2-dihydroquinolin-2-one (I-132) (EOAI3440972) was synthesized according to the procedure described in Scheme 1 via 3-acetyl-4-methyl-1,2-dihydroquinolin-2-one (EV-AR9022-001) synthesized according to Scheme 1.8.

Scheme 1.8

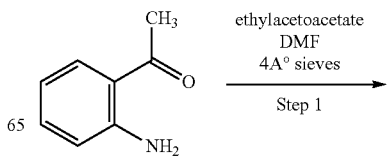

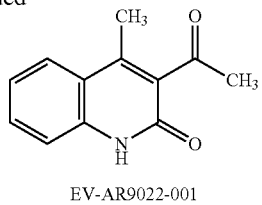

EV-AR9022-001

3-acetyl-4-methyl-1,2-dihydroquinolin-2-one (EV-AR9022-001)—Step 1

To a mixture of 1-(2-aminophenyl)ethan-1-one (CAS 551-93-9, 899.28 µl, 7.4 mmol) and ethyl 3-oxobutanoate (1.4 ml, 11.1 mmol) in DMF (15 ml) was added 4A molecular sieves (230 mg, 230 mmol). The reaction was stirred at 180° C. in a microwave for 30 min. Additional ethyl 3-oxobutanoate (0.5 ml, 36.9 mmol) was added and the reaction stirred at 180° C. in a microwave for 30 min. The reaction mixture was allowed to cool to room temperature and the solid was filtered off and washed with water. The solid was then dissolved in hot MeOH and filtered. The filtrate was then concentrated in vacuo to obtain 1.21 g (76.4%) of 3-acetyl-4-methyl-1,2-dihydroquinolin-2-one (EV-AR9022-001) as a white solid. LCMS (method D): retention time 0.99 min, M/z=202 (M+1).

Example 10. Synthesis of 3-[(2E)-3-(pyridin-3-yl)prop-2-enoyl]-1,2-dihydroquinolin-2-one, I-134

3-[(2E)-3-(pyridin-3-yl)prop-2-enoyl]-1,2-dihydroquinolin-2-one (I-134) (EOAI3440972) was synthesized according to the procedure described in Scheme 1 via 3-acetyl-1,2-dihydroquinolin-2-one (EV-AQ3892-001) synthesized according to Scheme 1.9.

Scheme 1.9

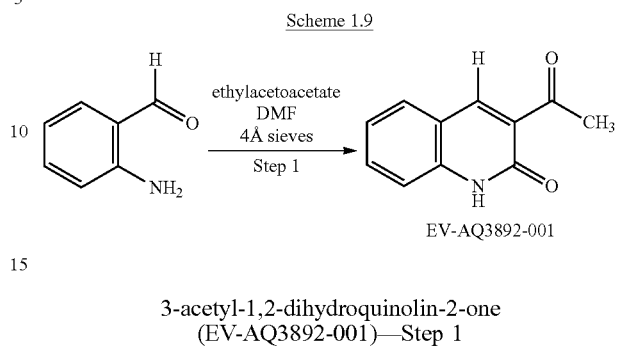

EV-AQ3892-001

3-acetyl-1,2-dihydroquinolin-2-one (EV-AQ3892-001)—Step 1

A solution of 2-aminobenzaldehyde (CAS 529-23-7, 900 mg, 7.43 mmol), ethyl 3-oxobutanoate (1409.48 µl, 11.14 mmol) and 4A molecular sieves (378 mg) in DMF (10 ml) was stirred in a microwave at 180° C. for 30 min. A beige precipitate has formed during the reaction. The resulting suspension was diluted with ether and the solids were collected by filtration, washed with ether. The solid was washed with ether dried under vacuum to obtain 1300 mg (93.5%) of 3-acetyl-1,2-dihydroquinolin-2-one (EV-AQ3892-001) as a beige powder. LCMS (method D): retention time 0.92 min, M/z=188 (M+1).

Example 11. Synthesis of (2E)-1-(4-phenylquinolin-3-yl)-3-(pyridin-2-yl)prop-2-en-1-one, I-147

(2E)-1-(4-phenylquinolin-3-yl)-3-(pyridin-2-yl)prop-2-en-1-one (I-147) (EOAI3452072) was synthesized according to Scheme 1.10.

Scheme 1.10

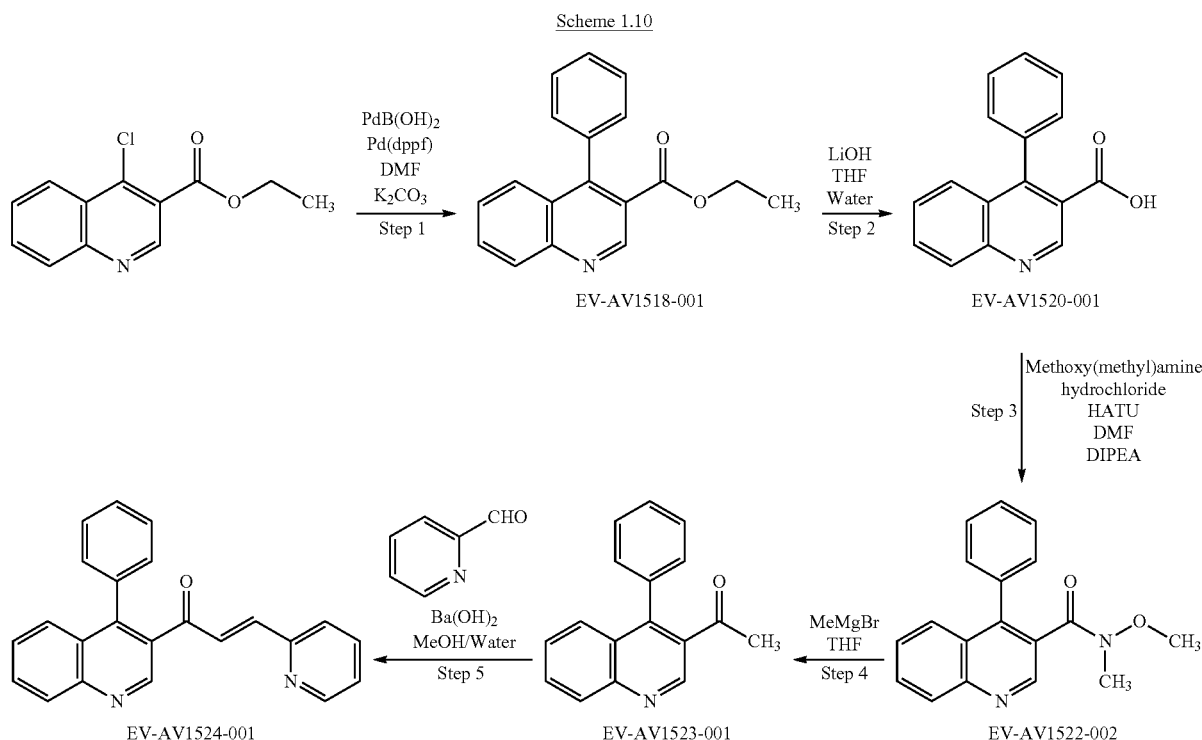

Ethyl 4-phenylquinoline-3-carboxylate (EV-AV1518-001)—Step 1

Ethyl 4-chloroquinoline-3-carboxylate (CAS 13720-94-0, 450 mg, 1.91 mmol), phenylboronic acid (349.23 mg, 2.86 mmol) and potassium carbonate (791.7 mg, 5.73 mmol) were combined in DMF (15 ml). The solution was thoroughly degassed using nitrogen before adding 1,1'-bis(diphenylphosphanyl)ferrocene dichloropalladium (1:1) (139.72 mg, 0.19 mmol). The solution was stirred at 110° C. for 5h. The reaction mixture was allowed to cool to room temperature, diluted with water and EtOAc and filtered through a pad of Kieselguhr. The aqueous phase was washed with EtOAc and the combined organics were dried over $MgSO_4$ and concentrated in vacuo. The residue was purified by flash column chromatography (12-100% EtOAc/heptane) to obtain 370 mg (60.4%) of ethyl 4-phenylquinoline-3-carboxylate (EV-AV1518-001) as a light pink solid. LCMS (method D): retention time 1.25 min, M/z=278 (M+1).

4-phenylquinoline-3-carboxylic acid (EV-AV1520-001)—Step 2

Lithium hydroxide (270.70 mg, 11.08 mmol) was added to a solution of ethyl 4-phenylquinoline-3-carboxylate (320 mg, 1.108 mmol) in THF (3 ml) and water (3 ml). The resulting mixture was stirred at 60° C. for 2h. The reaction was allowed to cool to room temperature and acidified with 1M aqueous HCl (12 ml) at which point a white precipitate formed. The reaction was then concentrated in vacuo and the solid dried in a vacuum oven for 17h to obtain 750 mg (quant) of 4-phenylquinoline-3-carboxylic acid (EV-AV1520-001) as a white solid. LCMS (method D): retention time 0.98 min, M/z=250 (M+1).

N-methoxy-N-methyl-4-phenylquinoline-3-carboxamide (EV-AV1522-002)—Step 3

To a stirred solution of 4-phenylquinoline-3-carboxylic acid (EV-AV1520-001, 37%, 750 mg, 1.11 mmol), HATU (825.44 mg, 2.17 mmol) and DIPEA (465.39 µl, 2.67 mmol) in DMF (2 ml), was added methoxy(methyl)amine hydrochloride (179.18 mg, 1.84 mmol) and the resulting mixture was stirred at room temperature for 3h. The reaction mixture was purified by acidic preparative HPLC and the wet fractions were partially concentrated in vacuo. The remaining aqueous mixture was neutralized with $NaHCO_3$ (aq) and extracted with DCM (3×10 ml). The organic layer was collected, dried over $MgSO_4$ and concentrated in vacuo to obtain 119 mg (36.6%) of N-methoxy-N-methyl-4-phenylquinoline-3-carboxamide (EV-AV1522-002) as a white solid. LCMS (method D): retention time 1.06 min, M/z=293 (M+1).

1-(4-phenylquinolin-3-yl)ethan-1-one (EV-AV1523-001)—Step 4

To a stirred solution of N-methoxy-N-methyl-4-phenylquinoline-3-carboxamide (EV-AV1521-001 and EV-AV1522-002, 152 mg, 0.52 mmol) in anhydrous THF (3 ml) under nitrogen at 0° C. was added 3M bromo(methyl)magnesium in $Et_2O$ (173.32 µl, 0.52 mmol). The reaction was stirred at 0° C. for 1 h then 3M bromo(methyl)magnesium in $Et_2O$ (86.66 µl, 0.27 mmol) was added. The reaction was stirred at 0° C. for 1.5h. The reaction was quenched with $NaHCO_3$ (aq, 1 ml) then diluted with EtOAc (50 ml) and water (50 ml). The aqueous layer was extracted with EtOAc (2×15 ml) and the combined organics were washed with brine (2×50 ml), dried over $MgSO_4$ and concentrated in vacuo. The crude was purified by flash column chromatography (12-100% EtOAc/heptane) to obtain 98.9 mg (76.1%) of 1-(4-phenylquinolin-3-yl)ethan-1-one (EV-AV1523-001) as a colourless oil. LCMS (method D): retention time 1.14 min, M/z=248 (M+1).

(2E)-1-(4-phenylquinolin-3-yl)-3-(pyridin-2-yl)prop-2-en-1-one (I-147) (EV-AV1524-001)—Step 5

A solution of pyridine-2-carbaldehyde (106.02 mg, 0.99 mmol) in MeOH (1 ml) was added slowly to a solution of barium dihydroxide (95%, 71.41 mg, 0.4 mmol) in water (0.08 ml). A solution of 1-(4-phenylquinolin-3-yl)ethan-1-one (98.9 mg, 0.4 mmol) in MeOH (5 ml) was then added to slowly to the reaction mixture. The reaction was stirred at room temperature for 1 h. The reaction mixture was acidified to pH 5.5 with acetic acid and diluted with DCM and water. The aqueous layer was extracted with DCM and the combined organics were dried over MgSO4 and concentrated in vacuo. The crude was purified by acidic preparative HPLC and the fractions freeze dried overnight to obtain 16.4 mg (11.6%) of (2E)-1-(4-phenylquinolin-3-yl)-3-(pyridin-2-yl)prop-2-en-1-one (I-147) (EV-AV1524-001) as a pale yellow solid. LCMS (method A): retention time 3.23 min, M/z=337 (M+1).

Example 12. Synthesis of 1-(2-hydroxyethyl)-4-phenyl-3-[(2E)-3-(pyrimidin-5-yl)prop-2-enoyl]-1,2-dihydroquinolin-2-one, I-71 and (2E)-1-[2-(2-hydroxyethoxy)-4-phenylquinolin-3-yl]-3-(pyrimidin-5-yl)prop-2-en-1-one, I-140

1-(2-hydroxyethyl)-4-phenyl-3-[(2E)-3-(pyrimidin-5-yl)prop-2-enoyl]-1,2-dihydroquinolin-2-one (I-71) (EOAI34-54965) and (2E)-1-[2-(2-hydroxyethoxy)-4-phenylquinolin-3-yl]-3-(pyrimidin-5-yl)prop-2-en-1-one (I-140) (EOAI345-4966) were synthesized according to the procedure described in Scheme 2 via 4-phenyl-3-[(2E)-3-(pyrimidin-5-yl)prop-2-enoyl]-1,2-dihydroquinolin-2-one (EV-AV97-00-001) synthesized according to Scheme 1.1.

Scheme 2

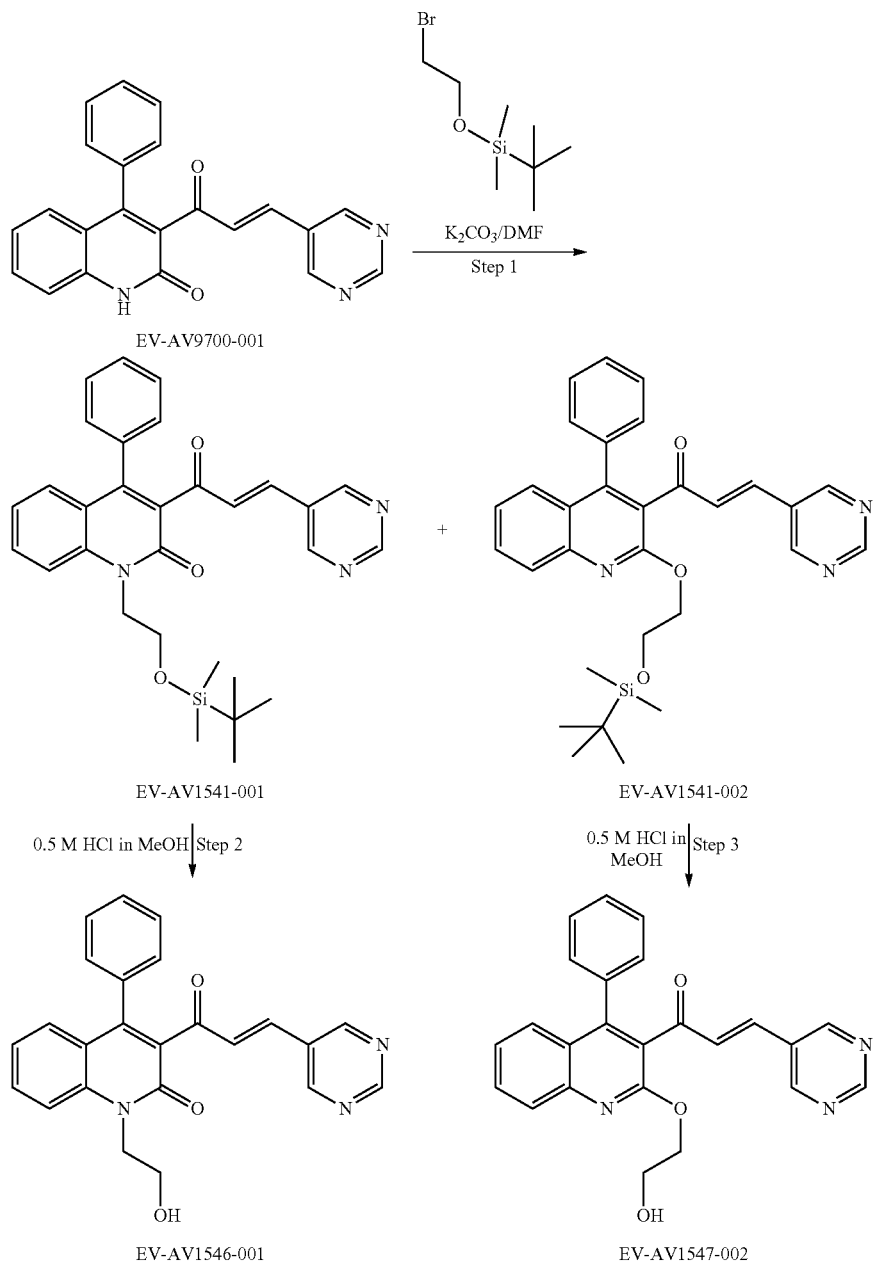

1-{2-[(tert-butyldimethylsilyl)oxy]ethyl}-4-phenyl-3-[(2E)-3-(pyrimidin-5-yl)prop-2-enoyl]-1,2-dihydroquinolin-2-one (EV-AV1541-001) and (2E)-1-(2-{2-[(tert-butyldimethylsilyl)oxy]ethoxy}-4-phenylquinolin-3-yl)-3-(pyrimidin-5-yl)prop-2-en-1-one (EV-AV1541-002)—Step 1

To a solution of 4-phenyl-3-[(2E)-3-(pyrimidin-5-yl)prop-2-enoyl]-1,2-dihydroquinolin-2-one (EV-AV9700-001, 200 mg, 0.57 mmol) in DMF (anhydrous, 3 ml) was added (2-bromoethoxy)(tert-butyl)dimethylsilane (145.72 µl, 0.68 mmol) and K₂CO₃ (93.86 mg, 0.68 mmol). The reaction was stirred at room temperature for 25h then at 60° C. for 21h. The reaction mixture was diluted with water (25 ml) and extracted with EtOAc (25 ml). The aqueous layer was then extracted using EtOAc (3×25 ml). The combined organics were dried over MgSO₄, filtered and concentrated in vacuo. The crude material was purified by flash column chromatography (20-100% EtOAc in heptane) to obtain 2 products. 145 mg (47.1%) of 1-{2-[(tert-butyldimethylsilyl)oxy]ethyl}-4-phenyl-3-[(2E)-3-(pyrimidin-5-yl)prop-2-enoyl]-1,2-dihydroquinolin-2-one (EV-AV1541-001) as a yellow solid. LCMS (method D): retention time 1.43 min, M/z=512 (M+1). And 38.5 mg (12.9%) of (2E)-1-(2-{2-[(tert-butyldimethylsilyl)oxy]ethoxy}-4-phenylquinolin-3-yl)-3-(pyrimidin-5-yl)prop-2-en-1-one (EV-AV1451-002) as a white solid. LCMS (method D): retention time 1.57 min, M/z=512 (M+1).

1-(2-hydroxyethyl)-4-phenyl-3-[(2E)-3-(pyrimidin-5-yl)prop-2-enoyl]-1,2-dihydroquinolin-2-one (I-71) (EV-AV1546-001)—Step 2

0.5M hydrogen chloride in MeOH (1500 μl) was added to 1-{2-[(tert-butyldimethylsilyl)oxy]ethyl}-4-phenyl-3-[(2E)-3-(pyrimidin-5-yl)prop-2-enoyl]-1,2-dihydroquinolin-2-one (EV-AV1541-001, 130 mg, 0.239 mmol). The reaction was stirred at room temperature for 30 min. The residue was neutralized using saturated NaHCO$_3$ (to pH 7.5) then partitioned between water (60 ml) and DCM (60 ml). The organic layer was dried over MgSO$_4$ and concentrated in vacuo. The material was then dissolved in acetonitrile: water (1:1, 4 ml) and freeze dried to obtain 75 mg (77.4%) of 1-(2-hydroxyethyl)-4-phenyl-3-[(2E)-3-(pyrimidin-5-yl)prop-2-enoyl]-1,2-dihydroquinolin-2-one (I-71)(EV-AV1546-001) as a yellow powder. LCMS (method A): retention time 2.53 min, M/z=398 (M+1).

(2E)-1-[2-(2-hydroxyethoxy)-4-phenylquinolin-3-yl]-3-(pyrimidin-5-yl)prop-2-en-1-one (I-140) (EV-AV1547-002)—Step 3

0.5M hydrogen chloride in MeOH (1500 μl) was added to (2E)-1-(2-{2-[(tert-butyldimethylsilyl)oxy]ethoxy}-4-phenylquinolin-3-yl)-3-(pyrimidin-5-yl)prop-2-en-1-one (EV-AV1541-002, 38 mg, 0.072 mmol). The reaction was stirred at room temperature for 30 min. The residue was neutralized using saturated NaHCO$_3$ (to pH 7.5) then partitioned between water (30 ml) and DCM (30 ml). The organic layer was dried over MgSO$_4$ and concentrated in vacuo. The crude material was purified by Basic HPLC preparative method A and the fractions freeze dried to obtain 5.2 mg (52.6%) of (2E)-1-[2-(2-hydroxyethoxy)-4-phenylquinolin-3-yl]-3-(pyrimidin-5-yl)prop-2-en-1-one (I-140) (EV-AV1547-002) as an off-white solid. LCMS (method A): retention time 3.06 min, M/z=398 (M+1).

Special Cases for Scheme 2

Example 13. Synthesis of 3-{6-fluoro-2-oxo-4-phenyl-3-[(2E)-3-(pyridin-3-yl)prop-2-enoyl]-1,2-dihydroquinolin-1-yl}propanenitrile, I-22

3-{6-fluoro-2-oxo-4-phenyl-3-[(2E)-3-(pyridin-3-yl)prop-2-enoyl]-1,2-dihydroquinolin-1-yl}propanenitrile (I-22) (EOAI3458671) was synthesized according to the procedures described in Scheme 1 using alternative alkylation conditions according to Scheme 2.1

Scheme 2.1

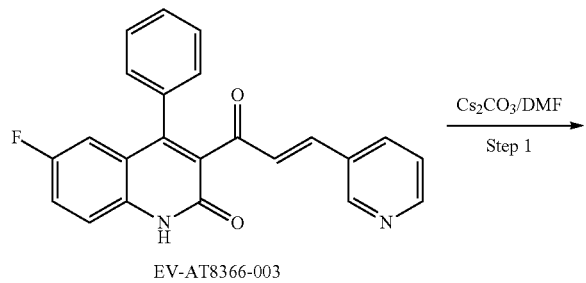

EV-AT8366-003

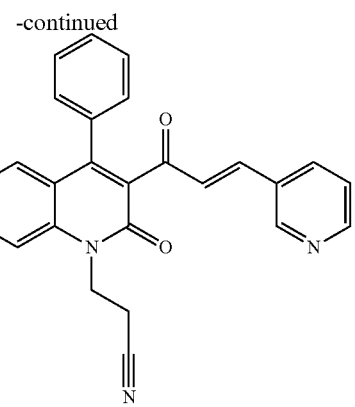

3-{6-fluoro-2-oxo-4-phenyl-3-[(2E)-3-(pyridin-3-yl)prop-2-enoyl]-1,2-dihydroquinolin-1-yl} propanenitrile (EV-AT8369-002)—Step 1

Cesium carbonate (123 mg, 0.38 mmol) was added to a solution of 6-fluoro-4-phenyl-3-[(2E)-3-(pyridin-3-yl)prop-2-enoyl]-1,2-dihydroquinolin-2-one (EV-AT8366-003, 50 mg, 0.14 mmol) in DMF (1 ml). The mixture was stirred at room temperature for 60 min before 3-bromopropanenitrile (22.47 μl, 0.27 mmol) was added. The reaction was stirred for 1 h at RT, followed by 50° C. for 16 h. Additional 3-bromopropanenitrile (11 μl, 0.13 mmol) was added and the reaction was continued at 50° C. for 3 h. Additional 3-bromopropanenitrile (11 μl, 0.13 mmol) was added and the mixture was heated at 50° C. for 16 h. The reaction mixture was re-treated with cesium carbonate (62 mg, 0.19 mmol) and 3-bromopropanenitrile (11 μl, 0.13 mmol) and continued heating at 50° C. for 3 h. The mixture was evaporated in vacuo, the residue was diluted with water and extracted with EtOAc (×2). The extracts were washed with brine, dried over MgSO$_4$ and concentrated in vacuo to afford a brown residue. The crude material was purified by flash column chromatography (EtOAc) to afford 27 mg (44%) of 3-{6-fluoro-2-oxo-4-phenyl-3-[(2E)-3-(pyridin-3-yl)prop-2-enoyl]-1,2-dihydroquinolin-1-yl}propanenitrile (I-22) (EV-AT8369-002) as a buff solid. LCMS (method A): retention time 2.82 min, M/z=424.2 (M+1).

Example 14. Synthesis of 1-(2-methoxyethyl)-4-phenyl-3-[(2E)-3-(pyrimidin-5-yl)prop-2-enoyl]-1,2-dihydroquinolin-2-one, I-81 and (2E)-1-[2-(2-methoxyethoxy)-4-phenylquinolin-3-yl]-3-(pyrimidin-5-yl)prop-2-en-1-one, I-144

1-(2-methoxyethyl)-4-phenyl-3-[(2E)-3-(pyrimidin-5-yl)prop-2-enoyl]-1,2-dihydroquinolin-2-one (I-81) (EOAI3454650) and (2E)-1-[2-(2-methoxyethoxy)-4-phenylquinolin-3-yl]-3-(pyrimidin-5-yl)prop-2-en-1-one (I-144) (EOAI3454651) were synthesized according to Scheme 2.2 via 4-phenyl-3-[(2E)-3-(pyrimidin-5-yl)prop-2-enoyl]-1,2-dihydroquinolin-2-one (EV-AV9700-001) synthesized via the procedure described Scheme 1.1.

141

Scheme 2.2

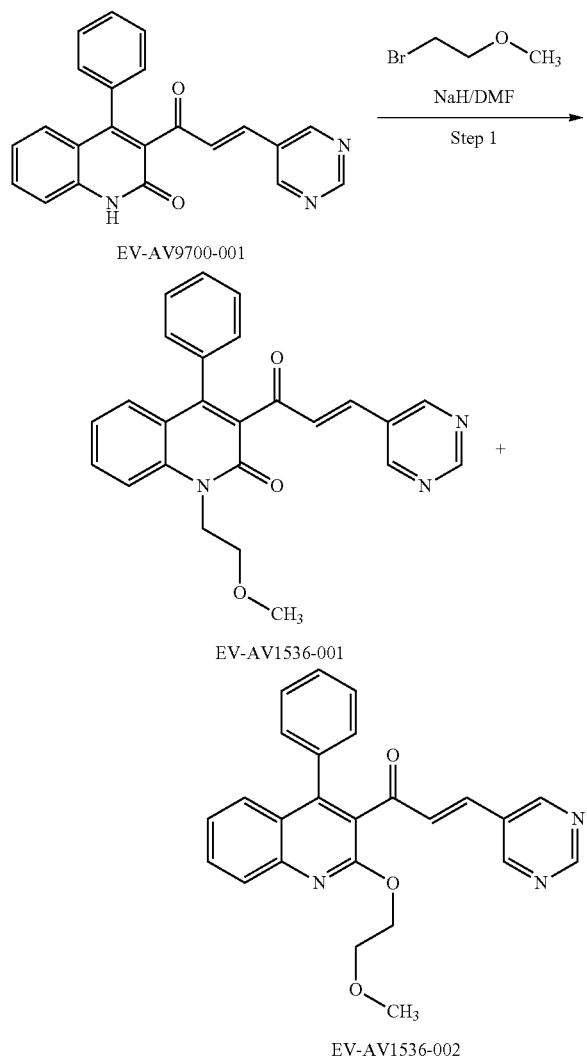

EV-AV9700-001

EV-AV1536-001

EV-AV1536-002

1-(2-methoxyethyl)-4-phenyl-3-[(2E)-3-(pyrimidin-5-yl)prop-2-enoyl]-1,2-dihydroquinolin-2-one (I-81) (EV-AV-1536-001) and (2E)-1-[2-(2-methoxyethoxy)-4-phenylquinolin-3-yl]-3-(pyrimidin-5-yl)prop-2-en-1-one (I-144) (EV-AV1536-002)—Step 1

To a flask containing NaH (16.3 mg, 0.68 mmol) was added a solution of 4-phenyl-3-[(2E)-3-(pyrimidin-5-yl)prop-2-enoyl]-1,2-dihydroquinolin-2-one (EV-AV9700-001, 200 mg, 0.57 mmol) in anhydrous DMF (3 ml) and 1-bromo-2-methoxyethane (105 μl, 1.12 mmol). The reaction was stirred at RT for 23 h, quenched with water (10 ml) and extracted using EtOAc (3×25 ml). The combined organics were dried over MgSO₄, filtered and concentrated in vacuo to give an orange oil which was purified by acidic preparative HPLC. The fractions containing product were combined and concentrated in vacuo to give an orange solid (EV-AV1536-001) and an off-white solid (EV-AV1536-002). The products were dissolved in acetonitrile/water and dried by lyophilization to afford 1-(2-methoxyethyl)-4-phenyl-3-[(2E)-3-(pyrimidin-5-yl)prop-2-enoyl]-1,2-dihydroquinolin-2-one (I-81) (EV-AV1536-001) (87.3 mg, 36.4%)

142 as a pale pink solid. LCMS (method A): retention time 2.99 min, M/z=412 (M+1). And (2E)-1-[2-(2-methoxyethoxy)-4-phenylquinolin-3-yl]-3-(pyrimidin-5-yl)prop-2-en-1-one (I-144)(EV-AV1536-002) (34.2 mg, 14.4%) as an off-white solid. LCMS (method A): retention time 3.60 min, M/z=412 (M+1).

Example 15. Synthesis of (2E)-1-(2-methoxy-4-phenylquinolin-3-yl)-3-(pyridin-2-yl)prop-2-en-1-one, I-145

(2E)-1-(2-methoxy-4-phenylquinolin-3-yl)-3-(pyridin-2-yl)prop-2-en-1-one (I-145) (EOAI3452070) was synthesized according to the procedure described in Scheme 2.3 via 4-phenyl-3-[(2E)-3-(pyridin-2-yl)prop-2-enoyl]-1,2-dihydroquinolin-2-one (EV-AT1787-002) synthesized according to Scheme 1.2.

Scheme 2.3

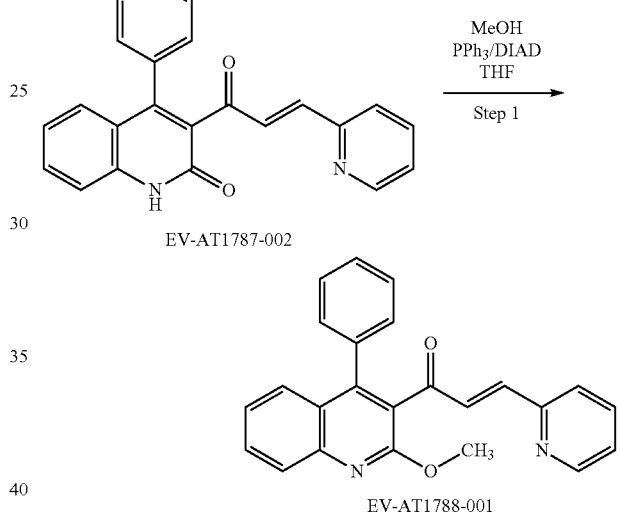

EV-AT1787-002

EV-AT1788-001

(2E)-1-(2-methoxy-4-phenylquinolin-3-yl)-3-(pyridin-2-yl)prop-2-en-1-one (I-145) (EV-AT1788-001)—Step 1

To a suspension of 4-phenyl-3-[(2E)-3-(pyridin-2-yl)prop-2-enoyl]-1,2-dihydroquinolin-2-one (100 mg, 0.28 mmol) in anhydrous THF (2 ml) was added methanol (34.44 μl, 0.85 mmol), triphenylphosphine (0.22 g, 0.85 mmol) and DIAD (0.17 ml, 0.85 mmol). The mixture was stirred overnight. The mixture was diluted with water (10 ml) and extracted with DCM (2×10 ml). The combined organics were evaporated to dryness and purification was performed by the Acidic HPLC preparative method to afford 1-methyl-4-phenyl-3-[(2E)-3-(pyridin-2-yl)prop-2-enoyl]-1,2-dihydroquinolin-2-one (I-145) (EV-AT1788-001) (17 mg, 16%) as a yellow powder. LCMS (method A): retention time 3.13 min, M/z=367 (M+1).

Example 16. Synthesis of 1-methyl-4-phenyl-3-[(2E)-3-(pyridin-2-yl)prop-2-enoyl]-1,2-dihydroquinolin-2-one, I-119

1-methyl-4-phenyl-3-[(2E)-3-(pyridin-2-yl)prop-2-enoyl]-1,2-dihydroquinolin-2-one (I-119) (EOAI3447733) was synthesized according to the procedure described in Scheme 1 via 3-acetyl-1-methyl-4-phenyl-1,2-dihydroquinolin-2-one (EV-AR9073-001) synthesized according to Scheme 2.4.

enoyl]-1,2-dihydroquinolin-2-one (EV-AV9700-002) synthesized according to Scheme 1.1.

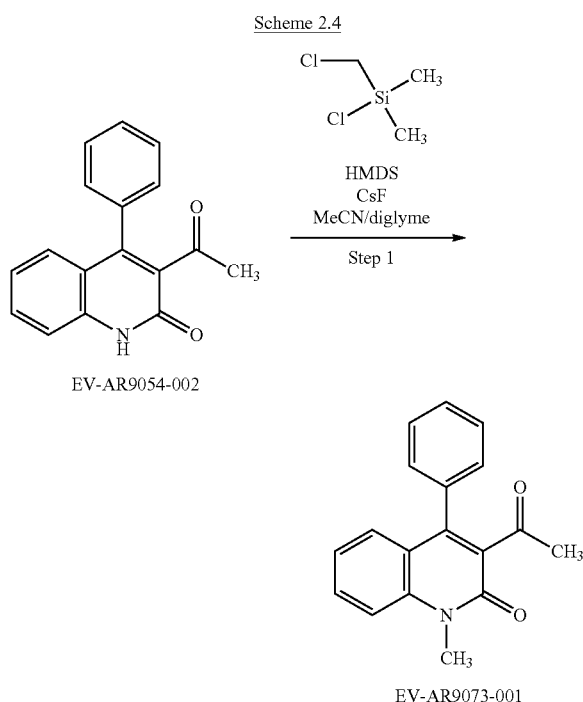

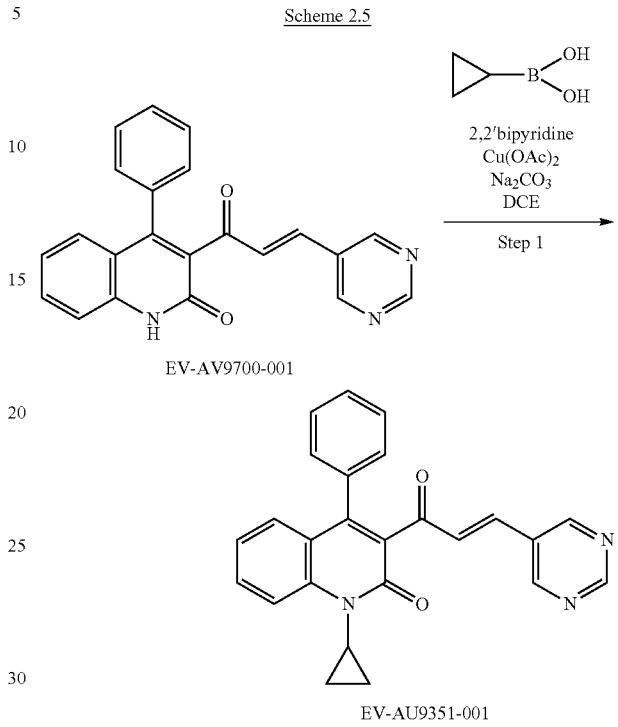

3-acetyl-1-methyl-4-phenyl-1,2-dihydroquinolin-2-one (EV-AR9073-001)—Step 1

To a suspension of 3-acetyl-4-phenyl-1,2-dihydroquinolin-2-one (1 g, 3.8 mmol) in anhydrous acetonitrile (30 ml) was added HMDS (500 μl, 2.39 mmol), and the resultant mixture was heated at 80° C. for 3.5 h. The reaction was cooled to RT, chloro(chloromethyl)dimethylsilane (500.42 μl, 3.8 mmol) was added and the reaction mixture was heated at 80° C. for 17h. Additional chloro(chloromethyl) dimethylsilane (100 μl, 0.76 mmol) was added at RT and the reaction heated at 80° C. for 1 h. The reaction mixture was cooled to RT and concentrated in vacuo to afford a yellow solid. The solid was then suspended in anhydrous 2-methoxyethyl ether (diglyme) (30 ml), treated with cesium fluoride (807.72 mg, 5.32 mmol) and stirred at 150° C. for 1 h. The reaction was cooled in an ice bath, quenched with water (100 ml), and left to stand in the ice bath overnight. The resulting solid was filtered and washed with water to afford 3-acetyl-1-methyl-4-phenyl-1,2-dihydroquinolin-2-one (EV-AR9073-001) (923 mg, 79%) as an orange solid. LCMS (method A): retention time 3.09 min, M/z=278 (M+1).

Example 17. Synthesis of 1-cyclopropyl-4-phenyl-3-[(2E)-3-(pyrimidin-5-yl)prop-2-enoyl]-1,2-dihydroquinolin-2-one, I-83

1-cyclopropyl-4-phenyl-3-[(2E)-3-(pyrimidin-5-yl)prop-2-enoyl]-1,2-dihydroquinolin-2-one (I-83) (EOAI3454648) was synthesized according to the procedure described in Scheme 2.5 via 4-phenyl-3-[(2E)-3-(pyrimidin-5-yl)prop-2-

1-cyclopropyl-4-phenyl-3-[(2E)-3-(pyrimidin-5-yl)prop-2-enoyl]-1,2-dihydroquinolin-2-one (I-83) (EV-AU9351-001)—Step 1

A mixture of 4-phenyl-3-[(2E)-3-(pyrimidin-5-yl)prop-2-enoyl]-1,2-dihydroquinolin-2-one (100 mg, 0.28 mmol), copper(II) acetate (55 mg, 0.3 mmol), 2,2'-bipyridine (47.29 mg, 0.3 mmol) $Na_2CO_3$ (68.08 mg, 0.64 mmol) and cyclopropylboronic acid (54.69 mg, 0.64 mmol) in DCE (2 ml) was stirred at 80° C. for 4.5h. The reaction mixture was diluted with DCM (15 ml) and saturated aqueous $NH_4Cl$ (10 ml). The organic layer was collected, dried over $Na_2SO_4$, and concentrated in vacuo. The residue was purified by the Acidic HPLC preparative method and the desired fractions were concentrated in vacuo to afford 1-cyclopropyl-4-phenyl-3-[(2E)-3-(pyrimidin-5-yl)prop-2-enoyl]-1,2-dihydroquinolin-2-one (I-83) (EV-AU9351-001) (54 mg, 48%) as an off white solid. LCMS (method A): retention time 3.07 min, M/z=394 (M+1).

Example 18. Synthesis of (2E)-1-[4-phenyl-2-(prop-2-en-1-yloxy)quinolin-3-yl]-3-(pyrimidin-5-yl)prop-2-en-1-one, I-142

(2E)-1-[4-phenyl-2-(prop-2-en-1-yloxy)quinolin-3-yl]-3-(pyrimidin-5-yl)prop-2-en-1-one (I-142) (EOAI3454809) was synthesized according to the procedure described in Scheme 2.6 via 4-phenyl-3-[(2E)-3-(pyrimidin-5-yl)prop-2-enoyl]-1,2-dihydroquinolin-2-one (EV-AV9700-002) synthesized according to Scheme 1.1.

Scheme 2.6

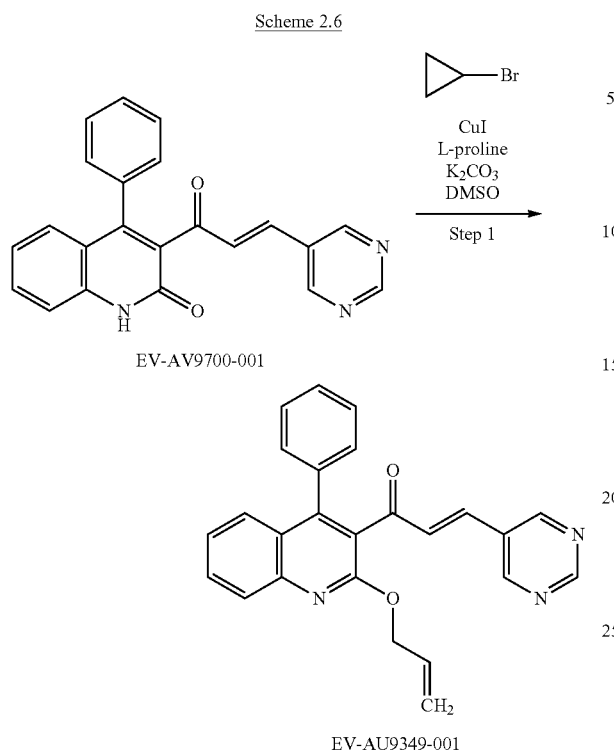

EV-AV9700-001

EV-AU9349-001

Scheme 2.7

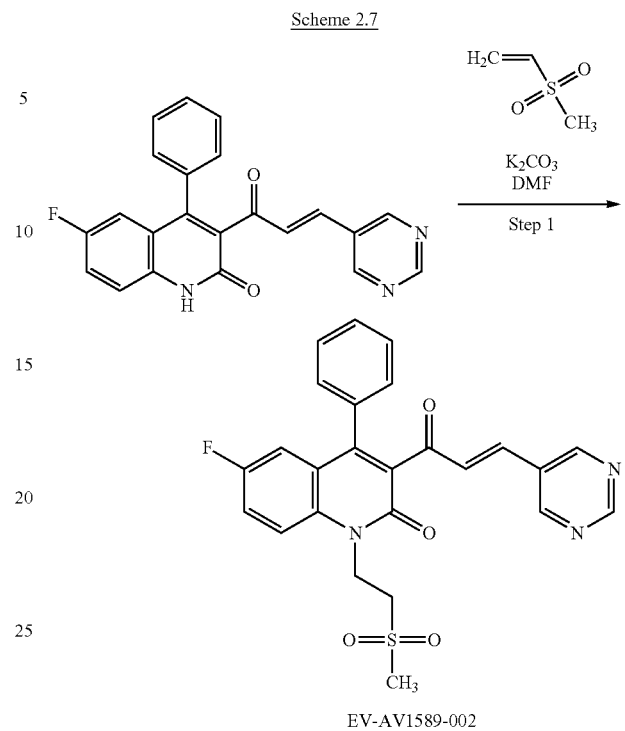

EV-AV1589-002

(2E)-1-[4-phenyl-2-(prop-2-en-1-yloxy)quinolin-3-yl]-3-(pyrimidin-5-yl)prop-2-en-1-one (I-142) (EV-AU9349-001)—Step 1

4-phenyl-3-[(2E)-3-(pyrimidin-5-yl)prop-2-enoyl]-1,2-dihydroquinolin-2-one (50 mg, 0.14 mmol), copper iodide (5.39 mg, 0.03 mmol), L-proline (6.52 mg, 0.06 mmol) and $K_2CO_3$ (39.11 mg, 0.28 mmol) were added to the reaction vessel. The vessel was placed under a nitrogen atmosphere and anhydrous DMSO (1 ml) was added. The reaction was heated to 90° C. and bromocyclopropane (22.6 µl, 0.28 mmol) was added. The reaction was stirred at 90° C. for 6.5h. The reaction was allowed to cool to room temperature and diluted with water (3 ml) and EtOAc (5 ml). The organic layer was collected, washed with brine (3 ml), dried over $Na_2SO_4$ and concentrated in vacuo. The residue was then purified acidic preparative HPLC and the desired fractions were concentrated in vacuo to afford (2E)-1-[4-phenyl-2-(prop-2-en-1-yloxy)quinolin-3-yl]-3-(pyrimidin-5-yl)prop-2-en-1-one (I-142) (EV-AU9349-001) (22 mg, 39.5%) as a pale beige solid. LCMS (method A): retention time 3.95 min, M/z=394 (M+1).

Example 19. Synthesis of 6-fluoro-1-(2-methanesulfonylethyl)-4-phenyl-3-[(2E)-3-(pyrimidin-5-yl)prop-2-enoyl]-1,2-dihydroquinolin-2-one, I-12

6-fluoro-1-(2-methanesulfonylethyl)-4-phenyl-3-[(2E)-3-(pyrimidin-5-yl)prop-2-enoyl]-1,2-dihydroquinolin-2-one (I-12) (EOAI3458988) was synthesized according to the procedure described in Scheme 1.1 using alternative alkylation conditions according to Scheme 2.7.

6-fluoro-1-(2-methanesulfonylethyl)-4-phenyl-3-[(2E)-3-(pyrimidin-5-yl)prop-2-enoyl]-1,2-dihydroquinolin-2-one (I-12) (EV-AV1589-002)—Step 1

To a 6-fluoro-4-phenyl-3-[(2E)-3-(pyrimidin-5-yl)prop-2-enoyl]-1,2-dihydroquinolin-2-one (150 mg, 0.37 mmol) of in DMF (3 ml) was added (methylsulfonyl)ethene (39 µL, 0.45 mmol) and potassium carbonate (77 mg, 0.56 mmol). The reaction was stirred at 80° C. for 2 h, then 100° C. for 16 h, before being cooled back down to 80° C. Additional (methylsulfonyl)ethene (20 µL, 0.22 mmol) was added and the reaction was stirred at 80° C. for 1 h. Further (methylsulfonyl)ethene (20 µL, 0.22 mmol) was added and the reaction was stirred at 80° C. for 1 h. Additional potassium carbonate (38 mg, 0.28 mmol) was added and the reaction was stirred at 80° C. for 2 h. The reaction was then quenched using water (25 ml) and the product was extracted using 10% MeOH in DCM (25 ml). The aqueous phase was extracted using 10% MeOH in DCM (3×25 ml). The combined organics were dried over $MgSO_4$ and concentrated in vacuo. The product was purified by preparative HPLC to afford 6-fluoro-1-(2-methanesulfonylethyl)-4-phenyl-3-[(2E)-3-(pyrimidin-5-yl)prop-2-enoyl]-1,2-dihydroquinolin-2-one (I-12) EV-AV1589-002) (10 mg, 5%) as a yellow solid. LCMS (method A): retention time 2.80 min, M/z=478 (M+1).

Example 20. Synthesis of 6-fluoro-1-(2-hydroxy-2-methylpropyl)-4-phenyl-3-[(2E)-3-(pyrimidin-5-yl)prop-2-enoyl]-1,2-dihydroquinolin-2-one, I-11

6-fluoro-1-(2-hydroxy-2-methylpropyl)-4-phenyl-3-[(2E)-3-(pyrimidin-5-yl)prop-2-enoyl]-1,2-dihydroquinolin-2-one (I-11) (EOAI3458989) was synthesized according to the procedure described in Scheme 1.1 using alternative alkylation conditions according to Scheme 2.8.

Scheme 2.8

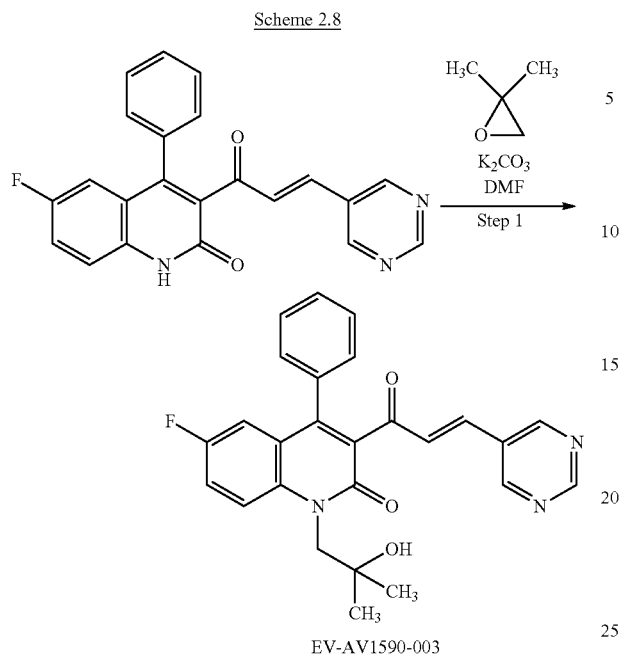

EV-AV1590-003

6-fluoro-1-(2-hydroxy-2-methylpropyl)-4-phenyl-3-[(2E)-3-(pyrimidin-5-yl)prop-2-enoyl]-1,2-dihydroquinolin-2-one (I-11) (EV-AV1590-003)—Step 1

To a solution of 6-fluoro-4-phenyl-3-[(2E)-3-(pyrimidin-5-yl)prop-2-enoyl]-1,2-dihydroquinolin-2-one (200 mg, 0.54 mmol) in DMF (3 ml) was added 2,2-dimethyloxirane (57.39 µL, 0.65 mmol) and potassium carbonate (89.32 mg, 0.65 mmol). The reaction was stirred at 120° C. in a microwave for 3 h. Additional 2,2-dimethyloxirane (25 µL) was added and the reaction was stirred at 120° C. in a microwave for 30 min. Further 2,2-dimethyloxirane (25 µL) was added and the reaction was stirred at 120° C. in a microwave for 30 min. The reaction mixture was concentrated in vacuo and purified using acidic preparative HPLC to afford 6-fluoro-1-(2-hydroxy-2-methylpropyl)-4-phenyl-3-[(2E)-3-(pyrimidin-5-yl)prop-2-enoyl]-1,2-dihydroquinolin-2-one (I-11) (EV-AV1590-003) (5.1 mg, 2%) as a brown solid. LCMS (method A): retention time 2.94 min, M/z=444 (M+1).

Example 21. Synthesis of 3-[(2E)-3-{6-[2-(dimethylamino)ethoxy]pyridin-3-yl}prop-2-enoyl]-6-fluoro-4-phenyl-1,2-dihydroquinolin-2-one, I-4

3-[(2E)-3-{6-[2-(dimethylamino)ethoxy]pyridin-3-yl}prop-2-enoyl]-6-fluoro-4-phenyl-1,2-dihydroquinolin-2-one (I-4) (EOAI3459612) was synthesized according to the procedure described in Scheme 1.1 via 6-[2-(dimethylamino)ethoxy]pyridine-3-carbaldehyde (EV-AX2012-001) synthesized according to Scheme 3.

Scheme 3

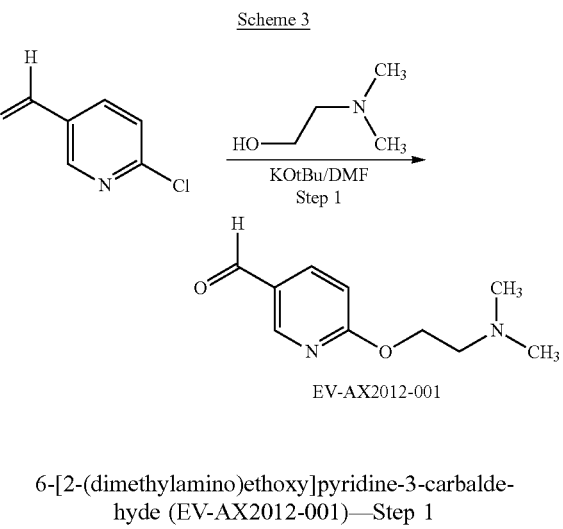

EV-AX2012-001

6-[2-(dimethylamino)ethoxy]pyridine-3-carbaldehyde (EV-AX2012-001)—Step 1

To a stirred solution of 2-(dimethylamino)ethanol (234.54 µL, 2.33 mmol) in DMF (3 ml) was added KOtBu (285.38 mg, 2.54 mmol). The reaction was stirred at RT for 10 min and 6-chloropyridine-3-carbaldehyde (300 mg, 2.12 mmol) was added. The reaction was stirred at RT for 3 h. The solvent was removed by concentrating in vacuo and the residue was partitioned between EtOAc (20 ml) and water (20 ml). The aqueous phase was washed with EtOAc (20 ml), then the organics were combined dried over $Na_2SO_4$ and concentrated in vacuo. The crude product was purified by flash column chromatography (50-100% EtOAc in heptane then 5% MeOH in EtOAc) to afford 6-[2-(dimethylamino)ethoxy]pyridine-3-carbaldehyde (EV-AX2012-001) (347 mg, 67%) as a yellow liquid. LCMS not run.

Example 22. Synthesis of 4-phenyl-3-[(2E)-3-(4-{2-[2-(prop-2-yn-1-yloxy)ethoxy]ethoxy}phenyl)prop-2-enoyl]-1,2-dihydroquinolin-2-one, I-109

4-phenyl-3-[(2E)-3-(4-{2-[2-(prop-2-yn-1-yloxy)ethoxy]ethoxy}phenyl)prop-2-enoyl]-1,2-dihydroquinolin-2-one (I-109) (EOAI3450857) was synthesized according to the procedure described in Scheme 1.2 via 4-{2-[2-(prop-2-yn-1-yloxy)ethoxy]ethoxy}benzaldehyde (EV-AV1503-001) synthesized according to Scheme 4.

Scheme 4

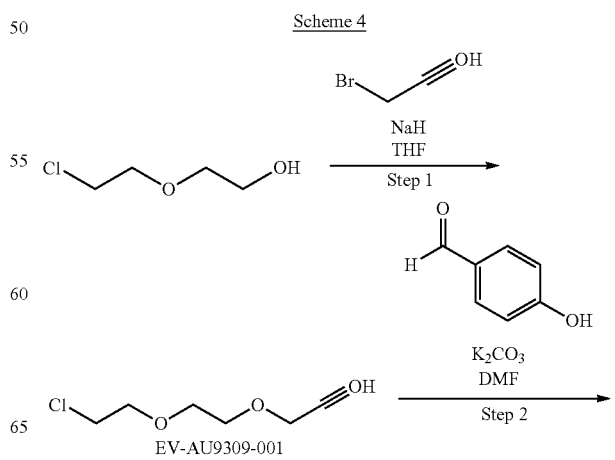

EV-AU9309-001

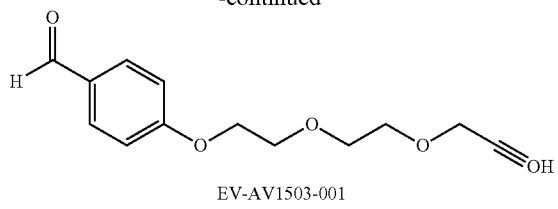

EV-AV1503-001

1-chloro-2-[2-(prop-2-yn-1-yloxy)ethoxy]ethane (EV-AU9309-001)—Step 1

Sodium hydride (60%, 642.17 mg, 16.06 mmol) was suspended in THF (25 ml) and the mixture was cooled, with stirring to −20° C. 2-(2-chloroethoxy)ethan-1-ol (847.46 µl, 8.03 mmol) was then added and the reaction was stirred at −78 C for 15 min. 3-bromoprop-1-yne (1073.03 µl, 9.63 mmol) was then added. The reaction was allowed to warm to room temperature and then heated at reflux for 3h. The reaction was allowed to cool to room temperature and the solvent was removed in vacuo. DCM (30 ml) was added to the residue followed by water (25 ml). The organic layer was collected, dried over $Na_2SO_4$ and concentrated in vacuo to afford a brown liquid. The residue was purified by flash column chromatography (DCM) to afford 1-chloro-2-[2-(prop-2-yn-1-yloxy)ethoxy]ethane (EV-AU9309-001) (630 mg, 47.3%) as a yellow liquid. LCMS not run.

4-{2-[2-(prop-2-yn-1-yloxy)ethoxy]ethoxy}benzaldehyde (EV-AV1503-001)—Step 2

$K_2CO_3$ (452.68 mg, 3.28 mmol) was added to a stirred solution of 4-hydroxybenzaldehyde (200 mg, 1.64 mmol) in DMF (1 ml) at room temperature. 1-chloro-2-[2-(prop-2-yn-1-yloxy)ethoxy]ethane (319.58 mg, 1.97 mmol) was dissolved in DMF (1 ml) and then added to the reaction mixture. The reaction mixture was heated at 100° C. and stirred for 23 h. DMF was removed in vacuo and the remaining solution was separated using EtOAc and water. The aqueous phase was washed once with EtOAc and the combined organic phases were concentrated in vacuo to give an orange oil. Purification was performed by flash column chromatography to afford 4-{2-[2-(prop-2-yn-1-yloxy)ethoxy]ethoxy}benzaldehyde (EV-AV1503-001) (312 mg, 77%) as a yellow gum. LCMS (method D): retention time 1.03 min, M/z=249 (M+1).

Example 23. Synthesis of 2-({5-[(1E)-3-(6-fluoro-2-oxo-4-phenyl-1,2-dihydroquinolin-3-yl)-3-oxoprop-1-en-1-yl]pyridin-2-yl}oxy)acetonitrile, I-5

2-({5-[(1E)-3-(6-fluoro-2-oxo-4-phenyl-1,2-dihydroquinolin-3-yl)-3-oxoprop-1-en-1-yl]pyridin-2-yl}oxy)acetonitrile (I-5) (EOAI3459416) was synthesized according to the procedure described in Scheme 1.1 via 2-[(5-formylpyridin-2-yl)oxy]acetonitrile (EV-AX2009-001) synthesized according to Scheme 5.

Scheme 5

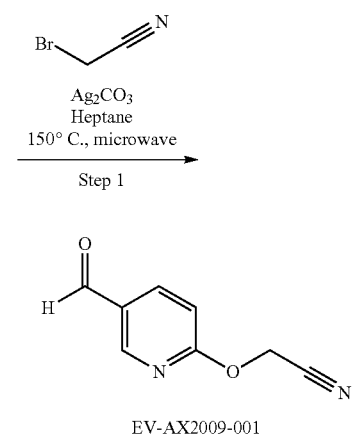

EV-AX2009-001

2-[(5-formylpyridin-2-yl)oxy]acetonitrile (EV-AX2009-001)—Step 1

To a stirred suspension of 6-hydroxypyridine-3-carbaldehyde (300 mg, 2.44 mmol) in heptane (10 ml) was added bromoacetonitrile (329.91 µL, 4.87 mmol) followed by silver carbonate (806.34 mg, 2.92 mmol). The reaction was stirred at 150° C. for 70 min in the microwave. The solvent was removed by concentrating in vacuo and this was then filtered through a small plug of Kieselguhr. The residue was washed with EtOAc (2×25 ml) and also filtered through Kieselguhr. The combined filtrate was concentrated in vacuo and purified by flash column chromatography (0-60% EtOAc in heptane) to afford 126 mg (31%) of 2-[(5-formylpyridin-2-yl)oxy]acetonitrile (EV-AX2009-001) as a colourless solid. LCMS data not recorded.

Example 24. Synthesis of 6-fluoro-3-[(2E)-3-[6-(3-hydroxypropoxy)pyridin-3-yl]prop-2-enoyl]-4-phenyl-1,2-dihydroquinolin-2-one, I-43

6-fluoro-3-[(2E)-3-[6-(3-hydroxypropoxy)pyridin-3-yl]prop-2-enoyl]-4-phenyl-1,2-dihydroquinolin-2-one (I-43) (EOAI3460909) was synthesized according to the procedure described in Scheme 1.1 via 6-(3-hydroxypropoxy)pyridine-3-carbaldehyde (EV-AX1229-001) synthesized according to Scheme 6.

Scheme 6

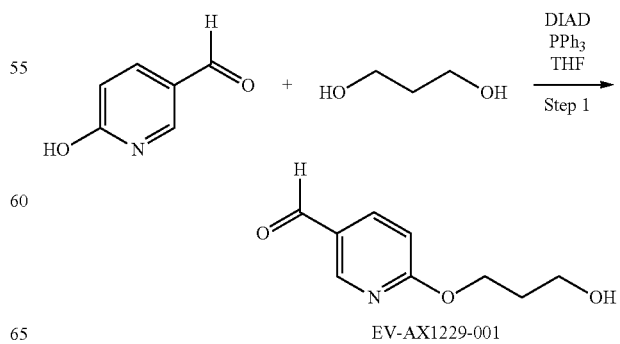

EV-AX1229-001

6-(3-hydroxypropoxy)pyridine-3-carbaldehyde (EV-AX1229-001)—Step 1

To a cold (−20° C.) solution of 6-hydroxypyridine-3-carbaldehyde (200 mg, 1.63 mmol), propane-1,3-diol (349.97 µL, 4.87 mmol) and PPh₃ (553.93 mg, 2.11 mmol) in THF (5 ml, anhydrous) was added DIAD (415.82 µL, 2.11 mmol) dropwise. The reaction was allowed to warm to RT and stirred for 3 h. The reaction was concentrated in vacuo and the resulting residue was separated between water (50 ml) and EtOAc (50 ml). The organic layer was collected and the aqueous layer was extracted using EtOAc (2×50 ml). The combined organics were dried over MgSO₄ and concentrated in vacuo. The crude material was purified by flash column chromatography (20-100% EtOAc in heptane) to afford 6-(3-hydroxypropoxy)pyridine-3-carbaldehyde (EV-AX1229-001) (62 mg, 8%) as a colourless oil. LCMS (method D): retention time 0.90 min, M/z=182 (M+1).

Example 25. Synthesis of 2-{5-[(1E)-3-(6-fluoro-2-oxo-4-phenyl-1,2-dihydroquinolin-3-yl)-3-oxoprop-1-en-1-yl]-2-oxo-1,2-dihydropyridin-1-yl}acetonitrile, I-16

2-{5-[(1E)-3-(6-fluoro-2-oxo-4-phenyl-1,2-dihydroquinolin-3-yl)-3-oxoprop-1-en-1-yl]-2-oxo-1,2-dihydropyridin-1-yl}acetonitrile (I-16) (EOAI3458842) was synthesized according to the procedure described in Scheme 1.1 via 2-[(5-formylpyridin-2-yl)oxy]acetonitrile (EV-AU9388-001) synthesized according to Scheme 7.

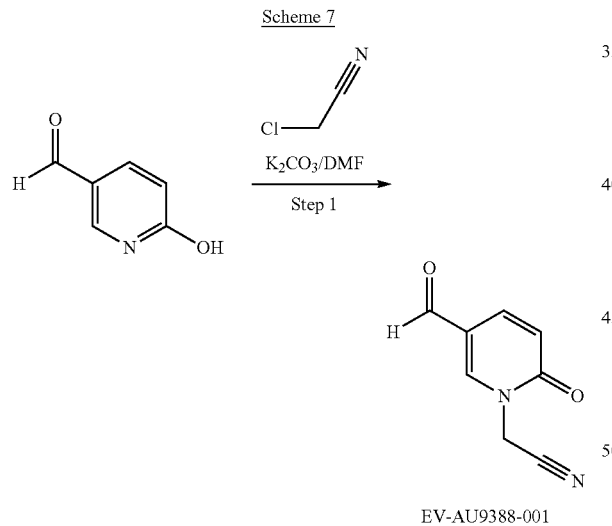

2-[(5-formylpyridin-2-yl)oxy]acetonitrile (EV-AU9388-001)—Step 1

To a stirred solution of 6-hydroxypyridine-3-carbaldehyde (250 mg, 2.03 mmol) in DMF (10 ml) under nitrogen was added K₂CO₃ (561.31 mg, 4.06 mmol) followed by chloroacetonitrile (153.95 µl, 2.44 mmol). The resulting mixture was stirred at room temperature for 1 h. The solvent was removed in vacuo and the residue was partitioned between EtOAc (30 ml) and water (25 ml). The aqueous layer was extracted further with EtOAc (2×15 ml) and the combined organics were dried over Na₂SO₄ and concentrated in vacuo. The crude was purified by flash column chromatography (0-60% EtOAc in heptane) to afford 2-(5-formyl-2-oxo-1,2-dihydropyridin-1-yl)acetonitrile (EV-AU9388-001) (164 mg, 44.8%) as a pale brown oil which solidified on standing. LCMS (method D): retention time 0.31 min, M/z=163 (M+1).

Example 26. Synthesis of 6-fluoro-3-[(2E)-3-{1-[2-(morpholin-4-yl)ethyl]-6-oxo-1,6-dihydropyridin-3-yl}prop-2-enoyl]-4-phenyl-1,2-dihydroquinolin-2-one, I-41

6-fluoro-3-[(2E)-3-{1-[2-(morpholin-4-yl)ethyl]-6-oxo-1,6-dihydropyridin-3-yl}prop-2-enoyl]-4-phenyl-1,2-dihydroquinolin-2-one (I-41) (EOAI3460911) was synthesized according to the procedure described in Scheme 1.1 via 1-[2-(morpholin-4-yl)ethyl]-6-oxo-1,6-dihydropyridine-3-carbaldehyde (EV-AX2039-001) synthesized according to Scheme 8.

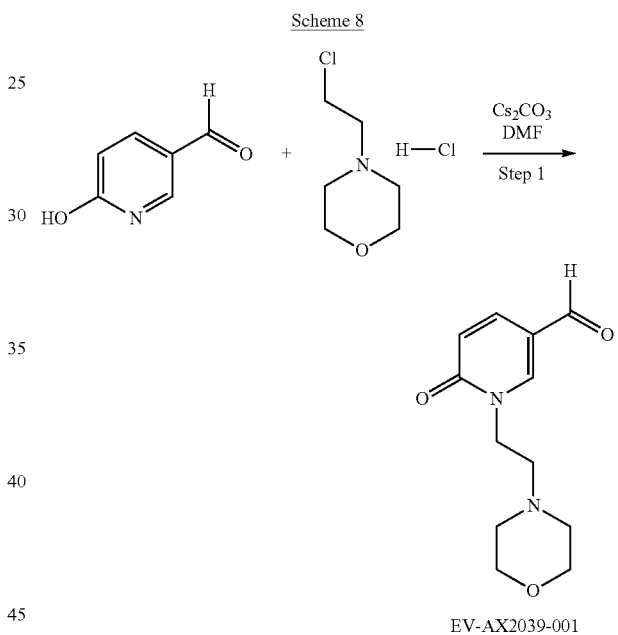

1-[2-(morpholin-4-yl)ethyl]-6-oxo-1,6-dihydropyridine-3-carbaldehyde (EV-AX2039-001)—Step 1

To a stirred solution of 6-hydroxypyridine-3-carbaldehyde (250 mg, 2.03 mmol) in DMF (5 ml) under nitrogen was added cesium carbonate (1984.94 mg, 6.09 mmol) followed by 4-(2-chloroethyl)morpholine hydrochloride (1:1) (453.45 mg, 2.44 mmol). The reaction was stirred at room temperature for 5h. The reaction was diluted with EtOAc (50 ml) and sat. NaHCO₃ (50 ml). The aqueous phase was washed with EtOAc (2×50 ml) and the combined organics were washed with water (50 ml), dried over Na₂SO₄ and concentrated in vacuo to afford a crude pale yellow solid. DCM (25 ml) was added to obtain a colourless solid in a yellow solution. The solid was filtered off and the filtrate concentrated in vacuo to afford 1-[2-(morpholin-4-yl)ethyl]-6-oxo-1,6-dihydropyridine-3-carbaldehyde (EV-AX2039-001) (438 mg, 64%) as a yellow liquid. LCMS (method D): retention time 0.22 min, M/z=237 (M+1).

Example 27. Synthesis of 6-fluoro-3-[(2E)-3-[6-oxo-1-(prop-2-yn-1-yl)-1,6-dihydropyridin-3-yl]prop-2-enoyl]-4-phenyl-1,2-dihydroquinolin-2-one, I-60

6-fluoro-3-[(2E)-3-[6-oxo-1-(prop-2-yn-1-yl)-1,6-dihydropyridin-3-yl]prop-2-enoyl]-4-phenyl-1,2-dihydroquinolin-2-one (I-60) (EOAI3460132) was synthesized according to the procedure described in Scheme 1.1 via 6-oxo-1-(prop-2-yn-1-yl)-1,6-dihydropyridine-3-carbaldehyde (EV-AX2024-001) synthesized according to Scheme 9.

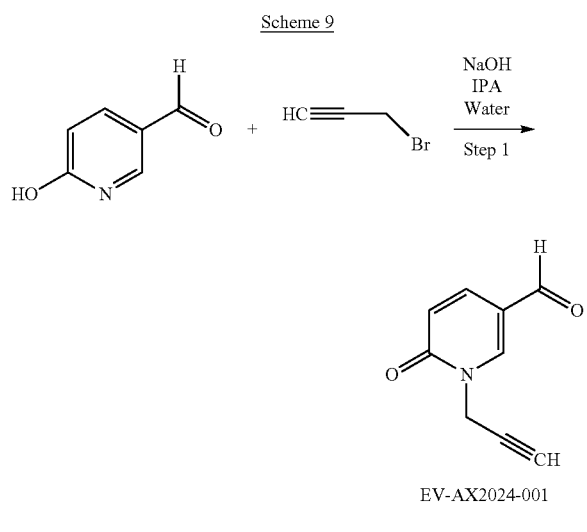

6-(prop-2-yn-1-yloxy)pyridine-3-carbaldehyde (EV-AX2024-001)—Step 1

A solution of 6-hydroxypyridine-3-carbaldehyde (CAS 106984-91-2, 300 mg, 3.66 mmol) and NaOH (116.96 mg, 2.92 mmol) in IPA (5 ml) and water (0.5 ml) was stirred at 85° C. for 30 min. 3-bromoprop-1-yne (407.15 µl, 3.66 mmol, 80% in toluene) was then added and the reaction was stirred at 85° C. for 2h. The reaction was allowed to cool to room temperature and the solvent was removed in vacuo. The residue was partitioned between EtOAc (15 ml) and water (10 ml). The aqueous layer was extracted with EtOAc (10 ml) and the combined organics were washed with water (15 ml), dried over $Na_2SO_4$ and concentrated in vacuo. The crude material was purified by flash column chromatography (0-50% EtOAc in heptane) to obtain 239 mg (60.9%) of 6-oxo-1-(prop-2-yn-1-yl)-1,6-dihydropyridine-3-carbaldehyde (EV-AX2024-001) as a pale beige solid. LCMS (method D): retention time 0.61 min, M/z=162 (M+1).

Example 28. Synthesis of 3-[(2E)-3-{4-[2-(dimethylamino)ethoxy]phenyl}prop-2-enoyl]-4-phenyl-1,2-dihydro-1,7-naphthyridin-2-one, I-31

3-[(2E)-3-{4-[2-(dimethylamino)ethoxy]phenyl}prop-2-enoyl]-4-phenyl-1,2-dihydro-1,7-naphthyridin-2-one (I-31) was synthesized according to the procedure described in Scheme 1.11 via 4-[2-(dimethylamino)ethoxy]benzaldehyde (EW3861-140) synthesized according to Scheme 10.

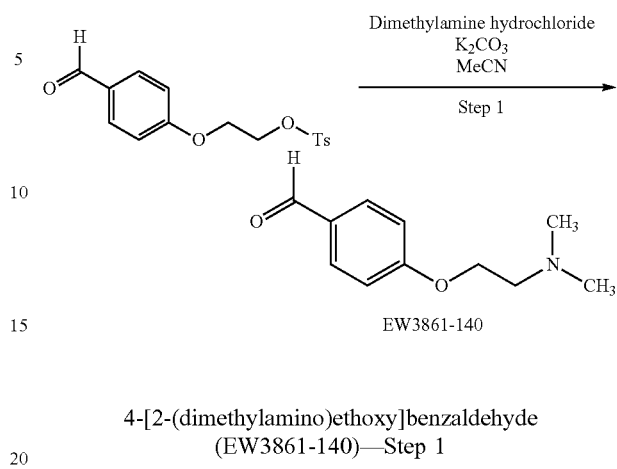

4-[2-(dimethylamino)ethoxy]benzaldehyde (EW3861-140)—Step 1

To a solution of compound 3 (750.00 mg, 2.34 mmol) in acetonitrile (8.00 ml) was added dimethylamine hydrochloride (229.07 mg, 2.81 mmol) and $K_2CO_3$ (1.62 g, 11.70 mmol, 5.00 eq). The mixture was stirred at 90° C. for 16 hr. The mixture was filtered and the filtrate was concentrated in vacuo. The residue was purified by flash column chromatography (PE:EA=1:1~DCM:MeOH=20:1) to afford 4-[2-(dimethylamino)ethoxy]benzaldehyde (EW3861-140) (260 mg, 57%) as a yellow oil. LCMS (method H): retention time 0.36 min, M/z=194 (M+1).

Example 29. Synthesis of 3-[(2E)-3-[4-(2-methoxyethoxy)phenyl]prop-2-enoyl]-4-phenyl-1,2-dihydro-1,7-naphthyridin-2-one, I-35

3-[(2E)-3-[4-(2-methoxyethoxy)phenyl]prop-2-enoyl]-4-phenyl-1,2-dihydro-1,7-naphthyridin-2-one (I-35) (EOAI-3462950) was synthesized according to the procedure described in Scheme 1.11 via 4-(2-methoxyethoxy)benzaldehyde (EW3861-115) synthesized according to Scheme 11.

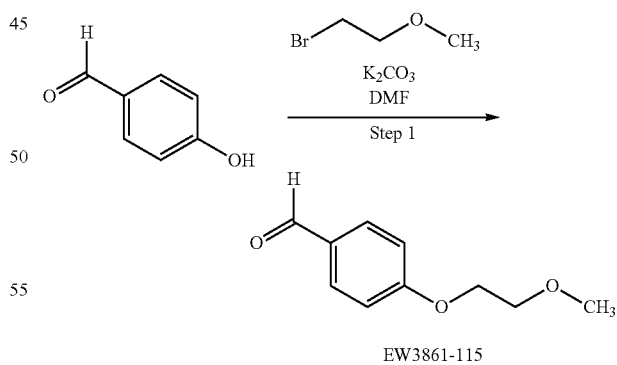

4-(2-methoxyethoxy)benzaldehyde (EW3861-115)—Step 1

To a solution of 4-hydroxybenzaldehyde (500.00 mg, 4.09 mmol) in DMF (15 ml) was added 1-bromo-2-methoxyethane (682.16 mg, 4.91 mmol, 460.92 µl) and $K_2CO_3$ (1.13 g, 8.18 mmol). The reaction mixture was stirred at 80° C. for 3 hr. The mixture was poured into water (20 ml) then extracted with EA (3×20 ml). The combined organic layers were washed with brine (3×20 ml) then dried over anhydrous Na₂SO₄ and concentrated in vacuo to afford 4-(2-methoxyethoxy)benzaldehyde (EW3861-115) (620 mg, 74%) as a yellow oil. LCMS (method I): retention time 0.62 min, M/z=181 (M+1).

Example 30. Synthesis of 4-phenyl-3-[(2E)-3-(pyridin-2-yl)but-2-enoyl]-1,2-dihydroquinolin-2-one, I-115

4-phenyl-3-[(2E)-3-(pyridin-2-yl)but-2-enoyl]-1,2-dihydroquinolin-2-one (I-115) (EOAI3449029) was synthesized according to the procedure described in Scheme 12 via 3-acetyl-4-phenyl-1,2-dihydroquinolin-2-one (EV-AR9057-002) synthesized according to Scheme 1.

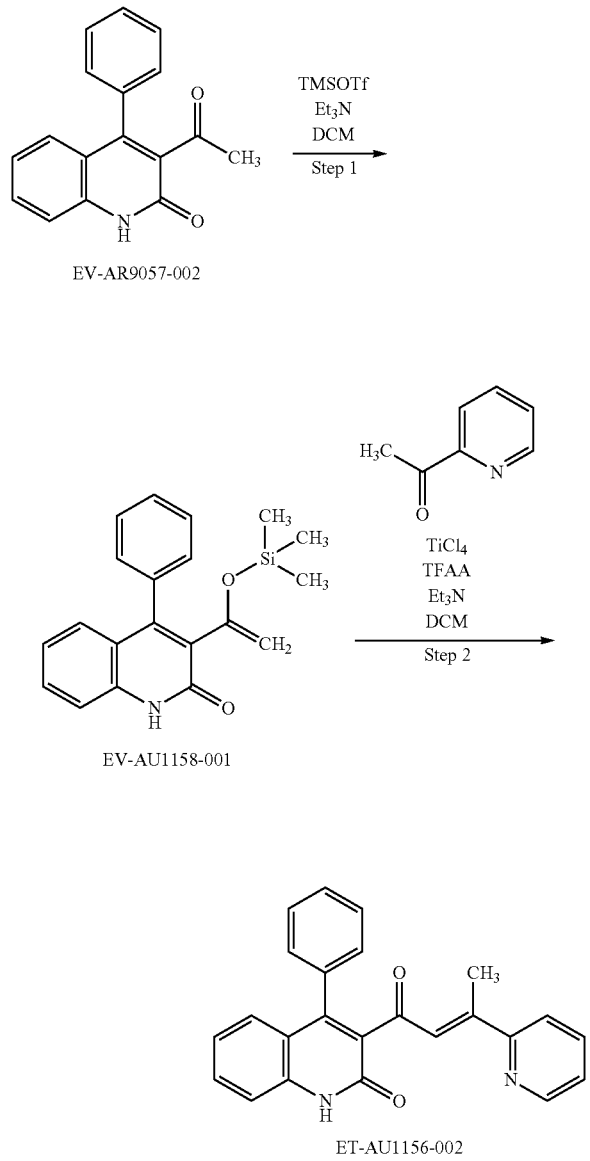

Scheme 12

4-phenyl-3-{1-[(trimethylsilyl)oxy]ethenyl}-1,2-dihydroquinolin-2-one (EV-AU1158-001)—Step 1

To a solution of 3-acetyl-4-phenyl-1,2-dihydroquinolin-2-one (EV-AR9057-002, 300 mg, 1.139 mmol) in anhydrous DCM (5 ml) at −78° C. was added Et₃N (317 µl, 2.279 mmol) and TMSOTf (227 µl, 1.253 mmol). The resulting mixture was stirred at room temperature for 18h. Further Et₃N (317 µl, 2.279 mmol) and TMSOTf (227 µl, 1.253 mmol) were added and the reaction was stirred at room temperature for 20h. The reaction was diluted with saturated NaHCO₃ (10 ml) and the aqueous layer was extracted with DCM (2×20 ml). The combined organic extracts were washed with brine, dried over Na₂SO₄ and concentrated in vacuo to afford 383 mg (80.2%) of 4-phenyl-3-{1-[(trimethylsilyl)oxy]ethenyl}-1,2-dihydroquinolin-2-one (EV-AU1158-001) as an orange oil. LCMS data not recorded.

4-phenyl-3-[(2E)-3-(pyridin-2-yl)but-2-enoyl]-1,2-dihydroquinolin-2-one (I-115) (EV-AU1156-002)—Step 2

To a solution of 4-phenyl-3-{1-[(trimethylsilyl)oxy]ethenyl}-1,2-dihydroquinolin-2-one (EV-AU1158-001, 80%, 382 mg, 0.911 mmol) in DCM (4 ml) was added 1M TiCl₄ (2 ml, in DCM) followed by 1-(pyridin-2-yl)ethan-1-one (121 mg, 1.002 mmol) and the resulting mixture was stirred at room temperature for 1 h. After this time, TFAA (127 µl, 0.911 mmol) was added and the reaction stirred at room temperature for 1 min. Triethylamine (253 µl, 1.822 mmol) was then added and stirred at room temperature for 3h. A further portion of 1-(pyridin-2-yl)ethan-1-one (121 mg, 1.002 mmol) was added and the reaction was stirred at room temperature for 2h. A further portion of 1-(pyridin-2-yl)ethan-1-one (121 mg, 1.002 mmol) was added and the reaction was stirred at room temperature for 17h. The reaction was quenched with NH₄Cl (10 ml) and the organic layer was extracted with DCM (2×30 ml). The combined organic extracts were dried over Na₂SO₄ and concentrated in vacuo. The crude material was purified by acidic preparative HPLC to obtain 28 mg (8.1%) of 4-phenyl-3-[(2E)-3-(pyridin-2-yl)but-2-enoyl]-1,2-dihydroquinolin-2-one (I-115) (EV-AU1156-002) as an orange powder. LCMS (method A): retention time 2.22 min, M/z=367 (M+1).

Example 31. Synthesis of (2E)-2-[(E)-6-methyl-2-oxo-4-phenyl-1,2-dihydroquinoline-3-carbonyl]-3-(pyridin-3-yl)prop-2-enenitrile, I-117

(2E)-2-[(E)-6-methyl-2-oxo-4-phenyl-1,2-dihydroquinoline-3-carbonyl]-3-(pyridin-3-yl)prop-2-enenitrile (I-117) (EOAI3447739) was synthesized according to Scheme 13.

Scheme 13

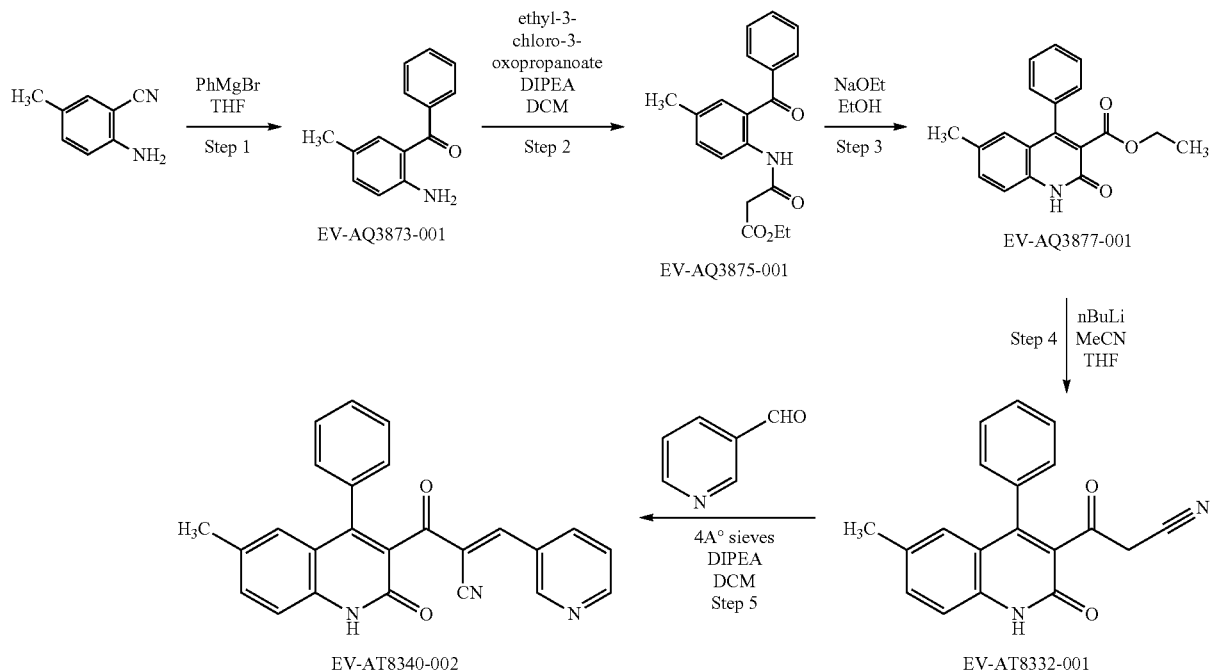

2-benzoyl-4-methylaniline (EV-AQ3873-001)—Step 1

To a solution of 3M bromo(phenyl)magnesium in Et$_2$O (22.7 ml) was added a solution of 2-amino-5-methylbenzonitrile (CAS 5925-93-9, 3 g, 22.7 mmol) in anhydrous THF (30 ml) over 0.5h. The ice bath was removed and the reaction stirred at room temperature for 17h. The solution was cooled in an ice bath and 1M aq HCl (90 ml) was added. The mixture was extracted with Et$_2$O (4×100 ml) and the organic extracts were washed with 1M aq HCl (40 ml), water (2×30 ml), saturated NaHCO$_3$ (40 ml) and brine (40 ml) then dried over MgSO$_4$ and concentrated in vacuo to obtain 5008 mg (quant) of 2-benzoyl-4-methylaniline (EV-AQ3873-001) as a brown solid. LCMS data not recorded.

Ethyl 2-[(2-benzoyl-4-methylphenyl)carbamoyl]acetate (EV-AQ3875-001)—Step 2

Ethyl 3-chloro-3-oxopropanoate (1.45 ml, 11.36 mmol) was added dropwise to a cold (0° C.) solution of 2-benzoyl-4-methylaniline (EV-AQ3873-001, 2 g, 9.47 mmol) and DIPEA (1620.6 µl, 9.47 mmol) in DCM (15 ml) under a nitrogen atmosphere. The resulting solution was stirred and allowed to warm to room temperature over 1 h. The mixture was diluted with water and extracted with DCM. The organics were dried over MgSO$_4$ to obtain 3.5 g (quant) of ethyl 2-[(2-benzoyl-4-methylphenyl)carbamoyl]acetate (EV-AQ3875-001) as a dark oil. LCMS (method D): retention time 1.20 min, M/z=326 (M+1).

Ethyl 6-methyl-2-oxo-4-phenyl-1,2-dihydroquinoline-3-carboxylate EV-AQ3877-001—Step 3

A solution of ethyl 2-[(2-benzoyl-4-methylphenyl)carbamoyl]acetate (EV-AQ3875-001, 3.08 g, 9.47 mmol) in EtOH (20 ml) was treated with ethanolate (95%, 898.04 mg, 18.93 mmol) and the resultant suspension was stirred at room temperature for 2h. The reaction was quenched with water and concentrated under vacuum. The residue was acidified to pH 6 using 1M aqueous HCl and the resulting solid was collected by filtration, washed with water followed by ether and dried under vacuum to obtain 2.21 g (76%) of ethyl 6-methyl-2-oxo-4-phenyl-1,2-dihydroquinoline-3-carboxylate (EV-AQ3877-001) as a pale yellow solid. LCMS (method D): retention time 1.16 min, M/z=308 (M+1).

3-(6-methyl-2-oxo-4-phenyl-1,2-dihydroquinolin-3-yl)-3-oxopropanenitrile (EV-AT8332-001)—Step 4

A cold (−78° C.) solution of n-butyllithium (2.5M in hexanes, 572.65 µl, 1.43 mmol) in THF (10 ml) under nitrogen was treated with acetonitrile (74.77 µl, 1.43 mmol) and the mixture was stirred at −78° C. for 1 hour before a solution of ethyl 6-methyl-2-oxo-4-phenyl-1,2-dihydroquinoline-3-carboxylate (EV-AQ3877-001, 194.17 µl, 0.65 mmol) in THF (5 ml) was added dropwise over 15 min. Once the addition was complete the mixture was stirred at −78° C. for 1h. The mixture was allowed to slowly warm to room temperature. The mixture was cooled to −78° C. and treated with n-butyllithium (2.5M, 572.65 µl, 1.43 mmol) and the cold mixture was stirred for one hour before acetonitrile (74.77 µl, 1.43 mmol) was added. The stir was continued at −78° C. for 1 h then allowed to warm to room temperature over 2h. The mixture was cooled to −78° C. and treated with n-butyllithium (2.5M, 572.65 µl, 1.43 mmol) and the cold mixture was stirred for 30 min before acetonitrile (74.77 µl, 1.43 mmol) was added. The mixture was allowed to slowly warm to room temperature overnight. The solution was quenched with water and washed with EtOAc twice. The aqueous was acidified to pH 1 with 2M aqueous HCl which caused a precipitate to form. The precipitate was collected by filtration, washed with water followed by ether and dried under vacuum for 30 min to obtain 135 mg (68.6%) of 3-(6-methyl-2-oxo-4-phenyl-1,2-dihydroquinolin-3-yl)-3-oxopropanenitrile (EV-AT8332-001) as an off white solid. LCMS (method D): retention time 1.13 min, M/z=303 (M+1).

(2E)-2-[(E)-6-methyl-2-oxo-4-phenyl-1,2-dihydroquinoline-3-carbonyl]-3-(pyridin-3-yl)prop-2-enenitrile (I-117) (EV-AT8340-002)—Step 5

A solution of 3-(6-methyl-2-oxo-4-phenyl-1,2-dihydroquinolin-3-yl)-3-oxopropanenitrile (EV-AT8332-001, 49 mg, 0.17 mmol) in DCM (1 ml) was treated with pyridine-3-carbaldehyde (1.5 ml, 16.54 mmol) followed by $Et_3N$ (2.31 µl, 0.02 mmol) and 4A molecular sieves (49.62 mg, 0.17 mmol) and the mixture was stirred at room temperature for 5 min. The solution was concentrated in vacuo and the crude was purified by acidic preparative HPLC and the fractions freeze dried to obtain 34.5 mg (53.3%) of (2E)-2-[(E)-6-methyl-2-oxo-4-phenyl-1,2-dihydroquinoline-3-carbonyl]-3-(pyridin-3-yl)prop-2-enenitrile (I-117) (EV-AT8340-002) as a yellow solid. LCMS (method A): retention time 3.04 min, M/z=392 (M+1).

Example 32. Synthesis of 2-oxo-4-phenyl-3-[(2E)-3-(pyrimidin-5-yl)prop-2-enoyl]-1,2-dihydroquinoline-6-carbonitrile, I-26

2-oxo-4-phenyl-3-[(2E)-3-(pyrimidin-5-yl)prop-2-enoyl]-1,2-dihydroquinoline-6-carbonitrile (I-26) (EOAI3-458414) was synthesized according to the procedure described in Scheme 1.2 via 3-acetyl-2-oxo-4-phenyl-1,2-dihydroquinoline-6-carbonitrile (EV-AU9376-001) synthesized according to Scheme 14.

Scheme 14

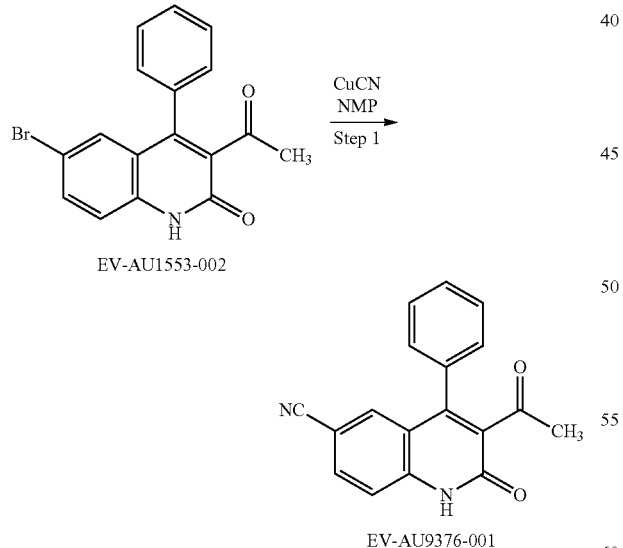

3-acetyl-2-oxo-4-phenyl-1,2-dihydroquinoline-6-carbonitrile (EV-AU9376-001)—Step 1

Copper cyanide (26.17 mg, 0.29 mmol) was added to a stirring solution of 3-acetyl-6-bromo-4-phenyl-1,2-dihydroquinolin-2-(EV-AU1553-002, 100 mg, 0.29 mmol) in NMP (1 ml). The reaction was then heated at 160° C. for 17h. The reaction was allowed to cool to room temperature and diluted with EtOAc (30 ml). A 10% solution of EDTA in 1M NaOH (aq, 30 ml) was added. The mixture was stirred at room temperature for 30 min. The layers were separated and the aqueous layer was extracted with EtOAc (2×30 ml). The combined organics were dried over $Na_2SO_4$ and concentrated in vacuo. The residue was then purified by acidic preparative HPLC to obtain 28 mg (33.2%) of 3-acetyl-2-oxo-4-phenyl-1,2-dihydroquinoline-6-carbonitrile (EV-AU9376-001) as a pale yellow solid. LCMS (method D): retention time 1.03 min, M/z=289 (M+1).

Example 33. Synthesis of 3-[(2E)-3-(5-aminopyridin-3-yl)prop-2-enoyl]-4-phenyl-1,2-dihydroquinolin-2-one, I-28 and 3-[5-(5-bromopyridin-3-yl)-1H-1,2,3-triazole-4-carbonyl]-4-phenyl-1,2-dihydroquinolin-2-one, I-27

3-[(2E)-3-(5-aminopyridin-3-yl)prop-2-enoyl]-4-phenyl-1,2-dihydroquinolin-2-one (I-28) (EOAI3455783) and 3-[5-(5-bromopyridin-3-yl)-1H-1,2,3-triazole-4-carbonyl]-4-phenyl-1,2-dihydroquinolin-2-one (I-27) (EOAI3455886) were synthesized according to Scheme 15 via 3-[(2E)-3-(5-bromopyridin-3-yl)prop-2-enoyl]-4-phenyl-1,2-dihydroquinolin-2-one (EV-AV1559-001) synthesized via the procedure described Scheme 1.1.

Scheme 15

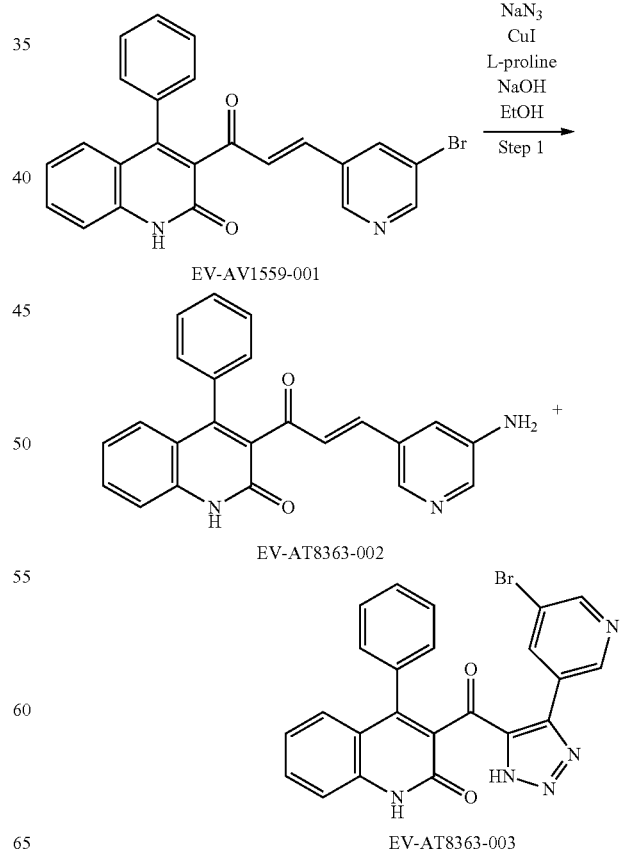

3-[(2E)-3-(5-aminopyridin-3-yl)prop-2-enoyl]-4-phenyl-1,2-dihydroquinolin-2-one (I-28) (EV-AT8363-002) and 3-[5-(5-bromopyridin-3-yl)-1H-1,2,3-triazole-4-carbonyl]-4-phenyl-1,2-dihydroquinolin-2-one (I-27) (EV-AT8363-003)—Step 1

A solution of 3-[(2E)-3-(5-bromopyridin-3-yl)prop-2-enoyl]-4-phenyl-1,2-dihydroquinolin-2-one (EV-AV1559-001, 200 mg, 0.46 mmol) in EtOH/water (4 ml, 7:3) was treated with L-proline (11.78 µl, 0.14 mmol), sodium hydroxide (2.61 µl, 0.14 mmol), copper(1+) iodide (8.83 mg, 0.05 mmol) and sodium azide (32.66 µl, 0.93 mmol). The reaction was placed under a nitrogen atmosphere and stirred at 95° C. for 6h then at room temperature for 65h. The suspension was partitioned between EtOAc and water and the mixture was filtered through Kieselguhr and the phases separated. The organics were washed with brine, dried (MgSO$_4$) and evaporated under vacuum. The crude material was purified by Basic preparative HPLC method A to afford 11 mg (6.5%) of 3-[(2E)-3-(5-aminopyridin-3-yl)prop-2-enoyl]-4-phenyl-1,2-dihydroquinolin-2-one (I-28) (EV-AT8363-002) as a pale yellow solid. LCMS (method A): retention time 1.95 min, M/z=368 (M+1) and 6 mg (2.7%) of 3-[5-(5-bromopyridin-3-yl)-1H-1,2,3-triazole-4-carbonyl]-4-phenyl-1,2-dihydroquinolin-2-one (I-27) (EV-AT8363-003) as a colourless solid. LCMS (method A): retention time 2.99 min, M/z=472 and 474 (M+1).

Example 34. Synthesis of 6-fluoro-4-phenyl-3-[(E)-2-(pyrimidin-5-yl)ethenesulfonyl]-1,2-dihydroquinolin-2-one, I-62

6-fluoro-4-phenyl-3-[(E)-2-(pyrimidin-5-yl)ethenesulfonyl]-1,2-dihydroquinolin-2-one (I-62) (EOAI3459236) was synthesized according to Scheme 16.

Scheme 16

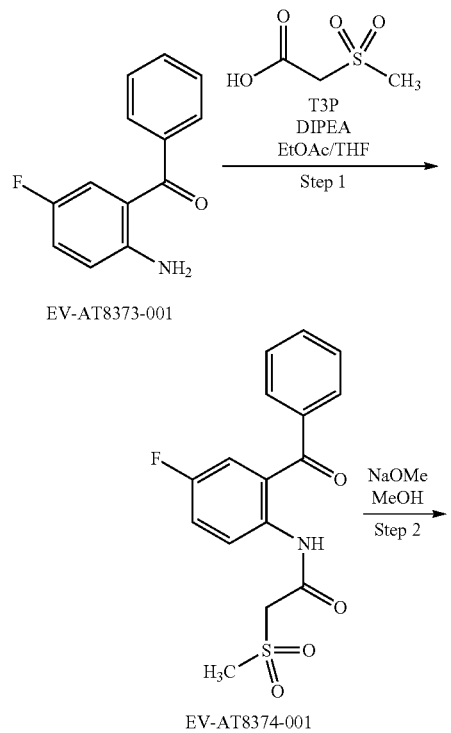

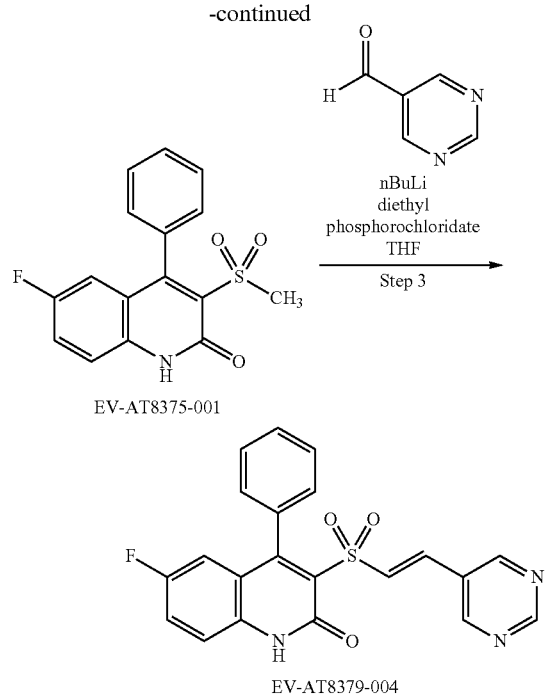

N-(2-benzoyl-4-fluorophenyl)-2-methanesulfonylacetamide (EV-AT8374-001)—Step 1

A suspension of 2-benzoyl-4-fluoroaniline (EV-AT8373-001, 500 mg, 2.32 mmol) and (methylsulfonyl)acetic acid (353.02 mg, 2.56 mmol) in THF (5 ml) was treated with T3P 50% in EtOAc (3.4 ml, 5.81 mmol) followed by DIPEA (1.01 ml, 5.81 mmol) and the resultant red solution was stirred at room temperature for 1 h. The reaction mixture was diluted with water and extracted with EtOAc (×2). The organics were washed with brine, dried (MgSO$_4$) and evaporated under vacuum to obtain 837 mg (quant) of N-(2-benzoyl-4-fluorophenyl)-2-methanesulfonylacetamide (EV-AT8374-001) as a yellow gum. LCMS (method D) retention time 1.04 min, M/z=336 (M+1).

6-fluoro-3-methanesulfonyl-4-phenyl-1,2-dihydroquinolin-2-one (EV-AT8375-001)—Step 2

A solution of N-(2-benzoyl-4-fluorophenyl)-2-methanesulfonylacetamide (EV-AT8374-001, 200 mg, 0.6 mmol) in dry methanol (4 ml) under a nitrogen atmosphere was treated with sodium methanolate (0.06 g, 1.19 mmol) and the resultant yellow solution was stirred at room temperature for 1 h. The suspension was treated with HCl (1M, 0.6 ml, 0.6 mmol), the solid was collected by filtration, washed with ether and dried under vacuum to obtain 116 mg (61.3%) of 6-fluoro-3-methanesulfonyl-4-phenyl-1,2-dihydroquinolin-2-one (EV-AT8375-001) as a white solid. LCMS (method D): retention time 1.01 min, M/z=318 (M+1).

6-fluoro-4-phenyl-3-[(E)-2-(pyrimidin-5-yl)ethenesulfonyl]-1,2-dihydroquinolin-2-one (EV-AT8379-001)—Step 3

A cold (0° C.) solution of 6-fluoro-3-methanesulfonyl-4-phenyl-1,2-dihydroquinolin-2-one (EV-AT8375-001, 200 mg, 0.63 mmol) in dry THF (5 ml) under a nitrogen atmosphere was treated dropwise with 1.6M n-butyllithium (1260.5 µl). Once the addition was complete the deep red was stirred at 0° C. for 10 min before diethyl phosphorochloridate (109 µl, 0.76 mmol) was added. The solution was stirred at 0° C. for 10 min before it was cooled to −78° C. and treated with pyrimidine-5-carbaldehyde (68.1 mg, 0.63 mmol) as a solid and the mixture was allowed to slowly warm to room temperature overnight. The solution was quenched by the addition of NH₄Cl and extracted twice with EtOAc. The organics were washed with brine, dried (MgSO₄) and evaporated under vacuum. The crude was passed through an SCX-II column (product eluted in ammonia methanol) and the residue was purified by acidic preparative HPLC. The fractions were concentrated in vacuo and the solid was triturated with EtOAc and dried in a vacuum oven to obtain 11.2 mg (4.4%) of 6-fluoro-4-phenyl-3-[(E)-2-(pyrimidin-5-yl)ethenesulfonyl]-1,2-dihydroquinolin-2-one (I-62)(EV-AT8379-001) as a pale yellow solid. LCMS (method A): retention time 2.65 min, M/z=408 (M+1).

Example 35. Synthesis of 4-(piperidin-1-yl)-3-[(2E)-3-(pyrimidin-5-yl)prop-2-enoyl]-1,2-dihydroquinolin-2-one, I-93

4-(piperidin-1-yl)-3-[(2E)-3-(pyrimidin-5-yl)prop-2-enoyl]-1,2-dihydroquinolin-2-one (I-93) (EOAI3454070) was synthesized according to the procedure described in Scheme 1.2 via 4-phenyl-3-[(2E)-3-(pyrimidin-5-yl)prop-2-enoyl]-1,2-dihydroquinolin-2-one (EV-AV9700-002) synthesized according to Scheme 17.

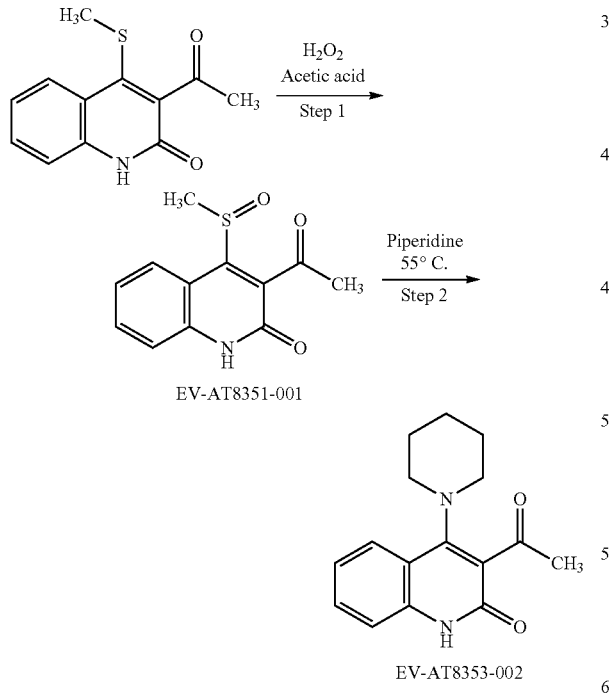

3-acetyl-4-methanesulfinyl-1,2-dihydroquinolin-2-one (EV-AT8351-001)—Step 1

A suspension of 3-acetyl-4-(methylsulfanyl)-1,2-dihydroquinolin-2-one (EV-AT8344-001 (Scheme 1.7), 500 mg, 2.14 mmol) in acetic acid (25 ml) was treated with hydrogen peroxide (35%, 656 µl, 7.5 mmol) and the resultant solution was stirred at room temperature for 21h. Ice water (40 ml) was added and the reaction was continued at room temperature for 17h. The reaction mixture was extracted with DCM (three times) and the organic extracts were washed with sat. NaHCO₃ (twice), sat. sodium thiosulfate (twice), dried over MgSO₄ and concentrated in vacuo to obtain 300 mg (56.1%) of 3-acetyl-4-methanesulfinyl-1,2-dihydroquinolin-2-one (EV-AT8351-001) as a beige solid. LCMs (method D): retention time 0.84 min, M/z=250 (M+1).

3-acetyl-4-(piperidin-1-yl)-1,2-dihydroquinolin-2-one (EV-AT8353-002)—Step 2

A solution of 3-acetyl-4-methanesulfinyl-1,2-dihydroquinolin-2-one (EV-AT8351-001, 50 mg, 0.2 mmol) in piperidine (1 ml) was stirred at 55° C. for 1 h. The solution was cooled to room temperature, diluted with water and extracted with DCM. The organic layer was dried over MgSO₄. The resulting gum was triturated with ether/heptane to obtain 38 mg (70.1%) of 3-acetyl-4-(piperidin-1-yl)-1,2-dihydroquinolin-2-one (EV-AT8353-002) as a beige solid. LCMS (method D): retention time 0.91 min, M/z=271 (M+1).

Example 36. Synthesis of 6-methyl-4-phenyl-3-[(2E)-3-(pyridin-3-yl)prop-2-enoyl]-1,2-dihydro-1,8-naphthyridin-2-one, I-47

6-methyl-4-phenyl-3-[(2E)-3-(pyridin-3-yl)prop-2-enoyl]-1,2-dihydro-1,8-naphthyridin-2-one (I-47) (EOAI3-458842) was synthesized according to the procedure described in Scheme 1.1 via 2-amino-5-methylpyridine-3-carbonitrile (EW4396-16-P1A) synthesized according to Scheme 18.

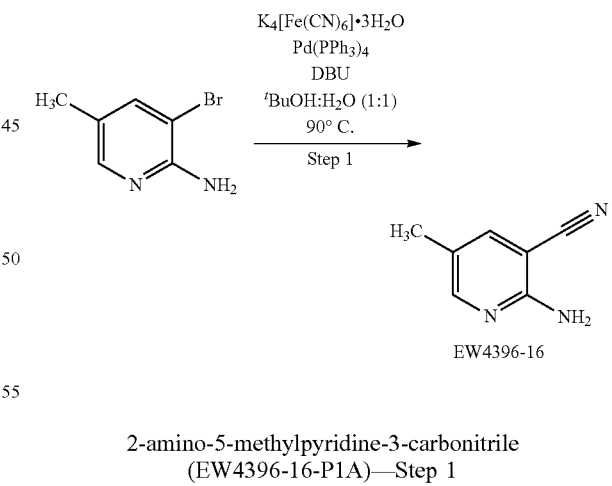

2-amino-5-methylpyridine-3-carbonitrile (EW4396-16-P1A)—Step 1

To a solution of 3-bromo-5-methyl-pyridin-2-amine (10.00 g, 53.46 mmol) in t-BuOH (40.00 ml) and H₂O (40.00 ml) was added K₄[Fe(CN)₆].3H₂O (27.10 g, 64.15 mmol), DBU (4.07 g, 26.73 mmol, 4.03 ml) and Pd(PPh₃)₄ (3.09 g, 2.67 mmol) under a N₂ atmosphere. The mixture was heated to 90° C. and stirred for 16h. DCM (15o ml) and H₂O (150 ml) was added into the mixture and filtered. The filtrate was extracted with DCM (3×50 ml). The organic phase was dried over anhydrous Na$_2$SO$_4$ and concentrated in vacuo. The residue was purified by flash column chromatography (PE:EA=10:1-3:1) to afford 2-amino-5-methylpyridine-3-carbonitrile (3.80 g, 53%) as a white solid. LCMS data not recorded.

Example 37. Synthesis of 4-phenyl-3-[(2E)-3-(pyridin-2-yl)prop-2-enoyl]-1H,2H,5H,6H,7H-cyclopenta[b]pyridin-2-one, I-149

4-phenyl-3-[(2E)-3-(pyridin-2-yl)prop-2-enoyl]-1H,2H,5H,6H,7H-cyclopenta[b]pyridin-2-one (I-149) (EOAI344-7589) was synthesized according to the procedure described in Scheme 1.2 via 3-acetyl-4-phenyl-1H,2H,5H,6H,7H-cyclopenta[b]pyridin-2-one (EV-AR9063-001) synthesized according to Scheme 19.

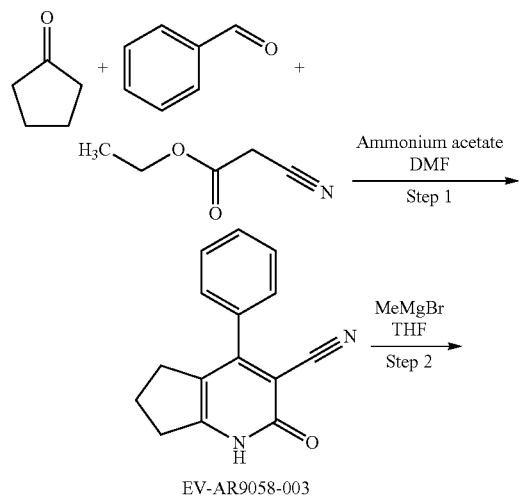

2-oxo-4-phenyl-1H,2H,5H,6H,7H-cyclopenta[b]pyridine-3-carbonitrile (EV-AR9058-003)—Step 1

To a mixture of cyclopentanone (CAS 120-92-3, 2.11 ml, 23.78 mmol), benzaldehyde (CAS 100-52-7, 4.85 ml, 47.55 mmol) and ethyl 2-cyanoacetate (CAS 105-56-6, 5.06 ml, 47.55 mmol) in DMF (10 ml) was added ammonium acetate (6183.95 µl, 95.11 mmol). The resulting mixture was heated at 80 C for 2h. The reaction mixture was allowed to cool to room temperature and diluted with water (100 ml) and DCM (200 ml). The aqueous layer was extracted with further DCM (200 ml) and the organic phases were dried over MgSO$_4$ and concentrated in vacuo. The crude was purified by flash column chromatography (50-100% EtOAc in heptane then 0-4% MeOH in EtOAc) and the resulting solid dried in a vacuum oven for 1 h to obtain 2-oxo-4-phenyl-1H,2H,5H,6H,7H-cyclopenta[b]pyridine-3-carbonitrile (EV-AR9058-003) (0.85 g, 15%) as a yellow solid. LCMS (method D): retention time 1.01 min, M/z=237 (M+1).

3-acetyl-4-phenyl-1H,2H,5H,6H,7H-cyclopenta[b]pyridin-2-one (EV-AR9063-001)—Step 2

To a solution of 2-oxo-4-phenyl-1H,2H,5H,6H,7H-cyclopenta[b]pyridine-3-carbonitrile (EV-AR9058-003, 400 mg, 1.69 mmol) in THF (10 ml) in an ice bath was added 3M bromo(methyl)magnesium in diethyl ether (1.13 ml) over 10 min. The reaction was allowed to warm to room temperature over 17h. Further 3M bromo(methyl)magnesium in diethyl ether (1.13 ml) was added dropwise and the reaction stirred at room temperature for 5h. Further 3M bromo(methyl)magnesium in diethyl ether (1.13 ml) was added dropwise and the reaction stirred at room temperature for 1 h. The reaction was cooled in an ice bath and quenched with 1M HCl (30 ml) and diluted with diethyl ether (40 ml) and DCM (50 ml). The aqueous phase was extracted with DCM (2×50 ml) and the combined organics were dried over MgSO$_4$ and concentrated in vacuo to obtain 3-acetyl-4-phenyl-1H,2H,5H,6H,7H-cyclopenta[b]pyridin-2-one (EV-AR9063-001) (270 mg, 63%) as a brown solid. LCMS (method D): retention time 1.00 min, M/z=254 (M+1).

Example 38. Synthesis of 3-[(2E)-3-(4-methoxyphenyl)prop-2-enoyl]-4-phenyl-1,2-dihydropyridin-2-one, I-148

3-[(2E)-3-(4-methoxyphenyl)prop-2-enoyl]-4-phenyl-1,2-dihydropyridin-2-one (I-148) (EOAI3442255) was synthesized according to the procedure described in Scheme 20.

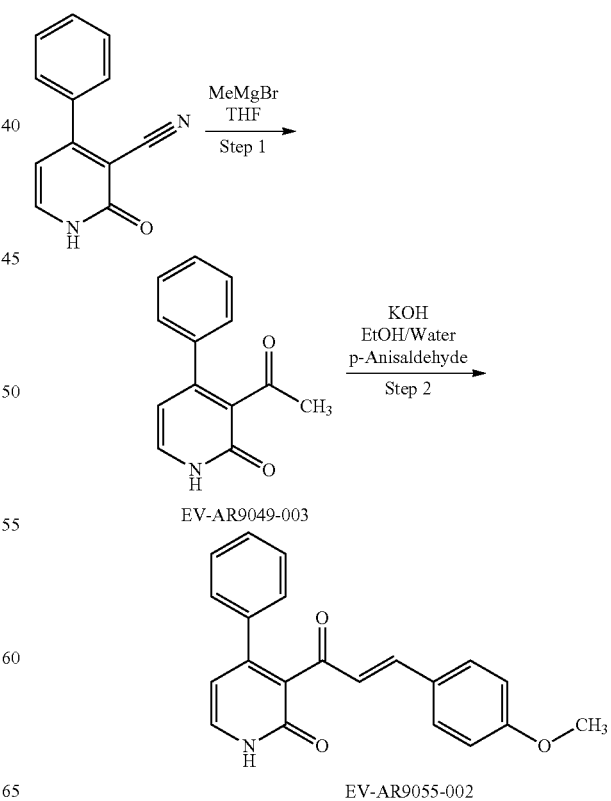

3-acetyl-4-phenyl-1,2-dihydropyridin-2-one (EV-AR9049-003)—Step 1

To a solution of 2-oxo-4-phenyl-1,2-dihydropyridine-3-carbonitrile (CAS 14045-37-5, 500 mg, 2.55 mmol) in THF (10 ml) was added 3M bromo(methyl)magnesium ion diethyl ether (1.7 ml) over 10 min. The reaction was stirred at room temperature for 17h. The reaction mixture was then quenched with 10 ml of 1M aq. HCl and left to stir at room temperature for 1 h. The reaction mixture was then extracted with diethyl ether (4×100 ml). The organics were washed with 1M HCl (100 ml), water (100 ml), sat NaHCO₃ (100 ml) and brine (100 ml) then dried over MgSO₄ and concentrated in vacuo. The resulting solid was stirred in a 1:1 MeOH: 1M HCl (30 ml) containing Acetic acid (1 ml) for 2h. The methanol was removed in vacuo and the remaining aqueous portion was extracted with DCM (2×20 ml). The combined organics were dried over MgSO₄ and concentrated in vacuo to obtain 380 mg (69.9%) of 3-acetyl-4-phenyl-1,2-dihydropyridin-2-one (EV-AR9049-002) as a brown solid. LCMS (method D): retention time 0.90 min, M/z=214 (M+1). The aqueous layer was neutralized to pH 7 with NaHCO₃ (sat) and extracted with DCM (200 ml). The organics were dried over MgSO₄ and concentrated in vacuo to obtain 3-acetyl-4-phenyl-1,2-dihydropyridin-2-one (EV-AR9049-003) (155 mg, 29%) as a brown solid. LCMS (method D): retention time 0.88 min, M/z=214 (M+1).

3-[(2E)-3-(4-methoxyphenyl)prop-2-enoyl]-4-phenyl-1,2-dihydropyridin-2-one (I-148) (EV-AR9055-002)—Step 2

To a suspension of 3-acetyl-4-phenyl-1,2-dihydropyridin-2-one (EV-AR9049-003, 100 mg, 0.47 mmol) in EtOH (4 ml) was added a solution of potassium hydroxide (85%, 123.82 mg, 1.88 mmol) in water (3 ml). The reaction was stirred at 0° C. for 30 min before the addition of 4-methoxybenzaldehyde (62.77 µl, 0.52 mmol). The resultant reaction mixture was stirred at room temperature for 20h. Further potassium hydroxide (85%, 650.06 mg, 9.85 mmol) was added and the reaction was stirred at room temperature for 20h. The reaction was quenched with Acetic acid until slightly acidic then 5M HCl (2 ml, aq) was added until a precipitate formed. The solid was filtered off then purified by Basic HPLC preparative method A. The fractions were freeze dried to obtain 3-[(2E)-3-(4-methoxyphenyl)prop-2-enoyl]-4-phenyl-1,2-dihydropyridin-2-one (I-148) (EV-AR9055-002) (43 mg, 33%) as a yellow solid. LCMS (method A): retention time 2.70 min, M/z=332 (M+1).

Example 39. Synthesis of 5-[(1E)-3-{6-fluoro-1-[2-(morpholin-4-yl)ethyl]-2-oxo-4-phenyl-1,2-dihydroquinolin-3-yl}-3-oxoprop-1-en-1-yl]pyridine-3-carbonitrile, I-58

5-[(1E)-3-{6-fluoro-1-[2-(morpholin-4-yl)ethyl]-2-oxo-4-phenyl-1,2-dihydroquinolin-3-yl}-3-oxoprop-1-en-1-yl]pyridine-3-carbonitrile (I-58) (EOAI3460299) was synthesized according to the procedure described in Scheme 1.1 via 3-acetyl-6-fluoro-1-[2-(morpholin-4-yl)ethyl]-4-phenyl-1,2-dihydroquinolin-2-one (EV-AX2030-001) synthesized according to Scheme 21.

Scheme 21

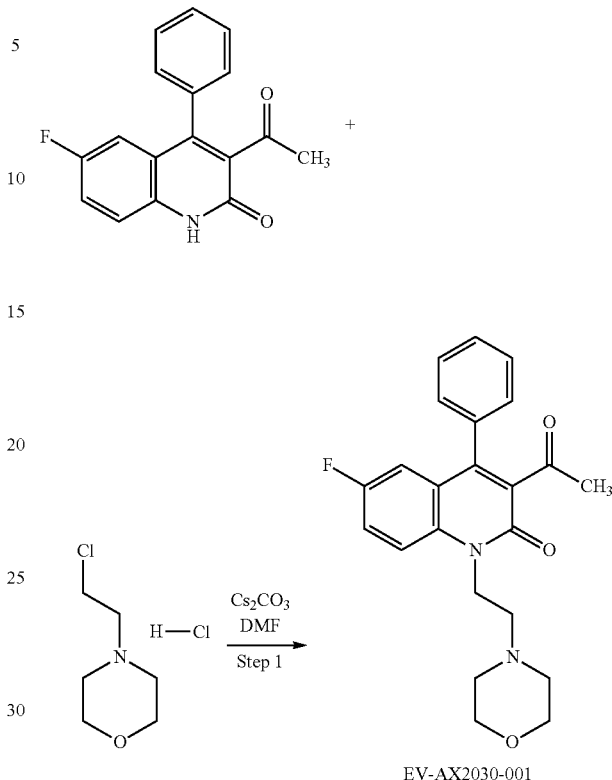

3-acetyl-6-fluoro-1-[2-(morpholin-4-yl)ethyl]-4-phenyl-1,2-dihydroquinolin-2-one (EV-AX2030-001) Step 1

To a stirred solution of 3-acetyl-6-fluoro-4-phenyl-1,2-dihydroquinolin-2-one (EV-AW8535-002, 500 mg, 1.78 mmol) in DMF (5 ml) was added cesium carbonate (2027.1 mg, 6.22 mmol) and 4-(2-chloroethyl)morpholine hydrochloride (1:1) (496.16 mg, 2.67 mmol). The resulting mixture was heated at 80° C. for 2h. Additional cesium carbonate (868.76 mg, 2.67 mmol) was added and the reaction continued for 3h. The reaction was diluted with EtOAc (30 ml) and water (30 ml). The aqueous layer was washed with EtOAc (3×25 ml) and the combined organics were washed with water (20 ml), dried over Na₂SO₄ and concentrated in vacuo. The residue was purified by Basic HPLC preparative method A to obtain 3-acetyl-6-fluoro-1-[2-(morpholin-4-yl)ethyl]-4-phenyl-1,2-dihydroquinolin-2-one (EV-AX2030-001) (338 mg, 48%) of as a colourless solid. LCMS (method D): retention time 1.03 min, M/z=395 (M+1).

Example 40. Synthesis of (2E)-N-(6-fluoro-2-oxo-4-phenyl-1,2-dihydroquinolin-3-yl)-3-phenylprop-2-enamide, I-59

(2E)-N-(6-fluoro-2-oxo-4-phenyl-1,2-dihydroquinolin-3-yl)-3-phenylprop-2-enamide (I-59) (EOAI3460298) was synthesized according to the procedure described in Scheme 22.

Scheme 22

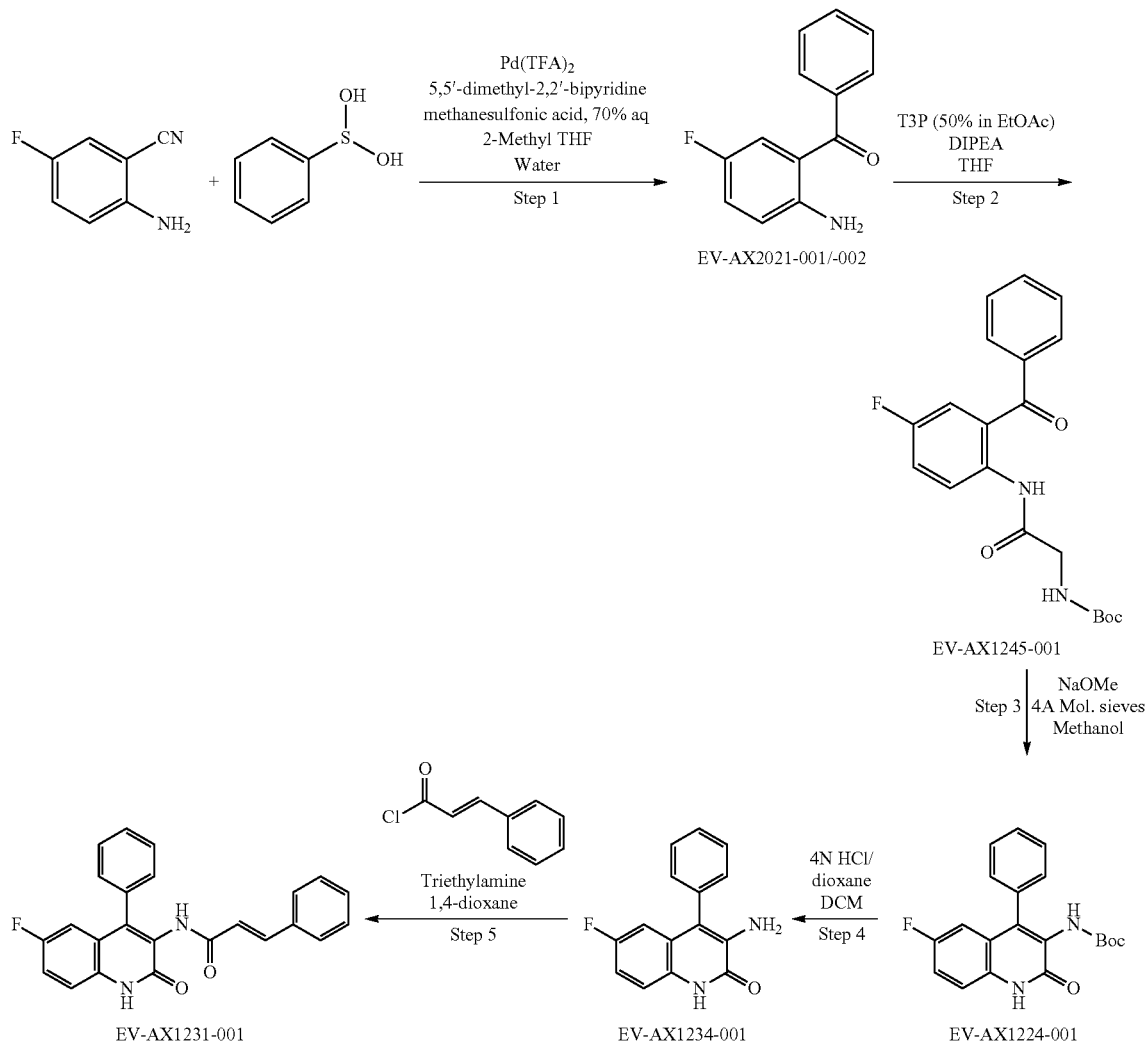

2-benzoyl-4-fluoroaniline
(EV-AX2021-001/-002)—Step 1

A stirred solution of 2-amino-5-fluorobenzonitrile (5000 mg, 36.73 mmol), phenylboronic acid (4926.41 mg, 40.4 mmol), 5,5'-dimethyl-2,2'-bipyridine (406.03 mg, 2.2 mmol) and methanesulfonic acid (38.2 ml, 367.31 mmol) in 2-methyl-THF (25 ml) and water (25 ml) was flushed with nitrogen for 15 min. Pd(TFA)$_2$ (488.44 mg, 1.47 mmol) was then added and the mixture was stirred at 80° C. for 19 h. The reaction was quenched with sat. aq. NaHCO$_3$ to pH 8 (~180 ml) and EtOAc (200 ml) was added. The aqueous layer was extracted with EtOAc (3×75 ml) and the combined organics were dried over Na$_2$SO$_4$ and concentrated in vacuo. The crude product was purified by flash column chromatography (0-40% EtOAc in heptane) to afford 2-benzoyl-4-fluoroaniline (EV-AX2021-001) (2305 mg, 29%) as a bright yellow solid. The mixed fractions were concentrated in vacuo and re-purified by flash column chromatography (0-30% EtOAc in heptane) to afford additional 2-benzoyl-4-fluoroaniline (EV-AX2021-002) (1377 mg, 17%) as a bright yellow solid. LCMS (method D): retention time 1.16 min, M/z=216 (M+1).

Tert-butyl N-{[(2-benzoyl-4-fluorophenyl)carbamoyl]methyl}carbamate (EV-AX1245-001)—Step 2

To a stirred suspension of 2-benzoyl-4-fluoroaniline (200 mg, 0.93 mmol) and N-(tert-butoxycarbonyl)glycine (179.07 mg, 1.02 mmol) in THF (2 ml, anhydrous) was added T3P 50% in EtOAc (1368.87 μL, 2.32 mmol) followed by DIPEA (404.66 μL, 2.32 mmol) to give a deep orange solution. The reaction was stirred at RT for 1 h. The reaction mixture was diluted with water (25 ml) and EtOAc (25 ml). The organic phase was collected and the aqueous phase was extracted using EtOAc (25 ml). The organics were combined, dried over MgSO$_4$, filtered and concentrated in vacuo to afford tert-butyl N-{[(2-benzoyl-4-fluorophenyl)carbamoyl]methyl}carbamate (EV-AX1245-001) (EV-AX1245-001) (450 mg, 94%) as an orange oil. LCMS (method D): retention time 1.29 min, M/z=395 (M+23).

Tert-butyl N-(6-fluoro-2-oxo-4-phenyl-1,2-dihydroquinolin-3-yl)carbamate (EV-AX1224-001)—Step 3

To a stirred solution of tert-butyl N-{[(2-benzoyl-4-fluorophenyl)carbamoyl]methyl}carbamate (81%, 2930 mg, 6.37 mmol) and 4A molecular sieves in MeOH (25 ml, anhydrous) was added 0.5 M sodium methoxide in MeOH (38.2 ml). The reaction was stirred at RT for 19 h. The reaction was treated with ammonium chloride, at which point a white precipitate formed. The solid was collected by filtration then was dissolved in 20% MeOH in DCM (100 ml). Some of the solid did not dissolve in 20% MeOH in DCM and this was discarded as it was not product. The filtrate was concentrated in vacuo to afford tert-butyl N-(6-fluoro-2-oxo-4-phenyl-1,2-dihydroquinolin-3-yl)carbamate (EV-AX1224-001) (2110 mg, 88%) of as a yellow solid. LCMS (method D): retention time 1.14 min, M/z=377 (M+23).

3-amino-6-fluoro-4-phenyl-1,2-dihydroquinolin-2-one (EV-AX1234-001)—Step 4

To a stirred solution of tert-butyl N-(6-fluoro-2-oxo-4-phenyl-1,2-dihydroquinolin-3-yl)carbamate (430 mg, 1.21 mmol) in DCM (8 ml) was added 4M HCl in dioxane (6067.02 µL). The reaction was stirred at RT for 16 h. The reaction mixture was concentrated in vacuo then the residue was separated between 10% MeOH in DCM (25 ml) and saturated NaHCO₃ (25 ml). The organic phase was collected and the aqueous phase was extracted using 10% MeOH in DCM (25 ml). The combined organics were dried over MgSO₄, filtered and concentrated in vacuo to afford 3-amino-6-fluoro-4-phenyl-1,2-dihydroquinolin-2-one (EV-AX1234-001) (282 mg, 87%) as a yellow solid. LCMS (method D): retention time 1.08 min, M/z=255 (M+1).

(2E)-N-(6-fluoro-2-oxo-4-phenyl-1,2-dihydroquinolin-3-yl)-3-phenylprop-2-enamide (I-59) (EV-AX1231-001)—Step 5

To a stirred solution of 3-amino-6-fluoro-4-phenyl-1,2-dihydroquinolin-2-one (95%, 90 mg, 0.34 mmol) in dioxane (2 ml) was added triethylamine (50.44 µL, 0.37 mmol) followed by (2E)-3-phenylprop-2-enoyl chloride (53.03 µL, 0.37 mmol) in dioxane (1 ml). The reaction mixture was then heated to 40° C. and stirred for 1 h. The reaction mixture was concentrated in vacuo, then the resulting residue was dissolved in water (25 ml) and 10% MeOH in DCM (25 ml). The organic phase was collected and the aqueous phase was extracted using 10% MeOH in DCM (25 ml). The combined organics were dried over MgSO₄, filtered and concentrated in vacuo. The crude product was purified using acidic preparative HPLC and lyophilized to afford (2E)-N-(6-fluoro-2-oxo-4-phenyl-1,2-dihydroquinolin-3-yl)-3-phenylprop-2-enamide (I-59) (EV-AX1231-001) (32.2 mg, 25%) as a white powder. LCMS (method A): retention time 3.11 min, M/z=385 (M+1).

Example 41. Synthesis of Methyl (2E)-4-[(6-fluoro-2-oxo-4-phenyl-1,2-dihydroquinolin-3-yl)formamido]but-2-enoate, 1-38

Methyl (2E)-4-[(6-fluoro-2-oxo-4-phenyl-1,2-dihydroquinolin-3-yl)formamido]but-2-enoate (I-38) (EOAI34-61957) was synthesized according to the procedure described in Scheme 23.

Scheme 23

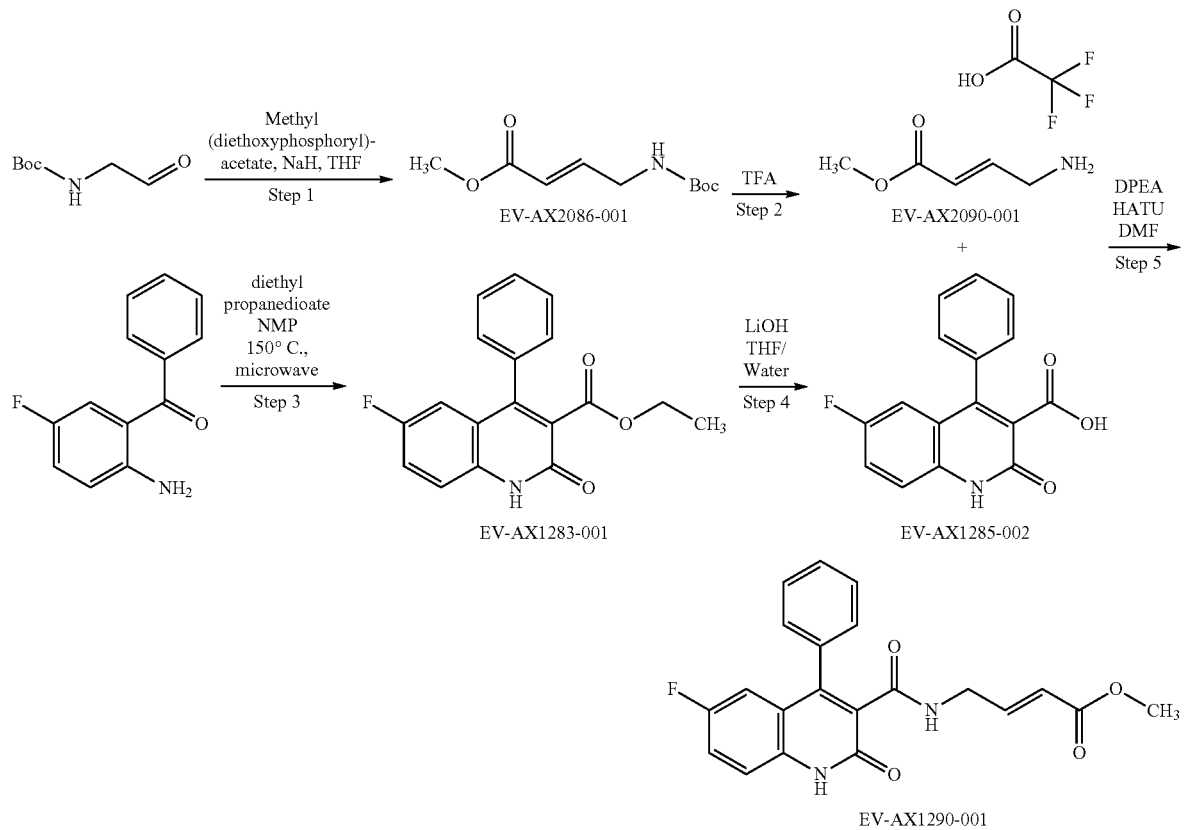

Methyl (2E)-4-{[(tert-butoxy)carbonyl]amino}but-2-enoate (EV-AX2086-001)—Step 1

Sodium hydride (60%, 238.7 mg, 5.97 mmol) in THF (30 ml) was cooled to 0° C. and a solution of methyl (diethoxyphosphoryl)acetate (1254.26 mg, 5.97 mmol) in THF (10 ml) was added dropwise. The reaction was stirred at 0° C. for 10 min and a solution of tert-butyl (2-oxoethyl)carbamate (95%, 1000 mg, 5.97 mmol) in THF (10 ml) was added. The ice bath was removed and the reaction was stirred at room temperature for 1.5h. The reaction was concentrated in vacuo and the residue was partitioned between EtOAc (50 ml) and water (50 ml). The aqueous layer was washed with EtOAc (30 ml) and the combined organics were dried over Na$_2$SO$_4$ and concentrated in vacuo. The residue was purified by flash column chromatography (10-50% EtOAc in heptane) to afford methyl (2E)-4-{[(tert-butoxy)carbonyl]amino}but-2-enoate (EV-AX2086-001) (711 mg, 53%) as a yellow oil. LCMS not run.

Trifluoroacetic Acid Methyl (2E)-4-aminobut-2-enoate (EV-AX2090-001)—Step 2

TFA (4 ml) was added to methyl (2E)-4-{[(tert-butoxy)carbonyl]amino}but-2-enoate (95%, 700 mg, 3.09 mmol) and the resulting mixture was stirred at RT for 1 h. The solvent was removed in vacuo and the residue was azeotroped with toluene (2×10 ml). The solid residue was dried on a high vac line for 2h then dissolved in MeOH (0.5 ml) and added to ice cold diethyl ether (10 ml). The resulting solid was filtered off and dried in a vac oven at 40° C. for 2h to afford trifluoroacetic acid methyl (2E)-4-aminobut-2-enoate (EV-AX2090-001) (657 mg, 92%) as a tan solid. LCMS not run.

Ethyl 6-fluoro-2-oxo-4-phenyl-1,2-dihydroquinoline-3-carboxylate (EV-AX1283-001)—Step 3

A mixture of 2-benzoyl-4-fluoroaniline (450 mg, 2.09 mmol) and diethyl propanedioate (634.86 µl, 4.18 mmol) in NMP (3 ml) were stirred in a microwave at 150° C. for 1 h. Additional diethyl propanedioate (634.86 µl, 4.18 mmol) was added and the reaction was stirred in a microwave at 150° C. for 1 h. Additional DBU (46.81 µl, 0.31 mmol) was added and the reaction was stirred in a microwave at 150° C. for 3 h. The mixture was diluted with water and the product precipitated out. The residue was filtered through a sinter, washed using diethyl ether and dried using a vacuum oven to afford ethyl 6-fluoro-2-oxo-4-phenyl-1,2-dihydroquinoline-3-carboxylate (EV-AX1283-001) (200 mg, 29%) as an off-white solid. LCMS (method D): retention time 1.12 min, M/z=312 (M+1).

6-fluoro-2-oxo-4-phenyl-1,2-dihydroquinoline-3-carboxylic acid (EV-AX1285-002)—Step 4

To a solution of ethyl 6-fluoro-2-oxo-4-phenyl-1,2-dihydroquinoline-3-carboxylate (95%, 210 mg, 0.64 mmol) in THF (5 ml) was added LiOH (76.73 mg, 3.2 mmol) in water (1 ml). The reaction was stirred at room temperature for 72 h. The reaction was heated to 50° C. and stirred for 3.5 h. Additional LiOH (38.37 mg, 1.6 mmol) was added and the reaction was stirred at 50° C. for 2 h. The reaction was retreated with further LiOH (76.73 mg, 3.2 mmol) and stirred at 50° C. for 1 h. The solvent was removed by concentrating in vacuo and the residue was dried using a high vacuum line to afford 814 mg (98.7%) of lithium(1+) ion 6-fluoro-2-oxo-4-phenyl-1,2-dihydroquinoline-3-carboxylate as a white solid (EV-AX1285-001). The product was required as the free acid hence the residue was suspended in water and acidified to pH 1. The precipitate was then collected by filtration and washed with Et$_2$O to afford 6-fluoro-2-oxo-4-phenyl-1,2-dihydroquinoline-3-carboxylic acid (EV-AX1285-002) (127 mg, 67%) as a white powder. LCMS (method D): retention time 1.04 min, M/z=284 (M+1).

(2E)-4-[(6-fluoro-2-oxo-4-phenyl-1,2-dihydroquinolin-3-yl)formamido]but-2-enoate (I-38) (EV-AX1290-001)—Step 5

To a solution of trifluoroacetic acid methyl (2E)-4-aminobut-2-enoate (95%, 85.16 mg, 0.35 mmol) in DMF (1 ml) was added 6-fluoro-2-oxo-4-phenyl-1,2-dihydroquinoline-3-carboxylic acid (100 mg, 0.35 mmol) and DIPEA (181.3 µl, 1.06 mmol) followed by HATU (147.66 mg, 0.39 mmol). The reaction was stirred at room temperature for 15 min. The reaction mixture was combined with that of a trial reaction (EV-AX1289), concentrated in vacuo, purified using acidic preparative HPLC and lyophilized to afford methyl (2E)-4-[(6-fluoro-2-oxo-4-phenyl-1,2-dihydroquinolin-3-yl)formamido]but-2-enoate (I-38)(EV-AX1290-001) (77.8 mg, 48%) as a white powder. LCMS (method A): retention time 2.47 min, M/z=381 (M+1).

Example 42. Synthesis of Methyl (2E)-4-(3-amino-6-fluoro-2-oxo-4-phenyl-1,2-dihydroquinolin-1-yl)but-2-enoate, I-39

Methyl (2E)-4-(3-amino-6-fluoro-2-oxo-4-phenyl-1,2-dihydroquinolin-1-yl)but-2-enoate (I-39) (EOAI3461695) was synthesized according to the procedure described in Scheme 24 via 3-amino-6-fluoro-4-phenyl-1,2-dihydroquinolin-2-one (EV-AX 1234-001) synthesized as described in Scheme 22.

Scheme 24

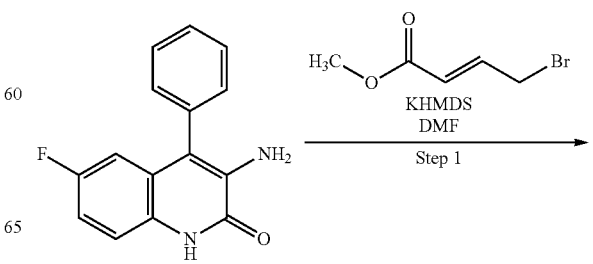

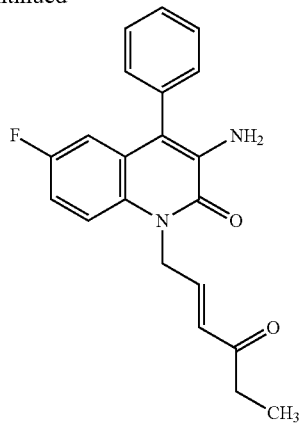

EV-AX1282-001

Methyl (2E)-4-(3-amino-6-fluoro-2-oxo-4-phenyl-1,2-dihydroquinolin-1-yl)but-2-enoate (EV-AX1282-001)—Step 1

To a solution of 3-amino-6-fluoro-4-phenyl-1,2-dihydroquinolin-2-one (93%, 50 mg, 0.18 mmol) in DMF (0.5 ml) was added 1M KHMDS in THF (201.17 μl). The mixture was stirred at RT for 30 min. Methyl (2E)-4-bromobut-2-enoate (42.96 μl, 0.37 mmol) was then added and the reaction was stirred at RT for 1 h. The reaction mixture was concentrated in vacuo, purified using acidic preparative HPLC and lyophilized to give methyl (2E)-4-(3-amino-6-fluoro-2-oxo-4-phenyl-1,2-dihydroquinolin-1-yl)but-2-enoate (I-39) (EV-AX1282-001) (10.2 mg, 15.4%) as a yellow powder. LCMS (method A): retention time 3.51 min, M/z=353 (M+1).

Table 3, below, shows the Liquid Chromatography-Mass Spectrometry (LCMS) data for selected compounds of this invention utilizing the LCMS methods described above. The compound numbers correspond to the compound numbers in Tables 1 and 2.

TABLE 3

Liquid Chromatography-Mass Spectrometry (LCMS) Data

| # | Mol Wt | LCMS $T_{retention}$ | LCMS M/z (+) | LCMS Method | Salt | Salt Stoichiometry |
|---|---|---|---|---|---|---|
| I-1 | 442.48 | 3.80 min | 443.2 | E | | |
| I-2 | 442.48 | 3.15 min | 443.2 | E | | |
| I-3 | 386.38 | 2.40 min | 386.38 | A | | |
| I-4 | 457.50 | 2.10 min | 458.2 | A | Formic acid | 0.5 |
| I-5 | 425.41 | 3.26 min | 426.1 | A | | |
| I-6 | 371.36 | 2.78 min | 372.1 | A | | |
| I-7 | 395.39 | 3.17 min | 396.1 | A | | |
| I-8 | 395.39 | 3.21 min | 396.1 | E | | |
| I-9 | 400.40 | 3.27 min | 401.1 | A | | |
| I-10 | 371.36 | 2.63 min | 372.1 | A | | |
| I-11 | 443.47 | 2.94 min | 444.1 | A | | |
| I-12 | 477.51 | 2.80 min | 478.1 | A | | |
| I-13 | 371.36 | 2.59 min | 372.1 | A | | |
| I-14 | 404.82 | 3.30 min | 405.1 | A | | |
| I-15 | 400.40 | 2.08 min | 401.1 | A | | |
| I-16 | 425.41 | 2.69 min | 426.1 | A | | |
| I-17 | 424.43 | 2.92 min | 425.1 | A | | |
| I-18 | 484.52 | 2.31 min | 485.1 | A | | |
| I-19 | 484.52 | 2.00 min | 485.1 | A | | |
| I-20 | 370.38 | 2.46 min | 371.1 | A | | |
| I-21 | 371.36 | 2.57 min | 372.1 | A | | |

TABLE 3-continued

Liquid Chromatography-Mass Spectrometry (LCMS) Data

| # | Mol Wt | LCMS $T_{retention}$ | LCMS M/z (+) | LCMS Method | Salt | Salt Stoichiometry |
|---|---|---|---|---|---|---|
| I-22 | 423.44 | 2.82 min | 424.2 | A | | |
| I-23 | 444.54 | 3.25 min | 445.2 | A | | |
| I-24 | 499.53 | 2.11 min | 500.2 | A | | |
| I-25 | 430.43 | 2.76 min | 431.1 | A | | |
| I-26 | 378.38 | 2.46 min | 379.1 | A | | |
| I-27 | 472.29 | 2.99 min | 471.9 | A | | |
| I-28 | 367.40 | 1.95 min | 368.1 | A | | |
| I-29 | 333.36 | 3.12 min | 334.1 | A | | |
| I-30 | 494.60 | 2.21 min | 495.2 | G | | |
| I-31 | 439.52 | 1.92 min | 440.2 | G | | |
| I-32 | 377.40 | 2.74 min | 378.1 | G | | |
| I-33 | 498.55 | 2.18 min | 499.2 | G | HCl | 1 |
| I-34 | 454.50 | 2.60 min | 455.1 | G | HCl | 1 |
| I-35 | 426.46 | 2.96 min | 427.1 | G | | |
| I-36 | 412.44 | 2.74 min | 413.1 | G | | |
| I-37 | 429.44 | 2.56 min | 430.1 | G | | |
| I-38 | 372.35 | 2.25 min | 373.1 | G | | |
| I-40 | 322.33 | 2.52 min | 323.1 | A | | |
| I-41 | 499.53 | 1.96 min | 500.1 | A | | |
| I-42 | 385.39 | 2.08 min | 386.1 | A | | |
| I-43 | 444.45 | 2.88 min | 445.1 | A | | |
| I-44 | 372.35 | 2.25 min | 373.1 | G | | |
| I-45 | 371.36 | 2.40 min | 372.1 | G | | |
| I-46 | 389.35 | 2.79 min | 390.1 | G | | |
| I-47 | 367.40 | 2.43 min | 368.1 | G | | |
| I-48 | 370.38 | 2.65 min | 371.1 | G | | |
| I-49 | 370.38 | 2.52 min | 371.1 | G | | |
| I-50 | 371.36 | 2.98 min | 372.1 | G | | |
| I-51 | 388.37 | 2.76 min | 389.1 | G | | |
| I-52 | 388.37 | 2.59 min | 389.1 | G | | |
| I-53 | 371.36 | 3.24 min | 372 | G | | |
| I-54 | 368.39 | 2.30 min | 369.1 | G | | |
| I-55 | 385.39 | 2.82 min | 386.1 | G | | |
| I-56 | 481.51 | 3.10 min | 482.2 | A | | |
| I-57 | 481.54 | 1.72 min | 482.2 | A | Formic acid | 0.5 |
| I-58 | 508.54 | 3.43 min | 509.2 | E | | |
| I-59 | 384.40 | 3.11 min | 385.1 | A | | |
| I-60 | 424.42 | 2.79 min | 425 | A | | |
| I-61 | 384.40 | 2.33 min | 385.1 | A | | |
| I-62 | 407.42 | 2.65 min | 408.1 | A | | |
| I-63 | 431.28 | 3.26 min | 431.1 | A | | |
| I-64 | 432.27 | 2.99 min | 432.2/ 434.1 | A | | |
| I-65 | 388.37 | 3.08 min | 389.1 | A | | |
| I-66 | 420.38 | 3.01 min | 421.2 | A | | |
| I-67 | 404.82 | 3.33 min | 405.1 | A | | |
| I-68 | 431.28 | 2.91 min | 431.0 / 433.0 | A | | |
| I-69 | 386.83 | 3.19 min | 387.1 | A | Formic acid | 0.5 |
| I-70 | 421.37 | 3.07 min | 422.1 | A | | |
| I-71 | 397.43 | 2.53 min | 398.2 | A | | |
| I-72 | 419.47 | 3.02 min | 420.2 | A | | |
| I-73 | 371.36 | 2.56 min | 372.1 | A | | |
| I-74 | 391.42 | 3.07 min | 392.1 | A | | |
| I-75 | 323.37 | 1.93 min | 324.1 | A | | |
| I-76 | 386.83 | 2.84 min | 387.1 | A | | |
| I-77 | 407.46 | 3.39 min | 408.2 | A | | |
| I-78 | 405.45 | 4.45 min | 406.2 | B | | |
| I-79 | 381.43 | 3.06 min | 382.2 | A | | |
| I-80 | 387.82 | 2.93 min | 388.1 | A | | |
| I-81 | 411.45 | 2.99 min | 412.2 | A | | |
| I-82 | 405.45 | 2.82 min | 406.1 | A | | |
| I-83 | 393.44 | 3.07 min | 394.2 | A | | |
| I-84 | 367.40 | 2.65 min | 368.2 | A | | |
| I-85 | 406.44 | 2.82 min | 407.3 | A | | |
| I-86 | 367.40 | 3.84 min | 368.1 | C | | |
| I-87 | 354.36 | 3.19 min | 355.2 | B | | |
| I-88 | 371.36 | 2.13 min | 372.2 | A | | |
| I-89 | 383.40 | 2.55 min | 384.2 | A | | |
| I-90 | 354.36 | 1.43 min | 355.2 | A | | |
| I-91 | 367.40 | 2.79 min | 368.1 | A | | |
| I-92 | 367.40 | 2.25 min | 368.1 | A | | |
| I-93 | 360.41 | 2.09 min | 361.4 | A | | |
| I-94 | 354.36 | 2.22 min | 355.1 | A | | |
| I-95 | 354.36 | 1.53 min | 355.1 | A | | |

TABLE 3-continued

Liquid Chromatography-Mass Spectrometry (LCMS) Data

| # | Mol Wt | LCMS $T_{retention}$ | LCMS M/z (+) | LCMS Method | Salt | Salt Stoichiometry |
|---|---|---|---|---|---|---|
| I-96 | 367.40 | 3.50 min | 368.2 | B | | |
| I-97 | 387.82 | 2.36 min | 388.1 | A | | |
| I-98 | 383.40 | 2.10 min | 384.1 | A | | |
| I-99 | 370.38 | 2.92 min | 371.1 | A | | |
| I-100 | 551.63 | 3.87 min | 552.2 | A | | |
| I-101 | 507.58 | 3.89 min | 508.2 | A | | |
| I-102 | 371.36 | 2.65 min | 372.1 | A | | |
| I-103 | 391.42 | 2.57 min | 392.1 | A | | |
| I-104 | 370.38 | 2.53 min | 371.1 | A | | |
| I-105 | 367.40 | 2.83 min | 368.1 | A | | |
| I-106 | 371.36 | 2.68 min | 372.1 | A | | |
| I-107 | 370.38 | 2.57 min | 371.1 | A | | |
| I-108 | 370.38 | 2.88 min | 371.1 | A | | |
| I-109 | 493.55 | 3.45 min | 494.2 | A | | |
| I-110 | 537.60 | 3.43 min | 538.2 | A | | |
| I-111 | 395.45 | 3.67 min | 396.2 | A | | |
| I-112 | 353.37 | 2.73 min | 354.1 | A | | |
| I-113 | 329.39 | 3.43 min | 330.1 | A | | |
| I-114 | 352.39 | 2.44 min | 353.1 | A | | |
| I-115 | 366.41 | 2.22 min | 367.1 | A | | |
| I-116 | 444.50 | 2.88 min | 445.1 | A | | |
| I-117 | 391.42 | 3.04 min | 392.2 | A | | |
| I-118 | 329.39 | 3.35 min | 330.2 | A | | |
| I-119 | 366.41 | 1.84 min | 367.3 | A | | |
| I-120 | 355.39 | 1.84 min | 356.2 | A | | |
| I-121 | 353.37 | 2.71 min | 354.2 | B | | |
| I-122 | 353.37 | 3.96 min | 354.2 | A | | |
| I-123 | 368.38 | 2.68 min | 369.1 | A | | |
| I-124 | 353.37 | 3.49 min | 354.2 | B | | |
| I-125 | 366.41 | 2.24 min | 367.1 | A | | |
| I-126 | 343.42 | 3.62 min | 344.1 | A | | |
| I-127 | 357.44 | 3.86 min | 358.2 | A | | |
| I-128 | 341.36 | 1.80 min | 342.1 | A | | |
| I-129 | 352.39 | 2.78 min | 353.1 | A | | |
| I-130 | 315.37 | 4.40 min | 316.2 | B | | |
| I-131 | 390.43 | 4.79 min | 391.2 | B | | |
| I-132 | 319.35 | 2.92 min | 320.0 | A | | |
| I-133 | 289.33 | 2.93 min | 290.0 | A | | |
| I-134 | 276.29 | 2.61 min | 277.0 | A | | |
| I-135 | 366.41 | 2.61 min | 367.1 | A | | |
| I-136 | 305.33 | 2.95 min | 306.1 | C | | |
| I-137 | 409.48 | 3.83 min | 410.1 | A | | |
| I-138 | 365.42 | 3.54 min | 366.1 | A | | |
| I-139 | 381.42 | 3.34 min | 382.1 | A | | |
| I-140 | 397.43 | 3.06 min | 398.2 | A | | |
| I-141 | 391.42 | 3.72 min | 392.1 | A | | |
| I-142 | 393.44 | 3.95 min | 394.2 | A | | |
| I-143 | 381.43 | 3.84 min | 382.2 | A | | |
| I-144 | 411.45 | 3.60 min | 412.2 | A | | |
| I-145 | 366.41 | 3.90 min | 367.1 | A | | |
| I-146 | 395.45 | 4.35 min | 396.1 | A | | |
| I-147 | 336.39 | 3.23 min | 337.2 | A | | |
| I-148 | 331.36 | 2.70 min | 332.1 | A | | |
| I-149 | 342.39 | 2.45 min | 343.2 | A | | |
| I-150 | 302.33 | 1.67 min | 303.1 | A | | |
| I-151 | 255.27 | 2.25 min | 256 | A | | |

Biological Assays

Example 43. PAD4 Assays

Compounds of the present invention were assayed as inhibitors of PAD4 using the assay protocol described below.

Compounds were solubilized in 100% DMSO to achieve 100 mM final compound concentration. Compound stock solutions were stored at RT. A series of dilutions were prepared in DMSO and mixed 8 times with 20 µL mixing volume. Final assay conditions were as follows:
Reaction volume: 20 µl
Assay buffer (as aforementioned): 100 mM Tris-HCl (pH 7.6), 2 mM DTT, 1 mM CaCl₂

Final concentrations:
100 nM hPAD4 enzyme
50 µM (8-fold sub-$K_m$) substrate peptide
0.5% DMSO
Total incubation time: 65 mins at 37° C.
Stop solution: 40 µl 5% TCA in ACN
0.25 µL of compound solution was added to 10 µL of 200 nM PAD4 in assay buffer (100 mM Tris-HCl pH 7.6, 2 mM DTT). After 5 mins, 10 µL of 100 µM of substrate in buffer (100 mM Tris-HCl pH 7.6, 2 mM DTT, 2 mM CaCl2) was added and the reaction incubated for 60 mins at 37° C. The enzymatic reaction was quenched by addition of 40 µl of 5% TCA in ACN (1.7% TCA final concentration) stop solution. Arginine containing substrate and citrulline containing product (+1 Da mass shift) were subjected to solid phase extraction on Agilent RapidFire (RF) 300 system and detected on a coupled, triple quadrupole Agilent 6460 QQQ mass spectrometry (MS) device under application of multiple reaction monitoring (MRM) for quantitation.

Table 4, below, shows the activity of selected compounds of this invention in the PAD4 assays described above. The compound numbers correspond to the compound numbers in Tables 1 and 2. Compounds having an activity designated as "A" provided an $IC_{50}$ of 0.1-3 µM; compounds having an activity designated as "B" provided an $IC_{50}$ of 3-20 µM; compounds having an activity designated as "C" provided an $IC_{50}$ of 20-100 µM; and compounds having an activity designated as "D" provided an $IC_{50}$ of >100 µM. The term $pIC_{50} = -\log(IC_{50})$. Compounds having an activity designated as "E" provided a $pIC_{50}$ of 1-4; compounds having an activity designated as "F" provided a $pIC_{50}$ of 4-5; and compounds having an activity designated as "G" provided a $pIC_{50}$ of >5. "NA" stands for "not assayed."

Covalent Modification Study Using MS (Mass Spectrometry)

Example 44. PAD4 Covalent Modification Assay

Mass spectrometry was used to analyze covalent modification of protein by selected inhibitors. Recombinant human PAD4 was used at 4 mg/ml in 20 mM Tris pH7.6, 400 mM NaCl, 5 mM TCEP. Where applicable, buffer was supplemented with 5 mM CaCl₂ to determine Calcium sensitivity of modification. Inhibitors were dissolved in DMSO at final concentrations of 0.2 mM to 5 mM and incubated with protein at 27° C. for 16 hours prior to analysis. Control experiments were performed with protein and DMSO in absence of inhibitor. Samples were centrifuged for 15 seconds at 10000 rpm at room temperature immediately prior to analysis using a Waters LCT-Premier TOF mass spectrometer, using a mobile phase from 5% to 80% acetonitrile in water supplemented by 0.1% formic acid.

Inactivation Kinetics

Example 45. PAD4 Inactivation Kinetics

Covalent binding of an active compound to the target enzyme leads to time dependent loss of the enzyme activity. The rate of inactivation depends on the inhibitor concentration ([I]) and can be quantified under pseudo-first order conditions ([I]>>[hPAD4]).

Inactivation kinetics experiments were performed in 384-well polystyrene plates at 37° C. Compounds (10-200 µM) and hPAD4 (4 µM) solutions were pre-incubated in assay buffer (100 mM Tris-HCl, pH 7.6) containing 10 mM CaCl₂ and 2 mM DTT for 10 minutes to reach a temperature of 37° C. Equal volumes (10 µl) of compound and hPAD4 solutions were mixed at various time points between 0 and 70 minutes. At 70 minutes time point, the inactivation solution was diluted 10-fold in enzymatic reaction buffer (100 mM Tris-HCl, pH 7.6) containing 166.7 µM peptide substrate (H-TSTGGRQGSHH-CONH$_2$), 1.1 mM CaCl$_2$ and 2 mM DTT. After 30 minutes of incubation at 37° C. the enzymatic reaction was quenched by 3-fold dilution in 5% TCA solution in ACN. Substrate peptide arginine citrullination was determined by solid phase extraction mass spectrometry (SPE-MS). An Agilent RapidFire 300 equipped with a HILIC (H1) cartridge was used for sampling with solvents 0.1% TFA in H$_2$O/ACN (20/80) for P1 and 0.1% TFA in H$_2$O/ACN (50/50) for P2 and P3. Substrate and product peptide were detected using a coupled Agilent 6460 QQQ and multiple reaction monitoring (MRM) on transitions 562.3/969.4 and 562.8/541, respectively, in positive ion mode. DMSO content of the inactivation reaction was 1%. Cl-amidine (100 mM, final concentration during enzyme inactivation reaction) and 1% DMSO were used as positive and negative controls of the inactivation reaction, respectively.

Pseudo-first order rate constants of inactivation reaction, $k_{obs}$, were determined by fitting the time dependent loss of residual hPAD4 activity, $A_{res}$, with equation: $A_{res}(t)=e^{-kobs*t}$. A plot of the pseudo-first order rate constants versus molar concentrations of the inhibitors allowed determination of the kinetic reaction constants: $k_{inact}$—maximum rate of inactivation at infinite [I]; $K_I$—inhibitor concentration, at which rate of inactivation is equal to ½$k_{inact}$; $k_{inact}/K_I$.

Certain compounds of the present invention were assayed according to the procedures described above and were found to covalently modify PAD4.

Table 4, below, shows the activity of selected compounds of this invention in the covalent modification assay described above. The compound numbers correspond to the compound numbers in Tables 1 and 2.

TABLE 4

| | PAD4 Activity | |
|---|---|---|
| Compound # | hPAD4-RFMS: IC50 (µM) (Average) | hPAD4-RFMS: pIC50 (Average) |
| I-1 | NA | NA |
| I-2 | B | G |
| I-3 | B | G |
| I-4 | A | G |
| I-5 | A | G |
| I-6 | B | F |
| I-7 | B | G |
| I-8 | B | G |
| I-9 | A | G |
| I-10 | B | F |
| I-11 | B | F |
| I-12 | B | G |
| I-13 | B | G |
| I-14 | B | G |
| I-15 | B | G |
| I-16 | NA | NA |
| I-17 | B | G |
| I-18 | NA | NA |
| I-19 | B | F |
| I-20 | A | G |
| I-21 | B | G |
| I-22 | A | G |
| I-23 | NA | NA |
| I-24 | NA | NA |
| I-25 | NA | NA |
| I-26 | NA | NA |
| I-27 | C | F |
| I-28 | B | G |

TABLE 4-continued

| | PAD4 Activity | |
|---|---|---|
| Compound # | hPAD4-RFMS: IC50 (µM) (Average) | hPAD4-RFMS: pIC50 (Average) |
| I-29 | C | F |
| I-30 | NA | NA |
| I-31 | NA | NA |
| I-32 | NA | NA |
| I-33 | NA | NA |
| I-34 | A | G |
| I-35 | NA | NA |
| I-36 | NA | NA |
| I-37 | NA | NA |
| I-38 | NA | NA |
| I-40 | C | F |
| I-41 | B | G |
| I-42 | C | F |
| I-43 | B | G |
| I-44 | B | G |
| I-45 | B | G |
| I-46 | B | G |
| I-47 | B | G |
| I-48 | B | G |
| I-49 | A | G |
| I-50 | B | G |
| I-51 | C | F |
| I-52 | B | G |
| I-53 | A | G |
| I-54 | B | F |
| I-55 | B | G |
| I-56 | B | F |
| I-57 | C | F |
| I-58 | B | F |
| I-59 | C | F |
| I-60 | A | G |
| I-61 | A | G |
| I-62 | C | F |
| I-63 | B | G |
| I-64 | B | G |
| I-65 | B | G |
| I-66 | A | G |
| I-67 | B | G |
| I-68 | A | G |
| I-69 | B | G |
| I-70 | B | G |
| I-71 | B | F |
| I-72 | D | F |
| I-73 | B | F |
| I-74 | B | F |
| I-75 | C | F |
| I-76 | A | G |
| I-77 | C | F |
| I-78 | C | F |
| I-79 | C | F |
| I-80 | A | G |
| I-81 | C | F |
| I-82 | C | F |
| I-83 | C | F |
| I-84 | C | F |
| I-85 | C | F |
| I-86 | B | F |
| I-87 | C | F |
| I-88 | C | F |
| I-89 | C | F |
| I-90 | D | E |
| I-91 | C | F |
| I-92 | C | F |
| I-93 | C | F |
| I-94 | C | F |
| I-95 | D | E |
| I-96 | C | F |
| I-97 | C | F |
| I-98 | C | F |
| I-99 | B | G |
| I-100 | C | F |
| I-101 | C | F |
| I-102 | C | F |
| I-103 | C | F |

TABLE 4-continued

PAD4 Activity

| Compound # | hPAD4-RFMS: IC50 (μM) (Average) | hPAD4-RFMS: pIC50 (Average) |
|---|---|---|
| I-104 | B | F |
| I-105 | B | G |
| I-106 | B | G |
| I-107 | A | G |
| I-108 | D | E |
| I-109 | D | E |
| I-110 | C | F |
| I-111 | C | F |
| I-112 | C | F |
| I-113 | C | F |
| I-114 | B | F |
| I-115 | C | F |
| I-116 | B | G |
| I-117 | C | F |
| I-118 | C | F |
| I-119 | C | F |
| I-120 | B | F |
| I-121 | C | F |
| I-122 | B | F |
| I-123 | B | G |
| I-124 | D | E |
| I-125 | B | F |
| I-126 | C | F |
| I-127 | C | F |
| I-128 | C | F |
| I-129 | B | F |
| I-130 | B | F |
| I-131 | B | G |
| I-132 | C | F |
| I-133 | C | F |
| I-134 | C | F |
| I-135 | B | G |
| I-136 | C | F |
| I-137 | B | F |
| I-138 | B | G |
| I-139 | B | G |
| I-140 | C | F |
| I-141 | C | F |
| I-142 | C | F |
| I-143 | C | F |
| I-144 | C | F |
| I-145 | C | F |
| I-146 | C | F |
| I-147 | C | F |
| I-148 | C | F |
| I-149 | NA | NA |
| I-150 | C | F |
| I-151 | D | E |

TABLE 5

Covalent Modification Study: Inactivation Kinetics*

| Compound # | $k_{inact}$ (min$^{-1}$) | $K_i$ (μM) | $k_{inact}/K_i$ (min$^{-1}$M$^{-1}$) | Comments |
|---|---|---|---|---|
| I-3 | | | 5059 | |
| I-4 | | | 14148 | |
| I-5 | | | 24372 | measured at 5 μM |
| I-6 | | | 13680 | measured at 5 μM |
| I-7 | | | 18384 | measured at 5 μM |
| I-9 | | | 10150; 1453 | both measured at 5 μM |
| I-13 | | | 14184 | |
| I-61 | | | 8267 | |
| I-62 | | | 0 | inactive compound |
| I-64 | | | 11160 | measured at 5 μM |
| I-65 | | | 7477; 29424 | both measured at 5 μM |
| I-66 | | | 13344 | measured at 5 μM |
| I-67 | | | 8496 | measured at 5 μM |
| I-70 | | | 4969 | measured at 5 μM |
| I-73 | | | 2657 | measured at 5 μM |
| I-74 | | | 2587 | measured at 5 μM |
| I-76 | | | 6766 | measured at 5 μM |
| I-77 | | | 1534 | measured at 5 μM |
| I-78 | | | 200 | measured at 5 μM |
| I-79 | | | 1748 | measured at 5 μM |
| I-80 | | | 23664; 5555 | both measured at 5 μM |
| I-81 | | | 939 | measured at 5 μM |
| I-83 | | | 994 | measured at 5 μM |
| I-84 | | | 2435 | measured at 5 μM |
| I-85 | | | 1620 | measured at 5 μM |
| I-86 | | | 2508 | measured at 5 μM |
| I-87 | | | 2273 | measured at 5 μM |
| I-99 | 0.1098 | 17.56 | 6253 | |
| I-104 | 0.1028 | 20.89 | 4921 | |
| I-105 | 0.1231 | 53.39 | 2306 | |
| I-106 | 0.151 | 8.42 | 17927 | |
| I-107 | 0.6292 | 22.07 | 28509 | multi-concentration data |
| I-112 | | | 337 | only linear part of a $k_{obs}$ vs [L] curve obtained |
| I-115 | 0.2831 | 379.9 | 745 | |
| I-116 | 0.0635 | 34.65 | 1832 | |
| I-119 | 0.0674 | 25.51 | 2642 | |
| I-120 | | | 1109 | |
| I-121 | 0.1264 | 67.1 | 1884 | no saturation |
| I-122 | 0.2827; 0.3291 | 46.79; 82.69 | 6042; 3980 | |
| I-123 | | | 1367 | no saturation up to 150 μM |
| I-125 | | | 976 | no saturation up to 150 μM |
| I-128 | 0.2571 | 243 | 1058 | saturation of a $k_{obs}$ vs [L] curve reached |
| I-130 | 0.0513 | 139 | 370 | |
| I-135 | 0.345 | 35.4 | 9743 | |
| I-137 | 0.029 | 127 | 228 | |
| I-138 | 0.0666 | 30.99 | 2150 | |

*hPAD4 isoform; Ca$^{++}$ concentration = 10 mM

We claim:
1. A compound of formula I or formula II:
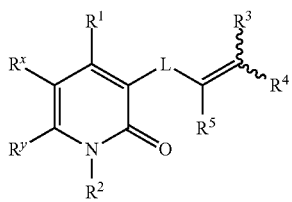
I
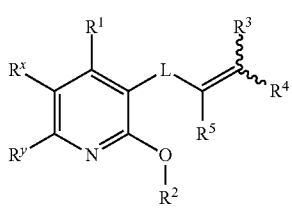
II
or a pharmaceutically acceptable salt thereof, wherein:
R$^1$ is S(CH$_3$),
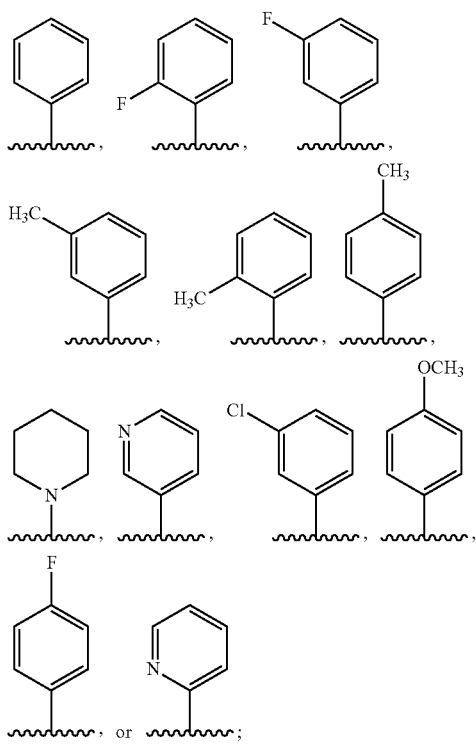
R$^2$ is hydrogen or optionally substituted C$_{1-6}$-aliphatic;
L is
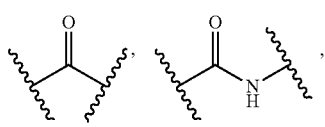
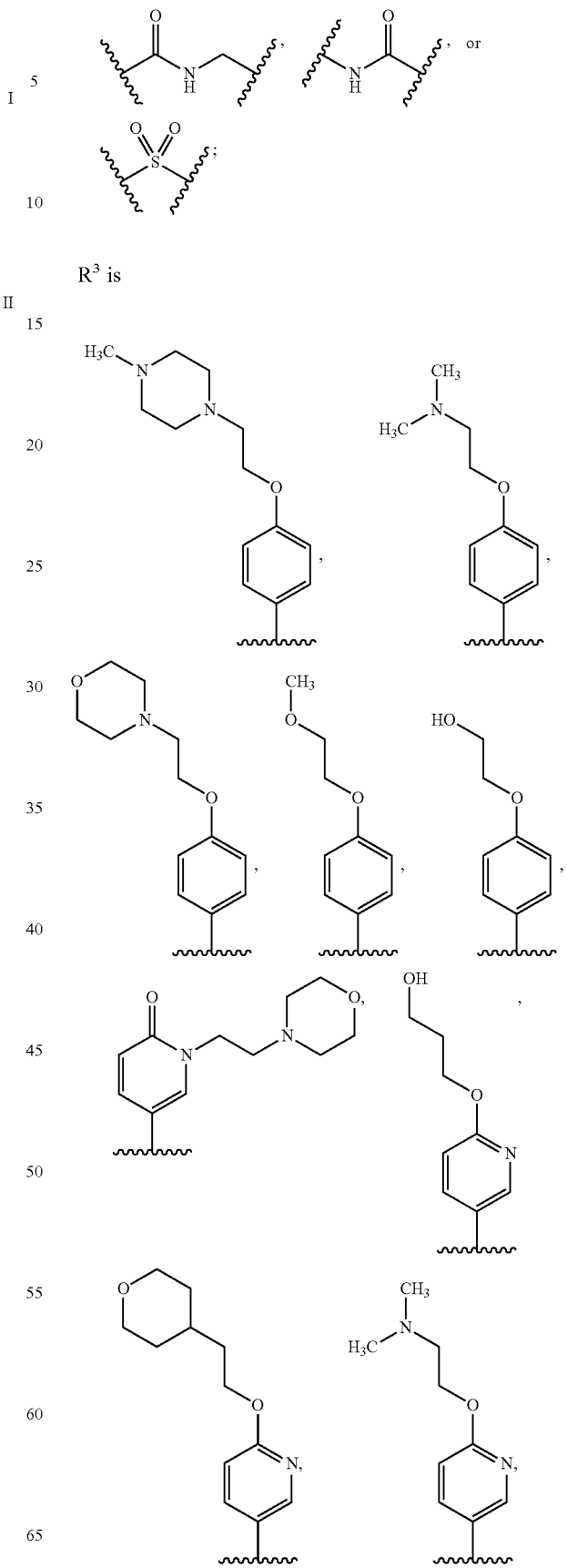
R$^3$ is

-continued

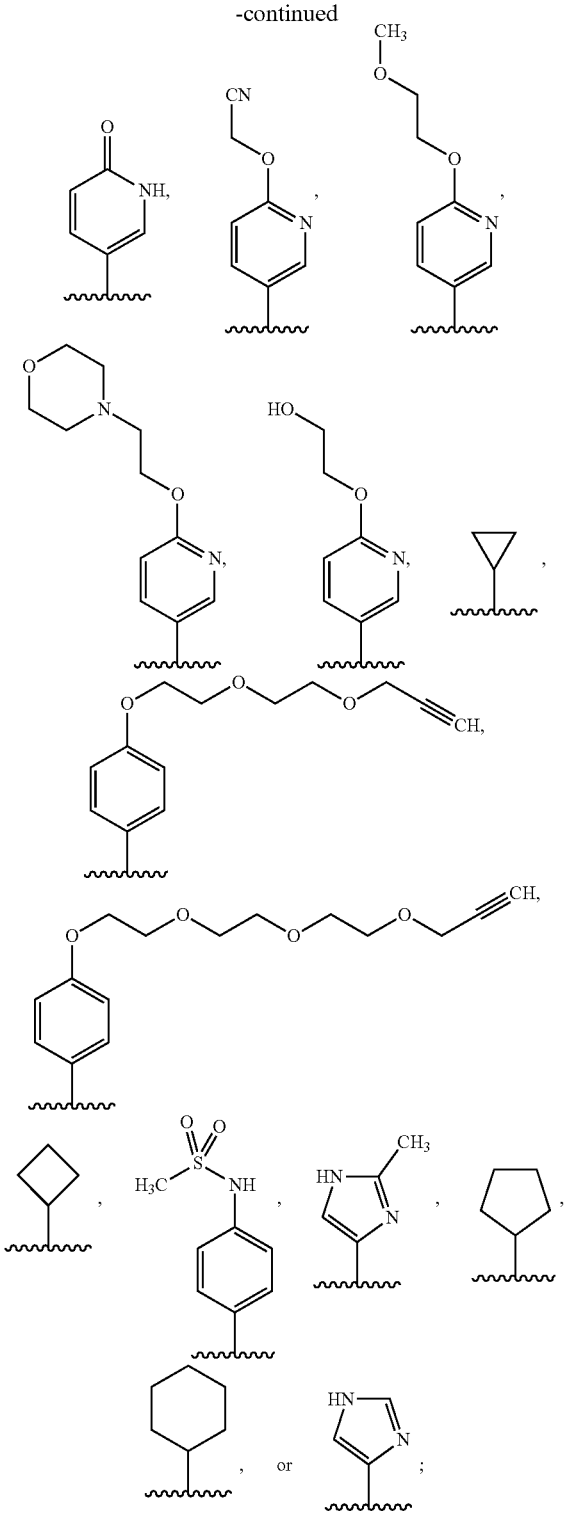

R⁴ is R or C(O)OR;
each R is independently hydrogen or C₁₋₆ aliphatic optionally substituted with 1-3 fluorine atoms;
R⁵ is hydrogen or CN;
Rˣ and Rʸ are taken together with their intervening atoms to form a optionally substituted 5-6 membered saturated, partially unsaturated, or aromatic fused ring having 1-2 heteroatoms independently selected from nitrogen, oxygen, or sulfur.

2. The compound according to claim 1, wherein said compound is selected from any one of formula I-i, II-i, or II-ii:

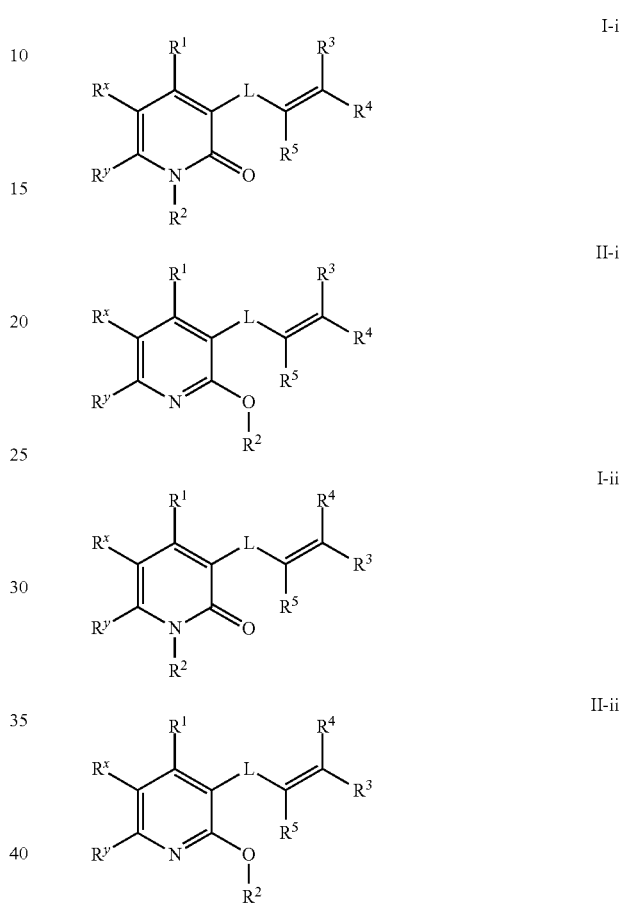

or a pharmaceutically acceptable salt thereof.

3. The compound according to claim 1, wherein R² is H, methyl, ethyl,

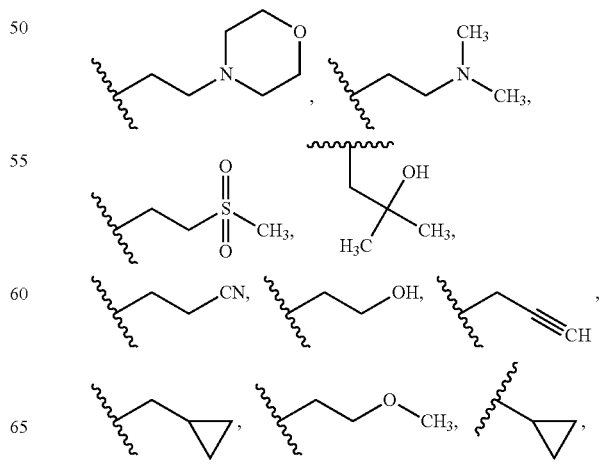

-continued

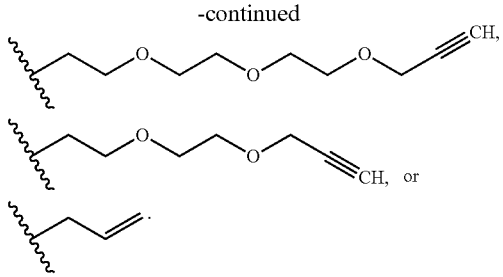

4. The compound according to claim 1, wherein $R^4$ is H, $CH_3$ or —C(O)OR.

5. The compound according to claim 1, wherein $R^x$ and $R^y$ are taken together with their intervening atoms to form a optionally substituted 5-6 membered saturated, partially unsaturated, or aromatic fused ring having 1-2 heteroatoms independently selected from nitrogen, oxygen, or sulfur.

6. A pharmaceutically acceptable composition comprising the compound according to claim 1, and a pharmaceutically acceptable carrier, adjuvant, or vehicle.

7. The composition according to claim 6, in combination with an additional therapeutic agent.

* * * * *